US012263250B2

(12) United States Patent
Xie et al.

(10) Patent No.: US 12,263,250 B2
(45) Date of Patent: Apr. 1, 2025

(54) NANOFIBER SEGMENTS AND METHODS OF USE THEREOF

(71) Applicant: BOARD OF REGENTS OF THE UNIVERSITY OF NEBRASKA, Lincoln, NE (US)

(72) Inventors: Jingwei Xie, Omaha, NE (US); Sunil Kumar Boda, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 683 days.

(21) Appl. No.: 17/044,949

(22) PCT Filed: Apr. 23, 2019

(86) PCT No.: PCT/US2019/028610
§ 371 (c)(1),
(2) Date: Oct. 2, 2020

(87) PCT Pub. No.: WO2019/209762
PCT Pub. Date: Oct. 31, 2019

(65) Prior Publication Data
US 2021/0212949 A1  Jul. 15, 2021

Related U.S. Application Data

(60) Provisional application No. 62/661,171, filed on Apr. 23, 2018, provisional application No. 62/661,174, filed on Apr. 23, 2018.

(51) Int. Cl.
*A61K 9/16* (2006.01)
*A61K 9/00* (2006.01)
(Continued)

(52) U.S. Cl.
CPC .......... *A61K 9/1658* (2013.01); *A61K 9/0024* (2013.01); *A61K 9/1641* (2013.01);
(Continued)

(58) Field of Classification Search
CPC ............................. A61K 9/165; A61L 27/227
See application file for complete search history.

(56) References Cited

U.S. PATENT DOCUMENTS 10,799,620 B2  10/2020  Xie et al.
11,033,659 B2  6/2021  Xie et al.
(Continued)

FOREIGN PATENT DOCUMENTS

| WO | 2009/01165 A1 * | 12/2008 |
| WO | 2009/011658 A1 * | 1/2009 |
| WO | 2009/088777 A1 | 7/2009 |

OTHER PUBLICATIONS

Wang et al, Dentin Regeneration by Stem Cells of Apical Papilla on Injectable Nanofibrous Microspheres and Simulated Controlled BMP-2 Release, Acta Biomaterials, vol. 36, pp. 63-72. (Year: 201).*
(Continued)

*Primary Examiner* — Carlos A Azpuru
(74) *Attorney, Agent, or Firm* — Robert C. Netter, Jr.; Dann, Dorfman, Herrell & Skillman

(57) ABSTRACT

Nanofiber segments comprising polymeric electrospun nanofibers are provided as well as methods of use thereof and methods of making.

31 Claims, 23 Drawing Sheets

Specification includes a Sequence Listing.

(51) Int. Cl.
   *A61L 27/22* (2006.01)
   *A61L 27/54* (2006.01)
   *B82Y 5/00* (2011.01)
   *B82Y 30/00* (2011.01)
   *B82Y 40/00* (2011.01)

(52) U.S. Cl.
   CPC .............. *A61L 27/227* (2013.01); *A61L 27/54* (2013.01); *A61L 2400/12* (2013.01); *A61L 2430/02* (2013.01); *B82Y 5/00* (2013.01); *B82Y 30/00* (2013.01); *B82Y 40/00* (2013.01)

(56) References Cited

U.S. PATENT DOCUMENTS

| | | | |
|---|---|---|---|
| 11,318,224 B2 | 5/2022 | Xie et al. | |
| 11,427,936 B2 | 8/2022 | Xie | |
| 2016/0015792 A1* | 1/2016 | Hendricus van Pinxteren | A61K 9/0014 424/94.64 |
| 2020/0164107 A1 | 5/2020 | Xie et al. | |

OTHER PUBLICATIONS

Wang et al, Dentin Regeneration by Stem Cells of Apical Papilla on Injectable Nanofibrous Microspheres and Simulated Controlled BMP-2 Release, Acta Biomaterials, vol. 36, pp. 63-72 (Year: 2016).*

Xie, et al., "Electrospray in the dripping mode for cell microencapsulation" J. Colloid Interface Sci. (2007) 312(2):247-55.

Cai, et al., "Aerogel microspheres from natural cellulose nanofibrils and their application as cell culture scaffold" Biomacromolecules (2014) 15(7):2540-7.

Wang, et al., "Dentin regeneration by stem cells of apical papilla on injectable nanofibrous microspheres and stimulated by controlled BMP-2 release" Acta Biomater. (2016) 36:63-72.

Boda, et al., "Electrospraying Electrospun Nanofiber Segments into Injectable Microspheres for Potential Cell Delivery" ACS Appl. Mater. Interfaces (2018) 10(30):25069-25079.

Boda, et al., "Mineralized nanofiber segments coupled with calcium-binding BMP-2 peptides for alveolar bone regeneration" Acta Biomater. (2019) 85:282-293.

Weng, et al., "Novel 3D Hybrid Nanofiber Aerogels Coupled with BMP-2 Peptides for Cranial Bone Regeneration" Adv. Healthcare Mater. (2018) 7:1701415.

Choi, et al., "Uniform beads with controllable pore sizes for biomedical applications" Small (2010) 6(14):1492-8.

Cai, et al., "Porous microsphere and its applications" Int. J. Nanomedicine (2013) 8:1111-20.

Liu, et al., "Nanofibrous hollow microspheres self-assembled from star-shaped polymers as injectable cell carriers for knee repair" Nat. Mater. (2011) 10(5):398-406.

Zhou, et al., "Chitosan microspheres with an extracellular matrix-mimicking nanofibrous structure as cell-carrier building blocks for bottom-up cartilage tissue engineering" Nanoscale (2016) 8(1):309-17.

Xie, et al., "Electrohydrodynamic atomization: A two-decade effort to produce and process micro-/nanoparticulate materials" Chem. Eng. Sci. (2015) 125:32-57.

Boda, et al., "Electrospraying an enabling technology for pharmaceutical and biomedical applications: A review" J. Aerosol. Sci. (2018) 125:164-181.

Zhou, et al., "Preparation and characterization of polycaprolactone microspheres by electrospraying" Aerosol Sci. Technol. (2016) 50(11):1201-1215.

Choi, et al., "Fabrication of Microbeads with a Controllable Hollow Interior and Porous Wall Using a Capillary Fluidic Device" Adv. Funct. Mater. (2009) 19(18):2943-2949.

Chang, et al., "Injectable scaffolds: Preparation and application in dental and craniofacial regeneration" Mater. Sci. Eng. R Rep. (2017) 111:1-26.

Ma, et al., "Hierarchical Nanofibrous Microspheres with Controlled Growth Factor Delivery for Bone Regeneration" Adv. Healthcare Mater. (2015) 4:2699-2708.

Chen, et al., "Electrospinning: An enabling nanotechnology platform for drug delivery and regenerative medicine" Adv Drug Deliv. Rev. (2018) 132:188-213.

Li, et al., "Therapeutic angiogenesis in ischemic muscles after local injection of fragmented fibers with loaded traditional Chinese medicine" Nanoscale (2015) 7(30):13075-87.

* cited by examiner

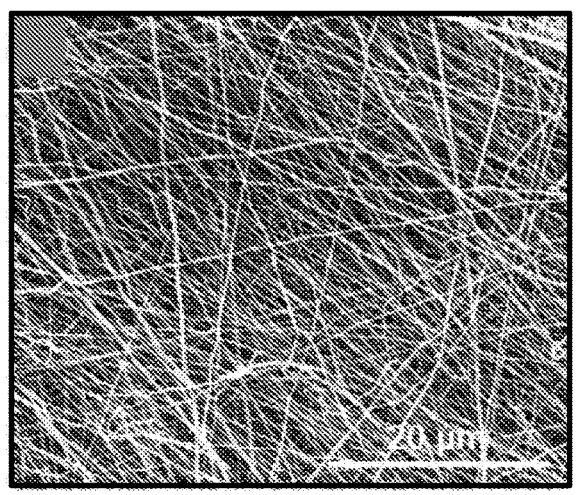
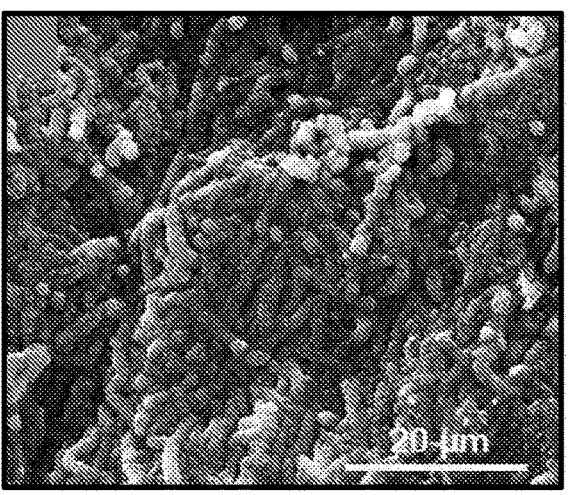
FIG. 9A
FIG. 9B
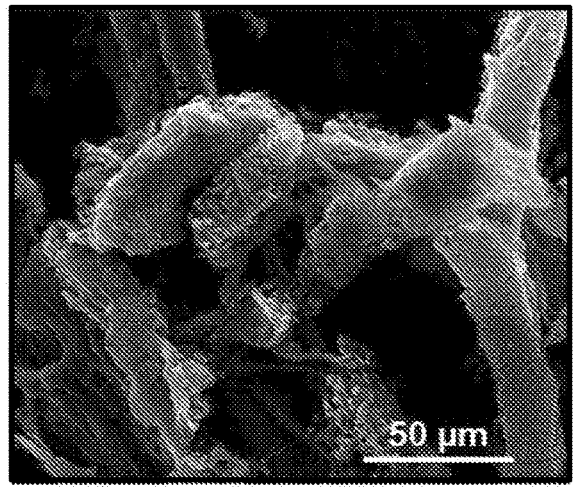
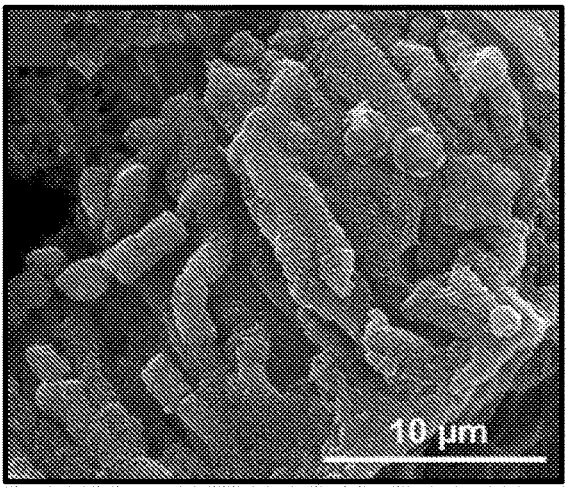
FIG. 9C
FIG. 9D
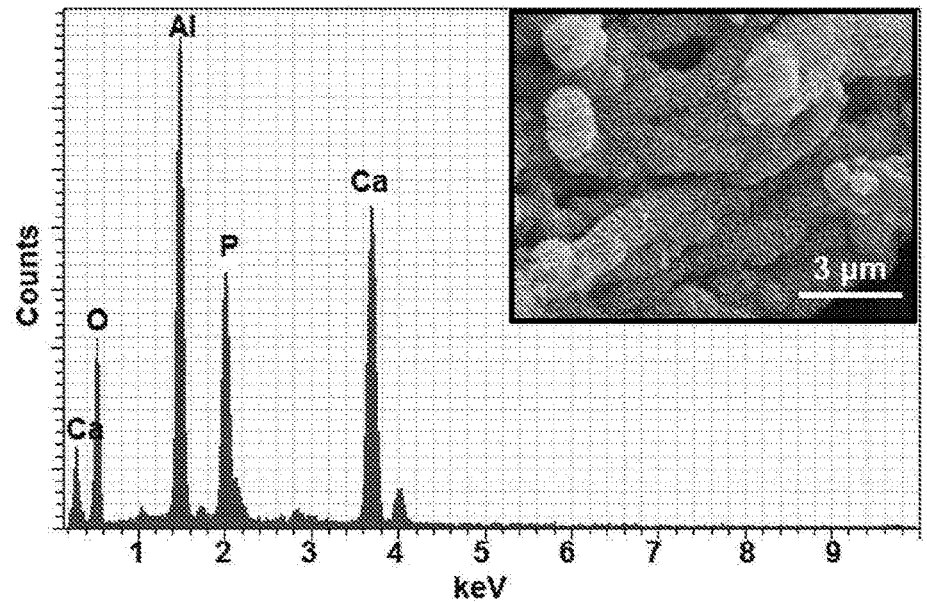
FIG. 9E

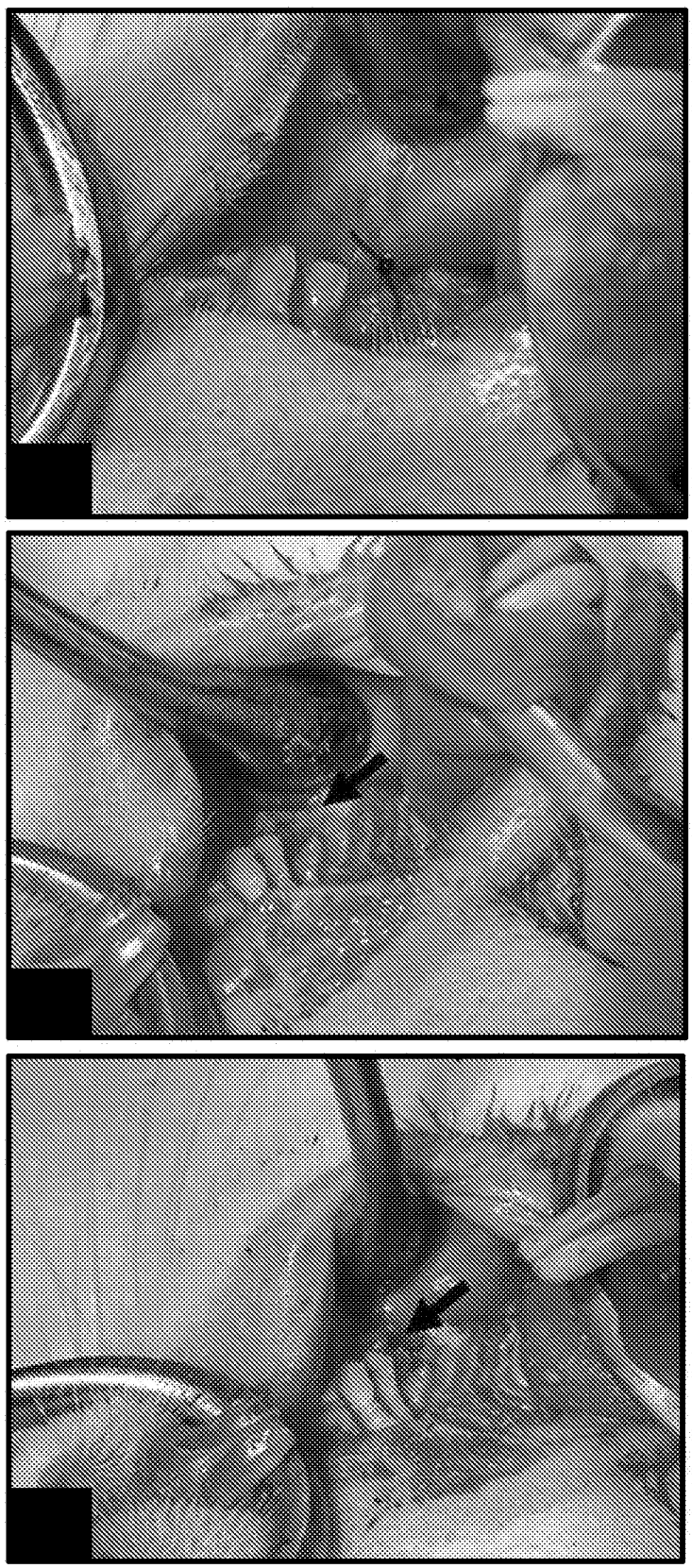

NANOFIBER SEGMENTS AND METHODS OF USE THEREOF

This application is a § 371 application of PCT/US2019/028610, filed Apr. 23, 2019, which claims priority under 35 U.S.C. § 119 (e) to U.S. Provisional Patent Application No. 62/661,171, filed Apr. 23, 2018 and U.S. Provisional Patent Application No. 62/661,174, filed Apr. 23, 2018. The foregoing application is incorporated by reference herein.

This invention was made with government support under Grant No. R21 DE027516 awarded by the National Institutes of Health. The government has certain rights in the invention.

FIELD OF THE INVENTION

This application relates to the fields of nanofiber structures. More specifically, this invention provides methods of synthesizing injectable nanofiber segments and nanofiber microspheres and methods of use thereof.

BACKGROUND OF THE INVENTION

Several publications and patent documents are cited throughout the specification in order to describe the state of the art to which this invention pertains. Each of these citations is incorporated herein by reference as though set forth in full.

Microspheres are at the forefront of drug delivery and tissue regeneration, as are three-dimensional (3D) porous scaffolds for the healing of large critical-sized defects (Hossain, et al., Prog. Biomater. (2015) 4:1-19). Microspheres provide additional advantages over 3D scaffolds in that it can be cumbersome to fabricate 3D scaffolds for filling irregular-shaped defects, while microspheres can be easily injected into any defect irrespective of the shape and geometry (Zhang, et al., Nanomedicine (2016) 11:1611-1628). Further, the injectability of microspheres confers minimally invasive treatments as against the gross surgical procedures necessary for implantation of 3D porous scaffolds (Dreifke, et al., J. Biomed. Mater. Res., Part A (2013) 101:2436-2447). The increased use of injectable microspheres also coincides with the advancements in biomedical imaging technologies for tracking them in the body post-injection (Saralidze, et al., Materials (2010) 3:3537-3564). Apart from self-assembling/ionically cross-linked hydrogels, microspheres constitute a unique class of injectable biomaterials (Chang, et al., Mater. Sci. Eng. (2017) 111:1-26). However, the function of injectable microspheres is similar to 3D scaffolds in that they can also be used to deliver cells and growth factors/drugs to the site of injury for tissue regeneration (Ma, et al., Tissue Eng., Part C (2017) 23:50-59). A host of natural polymers such as gelatin, chitosan, and alginate as well as synthetic polymers such as poly-lactic-co-glycolic acid (PLGA) and polycaprolactone (PCL) have been used for the fabrication of microspheres for various applications. The choice of the material used for microsphere fabrication is dictated by its biodegradability as necessary for drug delivery and sustained release as well as tissue regeneration (Edlund, et al., *Degradable Polymer Microspheres for Controlled Drug Delivery*, Degradable Aliphatic Polyesters, Springer Berlin Heidelberg, (2002) pp 67-112; Lu, et al., Ann. Biomed. Eng. (2016) 44:1894-1907). Also, the method of fabrication can critically affect the morphology, texture, and particle size distribution of the microspheres. For instance, to fabricate uniform-sized microspheres/microbeads with controllable porosity, a microfluidic device with optimized flow rates was employed for PLGA microspheres (Choi, et al., Small (2010) 6:1492-1498). Aerogel microspheres have also been fabricated by high-pressure spraying of cellulose nanofibrils through a steel nozzle into liquid nitrogen (Cai, et al., Biomacromolecules (2014) 15:2540-2547).

A broad range of microsphere morphologies have been fabricated by different methods, including solid, hollow, porous, and nanofiber (NF) microspheres and their combinations. The microsphere morphology can confer additional functionalities such as controlled and/or sequential growth factor/drug release from core-shell microspheres, enhanced cell viability and loading efficiency for porous microspheres, and tissue specificity as osteochondral repair for nanofiber microspheres (Chang, et al., Biomaterials (2013) 34:9990-9997; Cai, et al., Int. J. Nanomed. (2013) 8:1111-1120; Liu, et al., Nat. Mater. (2011) 10:398-406). The solid microspheres possess low cell carrier efficiency because of smaller surface area, whereas porous and nanofiber microspheres can be loaded with more cells per microsphere arising from their larger surface area (Zhou, et al., Nanoscale (2016) 8:309-317). Previous nanofiber microspheres have been fabricated by the self-assembly of star-shaped poly(L-lactic acid) (ss-PLLA) or gelation of chitosan coupled with microfluidics (Liu, et al., Nat. Mater. (2011) 10:398-406; Zhou, et al., Nanoscale (2016) 8:309-317). These methods are limited by the polymer chemistry such as the necessity for specific surface functional groups and therefore selectively applicable to few biopolymers.

These limitations necessitate the development of a fabrication method of nanofiber microspheres, independent of the polymer chemistry and composition.

SUMMARY OF THE INVENTION

In accordance with the instant invention, nanofiber segments and nanofiber microspheres are provided. In a particular embodiment, the nanofiber segments and nanofiber microspheres comprise electrospun nanofibers (e.g., uniaxially-aligned, random, entangled, and/or electrospun fibers). The nanofiber segments and nanofiber microspheres may comprise a material that enhances water absorption, such as gelatin, chitosan, or collagen. In a particular embodiment, the nanofiber segments and nanofiber microspheres are crosslinked and/or thermally treated. In a particular embodiment, the nanofiber segments and nanofiber microspheres are mineralized. The nanofiber segments and nanofiber microspheres may also comprise one or more agents or compounds such as therapeutic agents. In a particular embodiment, the nanofiber segments and nanofiber microspheres comprise cells and/or tissue. The nanofiber segments and nanofiber microspheres of the instant invention may comprise a material that enhances water absorption; may be crosslinked and/or thermally treated; may be mineralized; may comprise one or more agents or compounds such as therapeutic agents; and/or may comprise cells and/or tissue, or any combination of any one, two, three, four, or five of these features. Methods of synthesizing the nanofiber segments and nanofiber microspheres of the instant invention are also provided.

In accordance with another aspect of the instant invention, methods of using the nanofiber segments and nanofiber microspheres are provided. For example, the nanofiber structures may be used to enhance wound healing, build tissue constructs, promote tissue regeneration (e.g., bone regeneration), reduce, inhibit, prevent, and/or eliminate infection, local delivery of drugs, and/or inhibit bleeding.

BRIEF DESCRIPTION OF THE DRAWINGS

FIGS. 9A-9C provide images of mineralized nanofiber fragments by electrospinning of thin nanofiber membrane (FIG. 9A), simulated body fluid (SBF) mineralization of the membrane (FIG. 9B), and cryocutting of the mineralized nanofiber membranes to 20 μm segments (FIG. 9C). FIG. 9D provides a magnified image of the mineralized short nanofiber segments and FIG. 9E provides an energy dispersive X-ray spectroscopy (EDAX) spectrum of mineralized nanofiber fragments.

FIGS. 10C and 10B provide fluorescence micrographs of the mineralized PCG NF fragments after E7-BMP-2-FITC peptide loading (FIG. 10C) and after 28 days of release (FIG. 10D).

FIGS. 11A-11C provide intraoperative images of the critical-sized defect created in rat maxillae (upper jaw) after extraction of the first molar tooth. FIG. 11A: Defect drilled into the upper jaw bone (indicated by arrow), FIG. 11B: Filling of defect with mineralized nanofiber graft, and FIG. 11C: Suturing of the tissue around the defect to hold the graft in place.

DETAILED DESCRIPTION OF THE INVENTION

Figure 1:
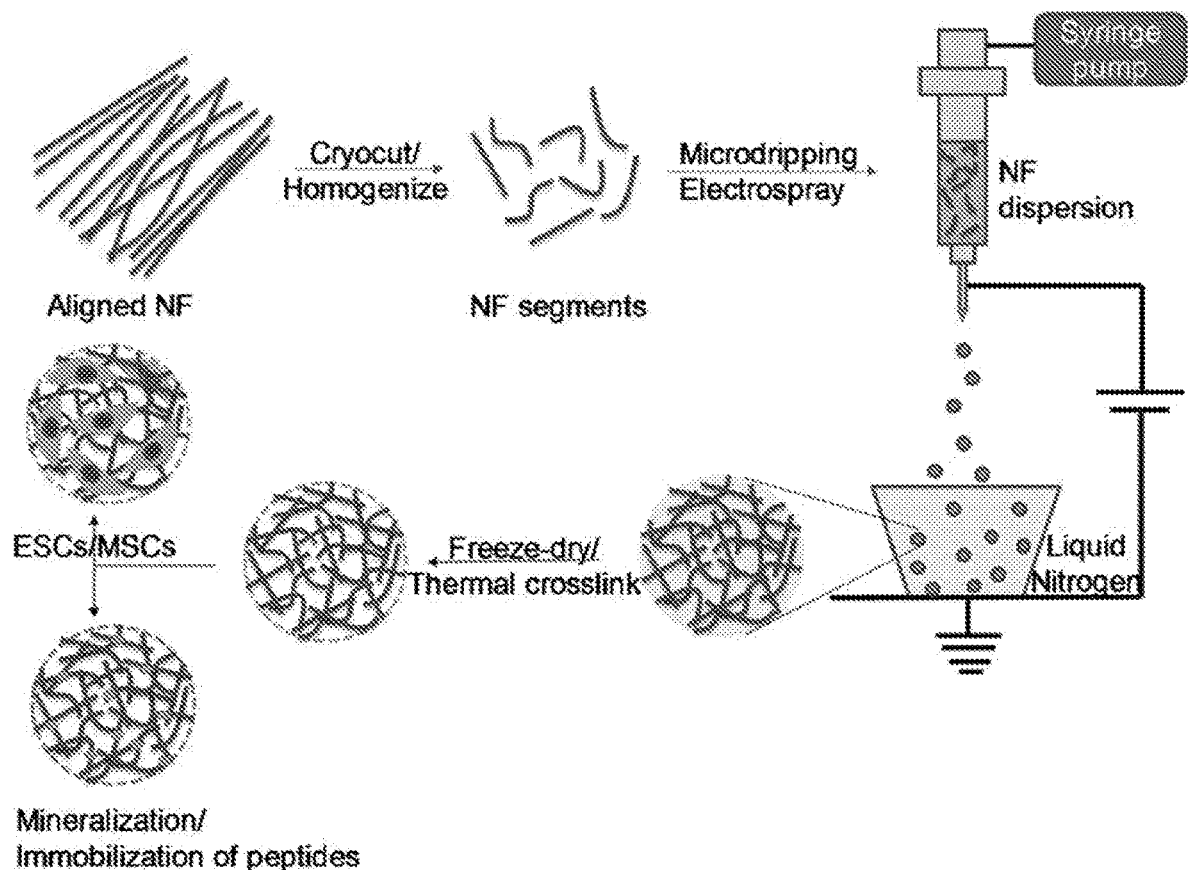
FIG. 1 provides a schematic overview of the fabrication of nanofiber microspheres from segmented/homogenized electrospun nanofibers and their applications for stem cell and drug/peptide delivery.

Herein, methods for fabricating nanofiber microspheres by combining electrospinning and electrospraying are provided. For example, electrospraying of aqueous dispersions of electrospun nanofiber segments with desired length obtained by either cryocutting or homogenization into a cryocoolant (e.g., liquid nitrogen) followed by freeze-drying and thermal treatment was used to form nanofiber microspheres. This method is largely independent of polymer chemistry and composition. Further, the approach is highly versatile for fabricating nanofiber microspheres of a wide variety of compositions and morphologies for cell therapy in a minimally invasive way. Indeed, electrospraying allows for the production of nano/microparticles with a broad range of particle morphologies (Xie, et al., Chem. Eng. Sci. (2015) 125:32-57). Further, electrospray offers the advantage of a precise control over the particle size by manipulating the processing parameters such as the applied voltage, flow rate, and the distance between the spray needle and collector (Xie, et al., Chem. Eng. Sci. (2015) 125:32-57). Particularly, in the dripping mode, a uniform size distribution of cell encapsulations within alginate microbeads can be obtained (Xie, et al., J. Colloid Interface Sci. (2007) 312:247-255). Herein, a variety of morphologies were achieved including solid, nanofiber, porous and nanofiber microspheres, and hollow nanofiber microspheres. Furthermore, a broad range of polymer and inorganic bioactive glass nanofiber-based nanofiber microspheres can be fabricated by electrospraying of their short nanofiber dispersions, indicating a comprehensive applicability of this method. A higher cell carrier efficiency of nanofiber microspheres as compared to solid microspheres was demonstrated with rat bone marrow-derived mesenchymal stem cells, along with the formation of microtissue-like structures in situ, when injected into microchannel devices. Also, mouse embryonic stem cells underwent neural differentiation on the nanofiber microspheres, as indicated by positive staining of β-III-tubulin and neurite outgrowth. Taken together, nanofiber microspheres have been provided that are injectable and have improved viability and maintenance of stem cells for application in cell therapy.

In accordance with the instant invention, nanofiber microspheres are provided. The nanofibers of the instant invention can be fabricated by any method. In a particular embodiment, the nanofiber microspheres comprise electrospun nanofibers. In a particular embodiment, the nanofiber microspheres comprise uniaxially aligned fibers, random fibers, and/or entangled fibers. While the application generally describes nanofibers (fibers having a diameter less than about 1 µm (e.g., average diameter)) and the synthesis of nanofibrous microspheres, the instant invention also encompasses microfibers (fibers having a diameter greater than about 1 µm (e.g., average diameter)) and the synthesis of microfibrous microspheres. The nanofiber microsphere may be crosslinked (e.g., chemically crosslinked) and/or thermally treated. In a particular embodiment, the nanofibers and/or nanofiber microspheres are air plasma treated.

The nanofibers of the nanofiber microspheres are short segments. The nanofiber segments of the instant invention can be fabricated by any method. In a particular embodiment, the nanofiber segments are derived from longer nanofibers (e.g., electrospun fibers), such as by cryocutting and/or homogenization (e.g., by sonication, particularly probe sonication). In a particular embodiment, the nanofiber segments are less than about 150 µm in length, particularly about 1 µm to about 100 µm in length, about 5 µm to about 100 µm in length, about 5 µm to about 80 µm in length, about 10 µm to about 60 µm in length, about 20 µm to about 50 µm in length, or about 30 µm to about 50 µm in length. In a particular embodiment, the nanofiber segments of the nanofiber microsphere have a median or mean length of about 10 µm to about 60 µm in length, about 20 µm to about 50 µm in length, about 20 µm to about 30 µm in length, or about 30 µm to about 50 µm in length.

The nanofiber microspheres of the instant invention can be of any desired size. In a particular embodiment, the nanofiber microsphere has a diameter of less than about 1 mm or 2 mm. In a particular embodiment, the nanofiber microsphere has a diameter of less than about 1 mm or less than about 500 µm. In a particular embodiment, the nanofiber microsphere has a diameter of about 1 µm to about 2 mm, about 10 µm to about 1 mm, about 50 µm to about 1 mm, about 100 µm to about 1 mm, about 50 µm to about 500 µm, about 100 µm to about 500 µm, about 100 µm to about 250 µm, or about 150 µm. While the application generally describes microspheres (spheres having a diameter greater than about 1 µm (e.g., average diameter)) and the synthesis of nanofiber microspheres, the instant invention also encompasses nanospheres (spheres having a diameter less than about 1 µm (e.g., average diameter)) and the synthesis of nanofiber nanospheres.

The nanofibers of the instant invention may comprise any polymer. In a particular embodiment, the polymer is biocompatible. The polymer may be biodegradable or non-biodegradable. In a particular embodiment, the polymer is a biodegradable polymer. The polymer may by hydrophobic, hydrophilic, or amphiphilic. In a particular embodiment, the polymer is hydrophobic. In a particular embodiment, the polymer is hydrophilic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyperbranched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly (caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO.

Amphiphilic copolymers or polymer composites may comprise a hydrophilic polymer (e.g., segment) and a hydrophobic polymer (e.g., segment) from those listed above (e.g., gelatin/polyvinyl alcohol (PVA), PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/gelatin, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA).

In a particular embodiment, the nanofiber comprises polymethacrylate, poly vinyl phenol, polyvinylchloride, cellulose, polyvinyl alcohol, polyacrylamide, poly(lactic-co-glycolic acid) (PLGA), collagen, polycaprolactone, polyurethanes, polyvinyl fluoride, polyamide, silk, nylon, polybenzimidazole, polycarbonate, polyacrylonitrile, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene gricol, polyethylene glycol, poly(ethylene-co-vinyl alcohol), polyacrylnitrile, polyvinyl pyrrolidone, polymetha-phenylene isophthalamide, gelatin, alginate, chitosan, starch, pectin, cellulose, methylcellulose, sodium polyacrylate, starch-acrylonitrile co-polymers, bioactive glass, and/or combinations of two or more polymers. Multiple polymers may be mixed to form the nanofibers. The polymers may be mixed in equal ratios or various ratios depending on the desired properties of the nanofibers. Examples of polymers and polymer combinations for nanofibers include but are not limited to PLGA-gelatin nanofibers (e.g., at a 1:1 ratio), PLGA-collagen-gelatin nanofibers (e.g., at a 1:0.5:0.5 ratio), PCL-gelatin nanofibers (e.g., at a 1:1 ratio), bioactive glass nanofibers dispersed in alginate, and PLGA short fibers dispersed in gelatin. In a particular embodiment, at least collagen and/or gelatin is used. In a particular embodiment, the polymer comprises polycaprolactone (PCL). In a particular embodiment, the polymer comprises 1) polycaprolactone (PCL) and 2) gelatin and/or collagen (e.g., at a 1:1 ratio).

In a particular embodiment, the nanofibers and/or nanofiber microsphere are coated with additional materials to enhance their properties. For example, the nanofibers and/or nanofiber microsphere may be coated with collagen, a proteoglycans, elastin, or a glycosaminoglycans (e.g., hyaluronic acid, heparin, chondroitin sulfate, or keratan sulfate). In a particular embodiment, the nanofibers and/or nanofiber microsphere comprise a material that enhances the nanofiber microsphere's ability to absorb fluids, particularly aqueous solutions (e.g., blood). In a particular embodiment, the nanofibers and/or nanofiber microsphere are coated with the material which enhances the absorption properties. The term "coat" refers to a layer of a substance/material on the surface of a structure. Coatings may, but need not, also impregnate the nanofibers and/or nanofiber microsphere. Further, while a coating may cover 100% of the nanofiber and/or nanofiber microsphere, a coating may also cover less than 100% of the surface of the nanofiber and/or nanofiber microsphere (e.g., at least about 75%, at least about 80%, at least about 85%, at least about 90%, at least about 95%, at least about 98%, or more of the surface may be coated). Materials which enhance the absorption properties of the nanofibers and/or nanofiber microsphere include, without limitation: gelatin, alginate, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the material is a hydrogel (e.g., a polymer matrix able to retain water, particularly large amounts of water, in a swollen state). In a particular embodiment, the material is gelatin. In a particular embodiment, the nanofibers and/or nanofiber microsphere are coated with about 0.05% to about 10% coating material (e.g., gelatin), particularly about 0.1% to about 10% coating material (e.g., gelatin) or about 0.1% to about 1% coating material (e.g., gelatin). In a particular embodiment, the material (e.g., hydrogel) is crosslinked.

In a particular embodiment, the nanofibers and/or nanofiber microsphere are mineralized (e.g., comprise minerals and/or coated with minerals). Mineralization, for example, with hydroxyapatite, can enhance the adhesion of osteogenic precursor cells in vitro and in vivo (Duan, et al., Biomacromolecules (2017) 18:2080-2089). In a particular embodiment, the nanofibers and/or nanofiber microsphere are coated with Ca, P, and O. In a particular embodiment, the nanofibers and/or nanofiber microsphere are coated with hydroxyapatite, fluorapatite, or chlorapatite, particularly hydroxyapatite. In a particular embodiment, the nanofibers and/or nanofiber microsphere are immersed in simulated body fluid (SBF) for the mineralization (e.g., a solution comprising NaCl, CaCl$_2$, NaH$_2$PO$_4$, and NaHCO$_3$.

As stated herein, the nanofiber microspheres of the instant invention may be crosslinked and/or thermally treated (e.g., to enhance their stability). Crosslinking may be done using a variety of techniques including thermal crosslinking, chemical crosslinking, and photo-crosslinking. For example, the nanofiber microspheres of the instant invention may be crosslinked with a crosslinker such as, without limitation:

formaldehyde, paraformaldehyde, acetaldehyde, glutaraldehyde, a photocrosslinker, genipin, and natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132; incorporated herein by reference). The crosslinker may be a bifunctional, trifunctional, or multifunctional crosslinking reagent. In a particular embodiment, the crosslinker is glutaraldehyde. In a particular embodiment, the nanofiber microsphere is thermally treated (e.g., at a temperature close to, but below, the melting point of the nanofibers; e.g., about 50° C.).

The morphologies of the nanofiber microspheres can be controlled. Examples of resulting nanofiber microspheres include but are not limited to solid, nanofibrous, porous with nanofibrous structure (including various pore sizes and amounts), and hollow nanofiber microspheres and combinations thereof.

After synthesis, the nanofiber microspheres may be washed or rinsed in water and/or a desired carrier or buffer (e.g., a pharmaceutically or biologically acceptable carrier). The nanofiber microspheres may also be stored in a cold solution, lyophilized and/or freeze-dried.

The nanofiber microspheres of the instant invention may also be sterilized. For example, the nanofiber microspheres can be sterilized using various methods (e.g., by treating with ethylene oxide gas, gamma irradiation, or 70% ethanol).

The nanofiber microspheres of the instant invention may comprise and/or encapsulate cells or tissue. In a particular embodiment, the cells are autologous to the subject to be treated with the nanofiber microsphere. The nanofiber microsphere may comprise and/or encapsulate any cell type. Cell types include, without limitation: embryonic stem cells, adult stem cells, bone marrow stem cells, induced pluripotent stem cells, progenitor cells (e.g., neural progenitor cells), embryonic like stem cells, mesenchymal stem cells, CAR-T cells, immune cells (including but not limited to T cells, B cells, NK cells, macrophages, neutrophils, dendritic cells and modified forms of these cells and various combinations thereof), cell based vaccines, and cell lines expressing desired therapeutic proteins and/or genes. In a particular embodiment, the cells comprise stem cells. In a particular embodiment, the cells comprise dermal fibroblasts. In a particular embodiment, the nanofiber microsphere comprises and/or encapsulates cell spheroids. In a particular embodiment, the nanofiber microsphere comprises and/or encapsulates tissue samples (e.g., minced tissue), such as skin tissue samples or bone samples. The cells or tissue may be cultured within the nanofiber microspheres (e.g., the cells or tissue may be cultured for sufficient time to allow for growth within and/or infiltration into the nanofiber microsphere). For example, the cells or tissue may be cultured in the nanofiber microsphere for 1 day, 2 days, 3 days, 4 days, 5 days, or more.

The nanofiber microspheres of the instant invention may comprise or encapsulate at least one agent, particularly a bioactive agent, biologic, and/or drug. In a particular embodiment, the agent is hydrophilic. The agent may be added to the nanofiber microsphere during synthesis and/or after synthesis. The agent may be conjugated (e.g., directly or via a linker) to the nanofiber microsphere and/or coating material, encapsulated by the nanofiber microsphere, and/or coated on the nanofiber microsphere (e.g., with, underneath, and/or on top of the coating that enhances the nanofiber microsphere's ability to absorb fluids, if present). In a particular embodiment, the agent is not directly conjugated to the nanofiber microsphere (e.g., it is encapsulated). In a particular embodiment, the agent is conjugated or linked to the nanofiber microsphere (e.g., surface conjugation or coating). In a particular embodiment, the agents are administered with but not incorporated into the nanofiber microspheres.

Biologics include but are not limited to proteins, peptides, antibodies, antibody fragments, DNA, RNA, and other known biologic substances, particularly those that have therapeutic use. In a particular embodiment, the agent is a drug or therapeutic agent (e.g., a small molecule) (e.g., analgesic, growth factor, anti-inflammatory, signaling molecule, cytokine, antimicrobial (e.g., antibacterial, antibiotic, antiviral, and/or antifungal), blood clotting agent, factor, or protein, pain medications (e.g., anesthetics), etc.). In a particular embodiment, the agent enhances tissue regeneration, tissue growth, and wound healing (e.g., growth factors). In a particular embodiment, the agent treats/prevents infections (e.g., antimicrobials such as antibacterials, antivirals and/or antifungals). In a particular embodiment, the agent is an antimicrobial, particularly an antibacterial. In a particular embodiment, the agent enhances wound healing and/or enhances tissue regeneration (e.g., bone, tendon, cartilage, skin, nerve, and/or blood vessel). Such agents include, for example, growth factors, cytokines, chemokines, immunomodulating compounds, and small molecules. Growth factors include, without limitation: platelet derived growth factors (PDGF), vascular endothelial growth factors (VEGF), epidermal growth factors (EGF), fibroblast growth factors (FGF; e.g., basic fibroblast growth factor (bFGF)), insulin-like growth factors (IGF-1 and/or IGF-2), bone morphogenetic proteins (e.g., BMP-2, BMP-7, BMP-12, BMP-9; particularly BMP-2 fragments, peptides, and/or analogs thereof), transforming growth factors (e.g., TGFβ, TGFβ3), nerve growth factors (NGF), neurotrophic factors, stromal derived factor-1 (SDF-1), granulocyte-macrophage colony-stimulating factor (GM-CSF), granulocyte-colony stimulating factor (G-CSF), erythropoietin (EPO), glial cell-derived neurotrophic factors (GDNF), hepatocyte growth factors (HGF), keratinocyte growth factors (KGF), and/or growth factor mimicking peptides (e.g., VEGF mimicking peptides). Chemokines include, without limitation: CCL21, CCL22, CCL2, CCL3, CCL5, CCL7, CCL8, CCL13, CCL17, CXCL9, CXCL10, and CXCL11. Cytokines include without limitation IL-2 subfamily cytokines, interferon subfamily cytokines, IL-10 subfamily cytokines, IL-1, I-18, IL-17, tumor necrosis factor, and transforming-growth factor beta superfamily cytokines. Examples of small molecule drugs/therapeutic agents include, without limitation, simvastatin, kartogenin, retinoic acid, paclitaxel, vitamins (e.g., vitamin D3), etc. In a particular embodiment, the agent is a blood clotting factor such as thrombin or fibrinogen. In a particular embodiment, the agent is a bone morphogenetic protein (e.g., BMP-2, BMP-7, BMP-12, BMP-9; particularly human; particularly BMP-2 fragments, peptides, and/or analogs thereof). In a particular embodiment, the agent is a BMP-2 peptide such as KIPKASSVPTELSAISTLYL (SEQ ID NO: 1). In a particular embodiment, the agent is a BMP-2 fragment (e.g., up to about 25, about 30, about 35, about 40, about 45, about 50 amino acids, or more of BMP-2) comprising the knuckle epitope (e.g., amino acids 73-92 of BMP-2 or SEQ ID NO: 1). In a particular embodiment, the BMP-2 peptide is linked to a peptide of acidic amino acids (e.g., Asp and/or Glu; particularly about 3-10 or 5-10 amino acids such as E7, E8, D7, D8) and/or bisphosphonate (e.g., at the N-terminus).

The nanofiber microspheres of the present invention may also be modified with targeting moieties (e.g., to enhance delivery to specific sites within the body (e.g., tissue types, disease areas, etc)). Examples of targeting moieties include but are not limited to peptides, proteins, antibodies, antibody fragments, and small molecules. In a particular embodiment, a nanofiber of the microsphere is linked to a targeting ligand. A targeting ligand is a compound that specifically or preferentially binds to a specific type of tissue or cell type. For example, a targeting ligand may be used for engagement or binding of a target cell (e.g., a surface marker or receptor). In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand may be linked directly to the nanofiber or microsphere or via a linker. Generally, the linker is a chemical moiety comprising a covalent bond or a chain of atoms that covalently attaches the ligand to the polymer or surfactant. The linker can be linked to any synthetically feasible position of the ligand and the polymer or surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). The linker may be non-degradable and may be a covalent bond or any other chemical structure which cannot be substantially cleaved or cleaved at all under physiological environments or conditions. The nanofiber microspheres of the instant invention may comprise targeted and/or non-targeted nanofibers. In a particular embodiment, the molar ratio of targeted and non-targeted nanofibers in the microsphere of the instant invention is from about 0.001 to 100%, about 1% to about 99%, about 5% to about 95%, about 10% to about 90%, about 25% to about 75%, about 30% to about 60%, or about 40%.

While the instant invention has been described herein with regard to nanofiber microspheres, the instant invention also encompasses nanofiber segments as described herein (i.e., wherein the nanofiber segments are not in the form of a microsphere). The nanofiber segments of the instant invention can be fabricated by any method. In a particular embodiment, the nanofiber segments are derived from longer nanofibers (e.g., electrospun fibers), such as by cryocutting and/or homogenization (e.g., by sonication, particularly probe sonication). As explained herein with regard to nanofiber microspheres, the nanofibers of the instant invention may comprise any polymer. In a particular embodiment, the nanofibers are less than about 150 μm in length, particularly about 1 μm to about 100 μm in length, about 5 μm to about 100 μm in length, about 5 μm to about 80 μm in length, about 10 μm to about 60 μm in length, about 20 μm to about 50 μm in length, or about 30 μm to about 50 μm in length. In a particular embodiment, the nanofibers of the nanofiber microsphere have a median or mean length of about 10 μm to about 60 μm in length, about 20 μm to about 50 μm in length, about 20 μm to about 30 μm in length, or about 30 μm to about 50 μm in length. In a particular embodiment, the nanofiber segments are air plasma treated.

As described herein with regard to nanofiber microspheres, the nanofiber segments may be coated. For example, the nanofiber segments may comprise a material that enhances the nanofiber segment's ability to absorb fluids, particularly aqueous solutions (e.g., blood). In a particular embodiment, the nanofiber segments are coated with the material which enhances the absorption properties.

As described herein with regard to nanofiber microspheres, the nanofiber segments may be mineralized.

As described herein with regard to nanofiber microspheres, the nanofiber segments of the instant invention may be crosslinked or thermally treated (e.g., to enhance their stability). Crosslinking may be done using a variety of techniques including thermal crosslinking, chemical crosslinking, and photo-crosslinking.

After synthesis, the nanofiber segments may be washed or rinsed in water and/or a desired carrier or buffer (e.g., a pharmaceutically or biologically acceptable carrier). The nanofiber segments may also be stored in a cold solution, lyophilized and/or freeze-dried.

The nanofiber segments of the instant invention may also be sterilized. For example, the nanofiber segments can be sterilized using various methods (e.g., by treating with ethylene oxide gas, gamma irradiation, or 70% ethanol).

As described herein with regard to nanofiber microspheres, the nanofiber segments of the instant invention may comprise and/or encapsulate cells or tissue. As described herein with regard to nanofiber microspheres, the nanofiber segments of the instant invention may comprise or encapsulate at least one agent, particularly a bioactive agent, biologic, and/or drug. The agent may be added to the nanofiber segments during synthesis and/or after synthesis. The agent may be conjugated (e.g., directly or via a linker) to the nanofiber segments and/or coating material.

The nanofiber segments of the present invention may also be modified with targeting moieties (e.g., to enhance delivery to specific sites within the body (e.g., tissue types, disease areas, etc.)), as described herein with regard to nanofiber microspheres. The targeting ligand may be linked directly to the nanofiber segment or via a linker.

In accordance with another aspect of the instant invention, methods of synthesizing the nanofiber microspheres described herein are provided. In a particular embodiment, the method comprises electrospraying a composition comprising nanofiber segments (e.g., a suspension or dispersion of nanofiber segments in a nonsolvent (e.g., water)) into freezing conditions (e.g., a media or liquid (e.g., a nonsolvent) having a temperature of less than about −20° C., particularly less than about −80° C.; e.g., liquid nitrogen), thereby synthesizing the nanofiber microspheres. In a particular embodiment, the method further comprises freeze drying and/or lyophilizing the synthesized nanofiber microspheres. In a particular embodiment, the method further comprises modifying the nanofibers and/or nanofiber microspheres as described herein (e.g., air plasma treatment, coating, mineralization, etc.). In a particular embodiment, the method further comprises washing and/or sterilizing the nanofiber microspheres. In a particular embodiment, the method further comprises adding or encapsulating cells and/or agents, as described herein, to or within the nanofiber microsphere (e.g., culturing the nanofiber microspheres with cells, thereby allowing the cells to infiltrate the nanofiber microsphere).

In a particular embodiment, the electrospraying comprises microdripping the composition comprising the nanofiber segments. As demonstrated in Example 1, the size and the morphology of the microspheres can be controlled by altering the conditions of the electrospraying process. For example, the size and/or morphology of the nanofiber microspheres can be controlled by adjusting the conditions of the electrospraying including, without limitation, concentration of nanofiber segments in the composition, voltage, needle gauge, flow rate, and/or distance between needle tip and collector (e.g., aluminum foil immersed in liquid nitrogen).

For example, a current voltage of about 8 to about 10 kV will typically produce microspheres with size ranging from 100 μm to 400 In a particular embodiment, the current voltage is between about 4 kV and about 14 kV. In a particular embodiment, the concentration of nanofiber segments in the composition is about 1 mg/ml to about 50 mg/ml, about 5 mg/ml to about 30 mg/ml, or about 10 to about 20 mg/ml.

In accordance with another aspect of the instant invention, methods of synthesizing the nanofiber segments described herein are provided. The methods of the instant invention for synthesizing nanofiber microspheres may further comprise synthesizing the nanofiber segments prior to electrospraying. In a particular embodiment, the method of synthesizing the nanofiber segments comprises synthesizing nanofibers (e.g., electrospinning nanofibers) and then cutting and/or breaking the nanofibers into shorter nanofiber segments. In a particular embodiment, a nanofiber mat is synthesized prior to cutting and/or breaking. Cutting or breaking of the nanofibers to produce short nanofiber segments can be done using a variety of methods including but not limited to cryo-cutting, homogenization, wet milling, and cryomilling. In a particular embodiment, the nanofibers or nanofiber mat is cryo-cut. For example, the nanofibers or nanofiber mat may be frozen (e.g., in a liquid such as water (e.g., at about −20° C. or lower or at about −80° C. or lower) and then the frozen block containing the nanofibers or nanofiber mat is cut with a cryotome (e.g., at about −20° C. or lower). In a particular embodiment, the nanofibers or nanofiber mat can be broken or homogenized into nanofiber segments by sonication. For example, the nanofibers or nanofiber mat can be placed into water or an aqueous solution and homogenized using an ultrasonic probe sonicator (e.g., equipped with a microtip probe (e.g., ⅛ mm)). In a particular embodiment, the nanofibers or nanofiber mat are cut into nanofiber segments using cryomilling (e.g., in liquid nitrogen). In a particular embodiment, the method further comprises modifying the nanofibers as described herein (e.g., air plasma treatment, coating, mineralization, etc.).

The nanofiber microspheres of the instant invention can be used to create tissue architectures for a variety of application including, without limitation: wound healing, tissue engineering, tissue growth, tissue repair, tissue regeneration, and engineering 3D in vitro tissue models. The nanofiber microspheres can also be combined with a variety of hydrogels or biological matrices/cues to form 3D hybrid scaffolds that can release biologically functional agents. The tissue constructs can be used for regeneration of many tissue defects (e.g., skin, bone) and healing of various wounds (e.g., injuries, diabetic wounds, venous ulcer, pressure ulcer, burns). The nanofiber microspheres may be used ex vivo to generate tissue or tissue constructs/models. The nanofiber microspheres may also be used in vivo in patients (e.g., human or animal) for the treatment of various diseases, disorders, and wounds. In a particular embodiment, the nanofiber microsphere stimulates the growth of existing tissue and/or repair of a wound or defect when applied in vivo. The nanofiber microspheres can be used for engineering, growing, and/or regeneration of a variety of tissues including but not limited to skin, bone, cartilage, muscle, nervous tissue, and organs (or portions thereof).

In accordance with the instant invention, the nanofiber segments and/or nanofiber microspheres may be used in inducing and/or improving/enhancing wound healing and inducing and/or improving/enhancing tissue regeneration. The nanofiber segments and/or nanofiber microsphere of the present invention can be used for the treatment, inhibition, and/or prevention of any injury or wound. In a particular embodiment, the method comprises administering nanofiber segments and/or nanofiber microsphere comprising an agent and/or cell as described herein. Nanofiber segments and/or nanofiber microspheres of the instant invention can be loaded with different cell types as necessary for regeneration of various tissues. In a particular embodiment, the nanofiber segments and/or nanofiber microsphere comprises blood clotting factors (e.g., for accelerating blood clot formation and/or preventing blood loss). For example, the nanofiber segments and/or nanofiber microsphere can be used to induce, improve, or enhance wound healing associated with surgery (including non-elective (e.g., emergency) surgical procedures or elective surgical procedures). Elective surgical procedures include, without limitation: liver resection, partial nephrectomy, cholecystectomy, vascular suture line reinforcement and neurosurgical procedures. Non-elective surgical procedures include, without limitation: severe epistaxis, splenic injury, liver fracture, cavitary wounds, minor cuts, punctures, gunshot wounds, and shrapnel wounds. The nanofiber segments and/or nanofiber microsphere of the present invention can also be incorporated into delivery devices (e.g., a syringe or spray (e.g., aerosol spray)) that allow for their injection/delivery directly into a desired location (e.g., a wound). The nanofiber segments and/or nanofiber microspheres also may be delivered directly into a cavity (such as the peritoneal cavity) using a pressurized cannula.

In accordance with the instant invention, the nanofiber segments and/or nanofiber microspheres of the present invention can be used to treat and/or prevent a variety of diseases and disorders. Examples of diseases and/or disorders include but are not limited to wounds, ulcers, infections, hemorrhage, tissue injury, tissue defects, tissue damage, bone fractures, bone degeneration, cancer (e.g., the use of docetaxel and curcumin for the treatment of colorectal cancer (Fan, et al., Sci. Rep. (2016) 6:28373)), neurologic diseases (e.g., Alzheimer's and Parkinson's), ischemic diseases, inflammatory diseases and disorders, heart disease, myocardial infarction, and stroke. Methods for inducing and/or improving/enhancing wound healing in a subject are also encompassed by the instant invention. Methods of inducing and/or improving/enhancing tissue regeneration (e.g., blood vessel growth, neural tissue regeneration, and bone regeneration) in a subject are also encompassed by the instant invention. Methods of inducing and/or improving/enhancing hemostasis in a subject are also encompassed by the instant invention. The methods of the instant invention comprise administering or applying nanofiber segments and/or a nanofiber microsphere of the instant invention to the subject (e.g., at or in a wound). In a particular embodiment, the method comprises administering nanofiber segments and/or a nanofiber microsphere comprising an agent and/or cell as described herein. Nanofiber segments and/or nanofiber microspheres of the instant invention can be loaded with different cell types as necessary for regeneration of various tissues. In a particular embodiment, the nanofiber segments and/or nanofiber microsphere comprises blood clotting factors (e.g., for accelerating blood clot formation and/or preventing blood loss). In a particular embodiment, the method comprises administering nanofiber segments and/or a nanofiber microsphere to the subject and an agent as described herein (i.e., the agent is not contained within the nanofiber microsphere). When administered separately, the nanofiber microsphere may be administered simultaneously and/or sequentially with the agent. The methods may comprise the administration of one or more nanofiber segments and/or nanofiber microsphere. When more than one nanofiber microsphere is administered, the nanofiber microspheres may be administered simultaneously and/or sequentially.

The nanofiber segments and/or nanofiber microspheres can also be used to expand and increase cell numbers (e.g., stem cell numbers) in culture. In a particular embodiment, microtissues can be grown in situ by prolonged culture of cell laden nanofiber microspheres (e.g., in confined microfluidic channel devices). These microtissues are injectable or transplantable into a tissue defect to promote wound healing in a subject (e.g., the nanofiber microspheres comprise autologous cells).

The nanofiber segments and/or nanofiber microspheres may also be employed for cell detection, separation, and/or isolation of cell populations in a mixture. For example, microspheres conjugated to specific antibodies can be used for the isolation, separation, and/or expansion of different cell types from their mixtures (Custodio, et al., Biomaterials (2015) 43:23-31). Further, nanofiber microspheres can be used for the in vitro adhesion, proliferation, and/or maturation of chondrocytes as well as in vivo cartilage formation and osteochondral repair induced by nanofiber microspheres when injected together with chondrocytes (Liu, et al., Nat. Mater. (2011) 10:398-406).

The nanofiber segments and/or nanofiber microspheres of the present invention may be administered by any method. The nanofiber segments and/or nanofiber microspheres described herein will generally be administered to a subject or a patient as a pharmaceutical composition. The compositions of the instant invention comprise nanofiber segments and/or nanofiber microsphere and a pharmaceutically acceptable carrier. The term "patient" as used herein refers to human or animal subjects. These compositions may be employed therapeutically, under the guidance of a physician.

The compositions of the instant invention may be conveniently formulated for administration with any pharmaceutically acceptable carrier(s). For example, the agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the nanofiber segments and/or nanofiber microspheres in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

Compositions of the instant invention may be administered by any method. For example, the compositions of the instant invention can be administered, without limitation, parenterally, subcutaneously, orally, topically (ex. using a cream or spray), pulmonarily, rectally, vaginally, intravenously, intraperitoneally, intrathecally, intracerbrally, epidurally, intramuscularly, intradermally, intratumoral, intracarotidly, or by direct injection (e.g., a localized injection into a specific tissue or organ). Selection of a suitable pharmaceutical preparation will also depend upon the mode of administration chosen. For example, the compositions of the invention may be administered parenterally. In this instance, a pharmaceutical preparation comprises the nanofiber segments and/or nanofiber microspheres dispersed in a medium that is compatible with the parenteral injection. The nanofiber segments and/or nanofiber microspheres may be formulated in a variety of solutions and formats, such as, without limitation, a cream or ointment, a spray such as an aerosol, a powder, colloidal dispersion, emulsion, gels, and a liquid for injection or other form of administration.

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., parenterally.

In a particular embodiment, the nanofiber segments and/or nanofiber microspheres are delivered to a desired sight as a powder or liquid spray, aerosol spray, or a gel or cream. Delivery of the compositions may be performed using, without limitation, pump sprays, pump-atomizers, droppers, squeeze bottles, pressurized sprays, nebulizers, aerosolizes, and inhalers. The delivery device may be metered and/or deliver a unit dose. In a particular embodiment, the composition is delivered as an aerosol spray, e.g., using a pressurized container and a suitable propellant (e.g., a gas such as nitrogen, air, or carbon dioxide, or a fluid such as 1,1,1,2-tetrafluoroethane, 1,1,1,2,3,3,3-heptafluoropropane, dichlorodifluoromethane, trichlorofluoromethane, dichlorotetrafluoroethane, fluorocarbons, fluorinated chlorinated hydrocarbons, hydrochlorofluorocarbons, hydrochlorocarbons, hydrocarbon ethers, and hydrocarbons (e.g., n-butane, propane, isopentane, or a mixture thereof)).

Dry aerosol in the form of finely divided solid particles of compounds that are not dissolved or suspended in a liquid may be used. The compounds may be in the form of dusting powders and comprise finely divided particles having an average particle size of between about 1 and 5 microns, or between 2 and 3 microns. Finely divided particles may be prepared by pulverization and screen filtration using techniques well known in the art.

An aerosol formulation used for administration may be an aqueous solution. Antimicrobial agents, antiseptics, or preservatives can also be included in the formulation. The compositions of the instant invention may further comprise a stabilizer (e.g., water), solvent, dispersing agents, lubricants, etc. Aerosol formulations can also include other components, for example, ethanol, isopropanol, glycols, propylene glycol, as well as surfactants or other components such as oils and detergents. These aerosol components can serve to stabilize the formulation and lubricate valve components.

In a particular embodiment of the instant invention, methods for modulating (increasing) hemostasis; inhibiting blood loss; and/or treating hemorrhage are provided. In a particular embodiment, the method comprises administering the nanofiber segments and/or nanofiber microspheres to the wound or site of bleeding. In a particular embodiment, the nanofiber segments and/or nanofiber microspheres comprise a blood clotting factor such as thrombin and/or fibrinogen. In a particular embodiment, the nanofiber segments and/or nanofiber microspheres are contained in an aerosol device. In a particular embodiment, the nanofiber segments and/or nanofiber microspheres are sprayed (e.g., an aerosol spray) onto the wound or site of bleeding.

In a particular embodiment of the instant invention, methods for stimulating bone regeneration and/or treating bone loss are provided. In a particular embodiment, the method comprises administering the nanofiber segments and/or nanofiber microspheres to the site of bone loss. In a particular embodiment, the site of bone loss is periodontal. In a particular embodiment, the nanofiber segments and/or nanofiber microspheres are mineralized. In a particular embodiment, the nanofiber segments and/or nanofiber microspheres comprise a bone growth stimulating growth factor such as a bone morphogenic protein or fragment or analog thereof. In a particular embodiment, the agent is a bone morphogenetic protein (e.g., BMP-2, BMP-7, BMP-12, BMP-9; particularly human; particularly BMP-2 fragments, peptides, and/or analogs thereof). In a particular embodiment, the agent is a BMP-2 peptide such as KIPKASSVPTELSAISTLYL (SEQ ID NO: 1). In a particular embodiment, the agent is a BMP-2 fragment (e.g., up to about 25, about 30, about 35, about 40, about 45, about 50 amino acids, or more of BMP-2) comprising the knuckle epitope (e.g., amino acids 73-92 of BMP-2 or SEQ ID NO: 1). In a particular embodiment, the BMP-2 peptide is linked to a peptide of acidic amino acids (e.g., Asp and/or Glu; particularly about 3-10 or 5-10 amino acids such as E7, E8, D7, D8) and/or bisphosphonate (e.g., at the N-terminus).

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, an "anti-inflammatory agent" refers to compounds for the treatment or inhibition of inflammation. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 2,000). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. A "photocrosslinker" refers to a molecule capable of forming a covalent linkage between compounds after photoinduction (e.g., exposure to electromagnetic radiation in the visible and near-visible range). Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent.

The following examples illustrate certain embodiments of the invention. They are not intended to limit the invention in any way.

EXAMPLE 1

Materials and Methods
Materials

PCL ($M_w$=80,000 and 45,000; Sigma), type A gelatin from porcine skin (300 g Bloom; Sigma), poly-lactic-co-glycolic acid (PLGA with 50:50 ratio of lactic acid-glycolic acid and ester-terminated, $M_w \approx$30,000-50,000 from LACTEL absorbable polymers), sodium alginate (Sigma), tetraethylene orthosilicate (Sigma), triethyl phosphate (Sigma), $Ca(NO_3)_2 \cdot 4H_2O$ (Sigma), and glutaraldehyde (GA) (alcoholic solution).

Fabrication of Electrospun Polymeric and Bioactive Glass Fibers

Electrospinning was employed to fabricate NFs of various compositions. The following compositions of NFs were electrospun for the present study: (i) PCL-gelatin in 1:1 ratio; (ii) poly-lactic-co-glycolic acid (PLGA with 50:50 monomer ratio)-type A gelatin in 1:1 ratio; (iii) poly-lactic-co-glycolic acid (PLGA with 50:50 monomer ratio)-type A gelatin in 3:1 ratio; and (iv) bioactive glass (Ca/P/Si) fibers. The PCL-gelatin and PLGA-gelatin electrospinning solutions were prepared by dissolving pre-estimated amounts of the polymers in hexafluoroisopropanol. The polymeric NFs were collected on a rotating mandrel at high and low speeds so as to obtain aligned and random NFs, respectively. The sol-gel-derived bioactive glass fibers were fabricated (Weng, et al., ACS Appl. Mater. Interfaces (2017) 9:24484-24496). The typical electrospinning parameters were as follows: dc voltage=15 kV, flow rate=0.4-0.6 mL/hour, and distance between the spinneret to collector=10-15 cm. The polymer fibers were cross-linked by GA vapors from a 25% ethanolic solution overnight for ~24 hours.

Preparation of Segmented/Homogenized Short Electrospun Fibers from Nanofiber Mats The cross-linked polymeric nanofiber mats were weighed for dispersion into water at predetermined concentrations. The weighed nanofiber mats were segmented and/or homogenized using a cryostat and/or an ultrasonic homogenizer, respectively. In the former case, the nanofiber mats were frozen in water at −80° C. and then cryocut at −20° C. with cutting thicknesses set to 30 and 50 µm to segment the aligned PCL-gelatin NFs. In the latter case, the random nanofiber mats were scissored into tiny bits and then homogenized with a 20 kHz probe sonicator (Qsonica 500) equipped with a ⅛ in. tapered microtip probe under ice-cold conditions for 20 minute using on/off cycles of 10/20 seconds and 20% amplitude. The aqueous dispersions of short fibers were subsequently used for electrospraying. For the inorganic bioactive glass fibers too, a similar homogenization protocol was followed.

Electrospraying of Segmented/Homogenized Nanofiber Dispersions

All of the electrospraying experiments were performed in the dripping mode using aqueous short nanofiber dispersions and aluminum (Al) foil immersed in liquid nitrogen as the ground collector for the particles. For the fabrication of nanofiber microspheres, the fiber mats were typically dispersed in a nonsolvent such as water at a concentration of 20 mg/mL, whereas this was halved to 10 mg/mL for preparing porous nanofiber microspheres. The typical electrospray parameters used were as follows: voltage=8-10 kV, flow rate=2.0 mL/hour, and distance between the needle tip to collector/grounded electrode=10 cm. The 21G syringe needle with a nozzle diameter of 0.8 mm was used for all electrospraying experiments except for the coaxial electrospray. For the core-shell electrospray, the 20G needle with nozzle diameter of 0.902 mm was used as the outer needle and 27G with nozzle diameter of 0.4 mm was used for the inner needle and the two were indigenously connected with a Y-shaped tube to form a coaxial needle. For the core-shell microspheres, coaxial electrospraying was performed using dodecane as the core solvent at a flow rate of 0.4 mL/hour, whereas the shell flow rate was maintained at 2.0 mL/hour. After the electrospray microdripping, the frozen nanofiber microspheres were immediately transferred to a freeze dryer and lyophilized for 24 hours. Subsequently, the nanofiber microspheres were thermally treated at 50° C. for 48 hours to mechanically strengthen the particles. The core-shell microspheres were frozen and cryocut to confirm the hollow structure of the microspheres.

For the fabrication of solid microspheres, 5 wt % of lower molecular weight PCL ($M_w$=45 000) dissolved in dichloromethane was electrosprayed into an aqueous solution of 0.5 (v/v) % Tween 20 and 5 wt % gelatin. The electrospray parameters used were as follows: v=7.5 kV, flow rate=2.0 mL/hour, and distance between the needle tip to collector of 20 cm. The aqueous solution was agitated by continuous stirring to prevent agglomeration of the particles. The collected PCL-gelatin microparticles were freeze-dried and crosslinked using GA vapors for 24 hours.

Characterization of Microspheres

The morphology and particle size distribution of the microspheres were characterized by scanning electron microscopy (SEM) (FEI Quanta 200). The microspheres collected on Al foil were mounted onto a metallic stub using double-sided conductive carbon tape. The electrosprayed particles were sputter-coated in Ar atmosphere with an Au—Pd target at a peak current of 15 µA for 5 minutes. The microspheres were subsequently imaged in the secondary electron mode using an accelerating voltage of 20-25 kV. The particle size distribution was determined using ImageJ software by the analysis of ~50 microspheres per sample group. For the core-shell electrosprayed microspheres, the particles were cryosectioned with a thickness of 20 µm to demonstrate their hollow morphology. The autofluorescence of the cross-linked polymeric NFs was utilized to image the microspheres with a fluorescence microscope (Zeiss).

The bulk density of the electrosprayed microspheres with different morphologies was determined by transferring a known weight of the microspheres into a volume-calibrated Falcon 15 mL conical centrifuge tube. This was followed by gentle tapping until the microspheres are settled down at the bottom and finally the volume occupied by the microspheres was measured.

Cell Culture Studies with Rat Bone Marrow Derived Mesenchymal Stem Cells

For the cell culture experiments, mesenchymal stem cells were isolated from the bone marrow of rat femur and tibia. The protocol for the isolation of rat bone marrow-derived mesenchymal stem cells (rBMMSCs) was similar to that reported for isolation from mice (Huang, et al., J. Orthop. Translat. (2015) 3:26-33). Briefly, the hindlimbs of 12 week old rats euthanized by $CO_2$ asphyxiation were shaved to remove the animal hair and soaked in ethanol for 5 minutes. The skin and underlying fat tissue were cut open and scraped until neat bone samples were obtained. The rat bones were cut and washed in phosphate buffer saline (PBS) containing 1% antibiotic. Subsequently, a 23G needle was inserted into the bone marrow cavity and the rat bones were perfused with sterile low-glucose Dulbecco's modified Eagle's medium (DMEM) (Gibco) supplemented with 10% fetal bovine serum (FBS). The rBMMSCs were separated from the hematopoietic cells by their nonadherence to the cell culture polystyrene dish. The isolated rBMMSCs were maintained at 37° C. and 5% $CO_2$ in an incubator and cultured in a complete DMEM supplemented with 10% FBS as above for the cell adhesion experiments.

For the cell adhesion and proliferation experiments, equal weights (~2 mg) of the solid and nanofiber PCL-gelatin (1:1) microspheres were sterilized by soaking in absolute ethanol overnight and UV exposure for 24 hours. The sterile microspheres were washed thrice in PBS and used for subsequent cell culture experiments. The cell adhesion and proliferation of rBMMSCs on the microspheres was determined by coculturing the microspheres with the rBMMSCs on agar-coated (0.1 wt %) 96-well plates. The microspheres were dispersed in complete DMEM and uniformly distributed in the wells of an agar-coated 96-well plate. As the cell culture experiments were being performed in static culture, a high seeding density of ~10,000 cells/well was used. After permitting cell adhesion for 24 hours, the microspheres were transferred to different agar-coated wells and cultured for different time intervals. At designated time points, the cocultures of microspheres and rBMMSCs were harvested and fixed for confocal microscopy and SEM.

At time intervals of 1, 4, and 7 days, the microspheres were harvested by centrifugation at 1000 rpm for 1 minute. The microspheres were washed thrice in PBS and the samples were fixed in 4% paraformaldehyde (PFA) at room temperature for 30 minutes. The fixed microspheres were washed thrice in PBS and immersed in a permeabilization and blocking buffer (1% bovine serum albumin and 0.1% triton in PBS) for 30 minutes. To stain the actin cytoskeleton, an appropriate dilution of the methanolic solution of Alexa Fluor 546 phalloidin (Invitrogen) in the blocking buffer was used and incubated with the fixed microspheres at room temperature in the dark for 30 minutes. The microspheres were washed with PBS and counterstained with 4',6-diamidino-2-phenylindole dihydrochloride (DAPI) for the nuclei. The images were acquired using a Zeiss LSM 800 with an Airyscan confocal microscope equipped with appropriate excitation and emission filters. Particularly, the z-stack images were orthogonally projected onto a single plane to determine the cell nuclei on each microsphere.

The rBMMSC-microsphere cocultures were harvested and fixed in 2% PFA-2% GA in PBS for 30 min at room temperature. The microspheres were subsequently washed thrice in PBS and dehydrated in a gradient alcohol series of 30, 50, 75, 95, and 100% ethanol. The dehydrated microspheres were mounted on an Al stub and sputter-coated as previously for imaging under a scanning electron microscope.

To test the injectability of cell-laden microspheres and form tissue constructs in situ, the cocultured nanofiber microspheres were injected into polydimethylsiloxane (PDMS) channels. The channels were created using a Sylgard 184 silicone elastomer kit (Dow Corning USA) with 21G needles (0.902 mm diameter) as templates. Briefly, the silicone elastomer and curing agent were mixed in a 10:1 volume ratio, respectively, degassed under vacuum to removal air bubbles, and poured onto a rectangular mold with three 21G needles as templates. PDMS was cured overnight at 60° C. in an oven. Subsequently, the needles were removed to generate channels of ~1 mm diameter.

For this experiment, a higher seeding density of $10^5$ cells/well was used and the nanofiber particles were cultured in a 0.1% agar-coated 96-well plate for 24 hours. Subsequently, the cell-laden nanofiber microspheres were injected into sterilized PDMS channels (~1 mm diameter) and cultured in the confined channels at 37° C., 5% $CO_2$ for 3 days. Post the culture duration, the samples were fixed in 4% PFA overnight at 4° C. The fixed samples were stained with Alexa Fluor phalloidin 546 and DAPI to visualize the actin cytoskeleton and nuclei, respectively. The images were acquired with the help of a Zeiss 710 confocal microscope.

Cell Culture Studies with Mouse Embryonic Stem Cells

Frozen stocks of CE3 mouse embryonic stem cells (mESCs) were obtained. The mESCs were revived and cultured in T25 culture flasks coated with a 0.1% gelatin solution (Sigma-Aldrich, St. Louis, Mo.) in the presence of 5 µL of 1000 U/mL leukemia inhibitory factor (LIF) (Invitrogen, Grand Island, N.Y.) and 10 µL of L-2-mercaptoethanol (β-ME) (Invitrogen, Grand Island, N.Y.) to maintain their undifferentiated state. The cells were cultured in complete media consisting of DMEM (Invitrogen) supplemented with 10% new born calf serum, 10% FBS (Invitrogen), and 1% (v/v) EmbryoMax nucleosides and passaged at a ratio of 1:5 every 2 days.

The CE3 mESC suspension was adjusted to $1\times10^6$ cells/mL for culture with the microspheres. The CE3 mESCs were cocultured with the nanofiber and solid microspheres in 0.1% agar (Sigma-Aldrich) solution-coated 100 mm Petri dishes for 3 days in the presence of LIF and β-ME. The undifferentiated CE3 mESCs were induced to form embryoid bodies (EBs) containing neural progenitor cells using the 4−/4+ retinoic acid treatment protocol (Xie, et al., Biomaterials (2009) 30:354-362). CE3 mESCs attached to the nanofiber and solid microspheres were cultured in 0.1% agar solution-coated 100 mm Petri dishes in complete media in the absence of LIF and β-ME for 4 days. Retinoic acid (Sigma-Aldrich) at 0.5 µM was then added to the complete media for the final 4 days of culture. The media were changed every other day during the 8 day process. After EB formation, three-to-five cell-attached nanofiber and solid microspheres were transferred to separate wells of a 24-well plate (Corning, Corning, N.Y.). To induce neural differentiation, 1 mL of neural basal media containing B27 supplement [Invitrogen, 1:50 (v/v)] was added to each well of a 24-well plate containing the EB-attached microspheres. The culture was continued for 14 days with periodic replenishment of the neural basal media supplemented with B27.

β-III-tubulin (Tuj1) is a well-reported neural cell-specific marker (Thrivikraman, et al., Biomaterials (2014) 35:6219-6235; Thrivikraman, et al., Biomaterials (2016) 77:26-43). Therefore, immunostaining was performed using Tuj1 primary antibody to decipher neural differentiation of mESCs.

After 14 days of EB coculture with the microspheres, the samples in each well of the 24-well plate were washed with 1 mL of PBS (Invitrogen) and then fixed for 30 minutes with 500 μL of 4% PFA. Then, the cells were permeabilized in 400 μL of 0.5% Triton-X in PBS for 10 minutes. The cells were blocked with 500 μL of 5% normal goat serum (Invitrogen) in PBS for 30 minutes and incubated with Tuj1 (1:200) primary antibody overnight at 4° C. After that each well was washed thrice with PBS at 5 minute interval. Appropriate secondary antibodies (1:300 dilution) were applied for 1 hour at room temperature and each well was washed thrice with PBS at 5 minute interval. Finally, each well was incubated with 500 μL of DAPI solution (1:2000) for 5 min and then washed thrice with PBS at 5 minute interval. The fluorescence images of the samples were acquired under a Zeiss 710 confocal microscope.

Statistical Analysis

All of the cell culture experiments were performed in multiple replicates (n=6) and the data shown are the mean±standard deviation of these experiments. The IBM SPSS software version 2.0 was used for performing the statistical analysis. For determining statistical significance, one way ANOVA with Tukey test was performed with a statistical significance set at $p<0.05$, where p is the probability that there is no significant difference between the means of the compared groups.

Results

FIG. 1 is a schematic summary of the fabrication of nanofiber microspheres from short fiber segments prepared by cryocutting and/or homogenization with a probe sonicator in a solvent (i.e., deionized water) that does not dissolve the fiber mat. The homogenized fiber dispersions were electrosprayed into liquid nitrogen in the dripping mode, followed by freeze-drying and thermal treatment to mechanically strengthen the microspheres. Finally, the microspheres were demonstrated for their utility as stem cell/progenitor cell carriers and their potential for the delivery of therapeutics.

Figure 2B:
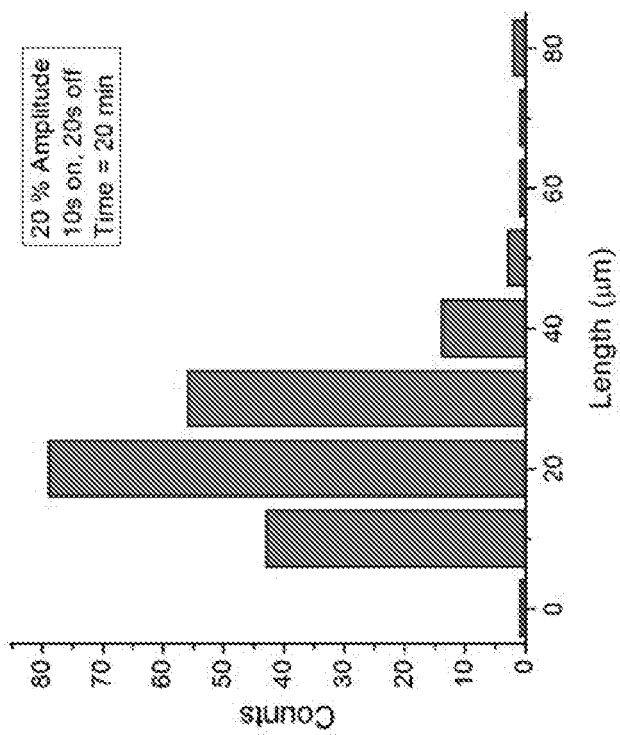
FIGS. 2A and 2B provide the morphology and size distribution, respectively, of PLGA-gelatin (1:1) electrospun NFs homogenized with a probe sonicator. Aligned PCL-gelatin (1:1) NFs segmented to lengths of 50 (FIG. 2C) and 30 μm (FIG. 2D) using a cryotome. The electrospun fibers upon cross-linking with glutaraldehyde (GA) vapors exhibit autofluorescence.
Figure 2A:
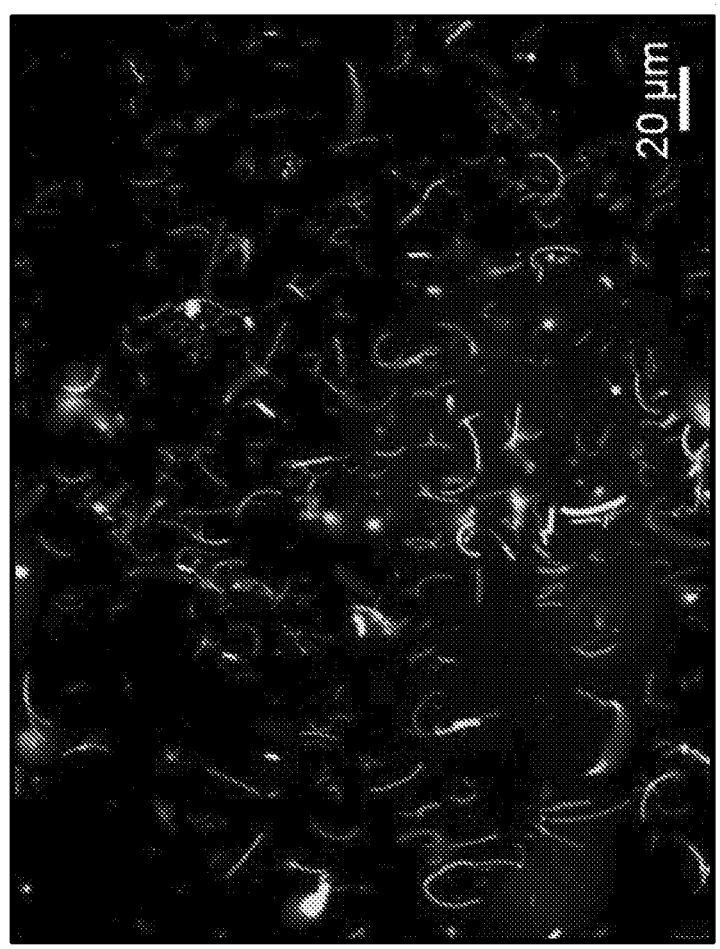
Figure 2D:
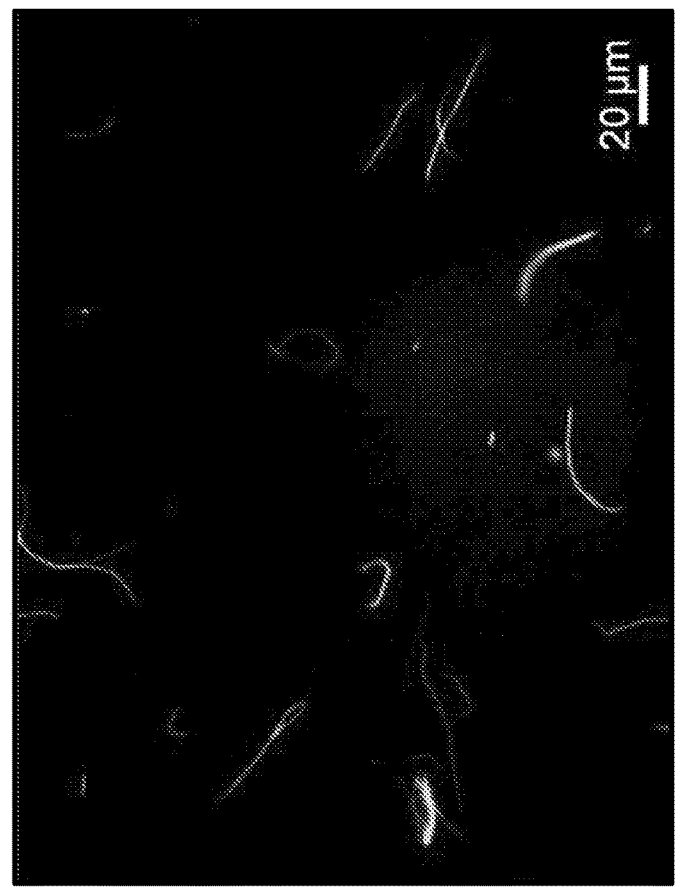
FIGS. 2E-2G provide SEM images of electrospun nanofiber segments: homogenized PLGA-gelatin (FIG. 2E), PCL-gelatin cryocut to 50 μm (FIG. 2F), and PCL-gelatin cryocut to 30 μm (FIG. 2G).
Figure 2C:
Figure 2E:
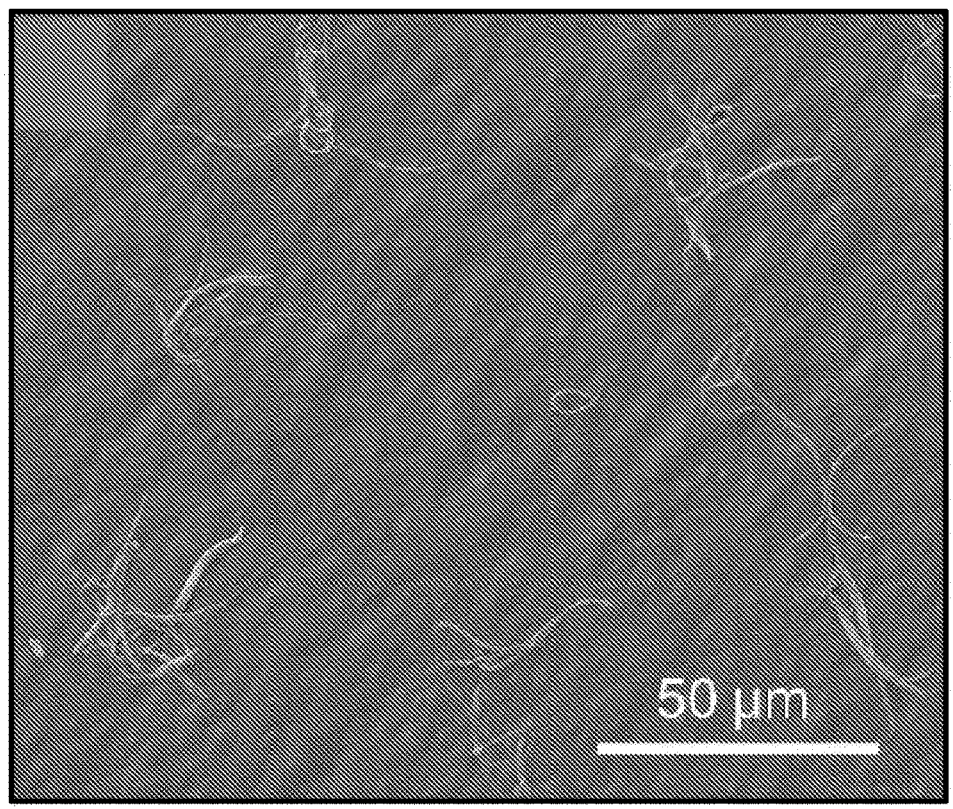
Figure 2F:
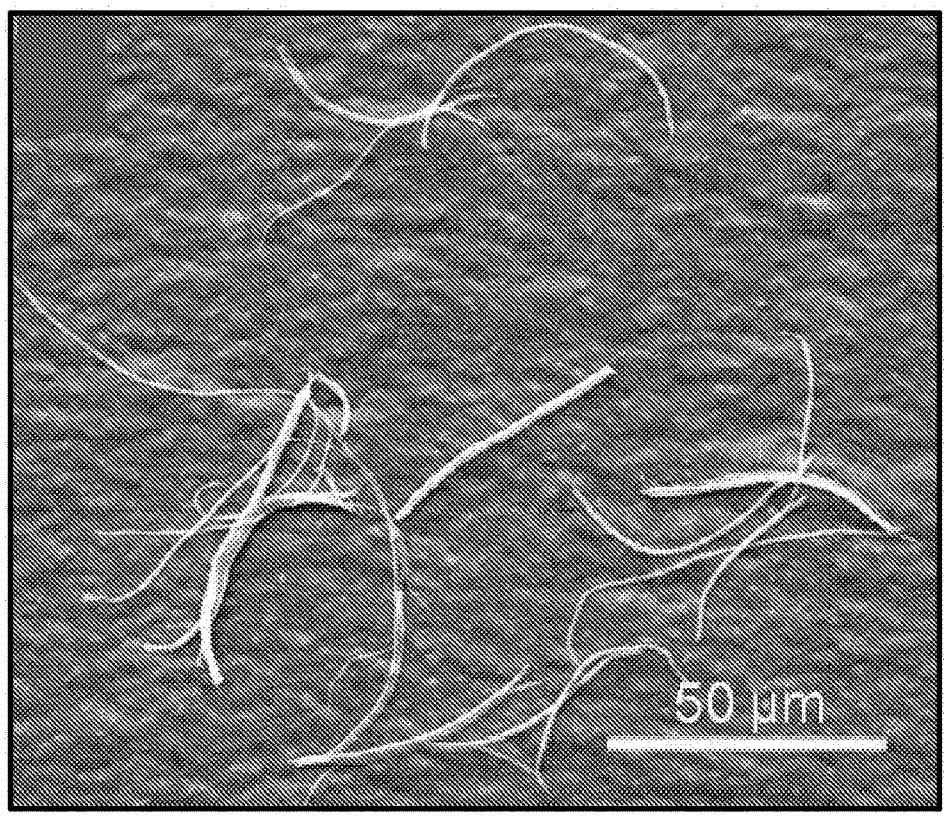
Figure 2G:
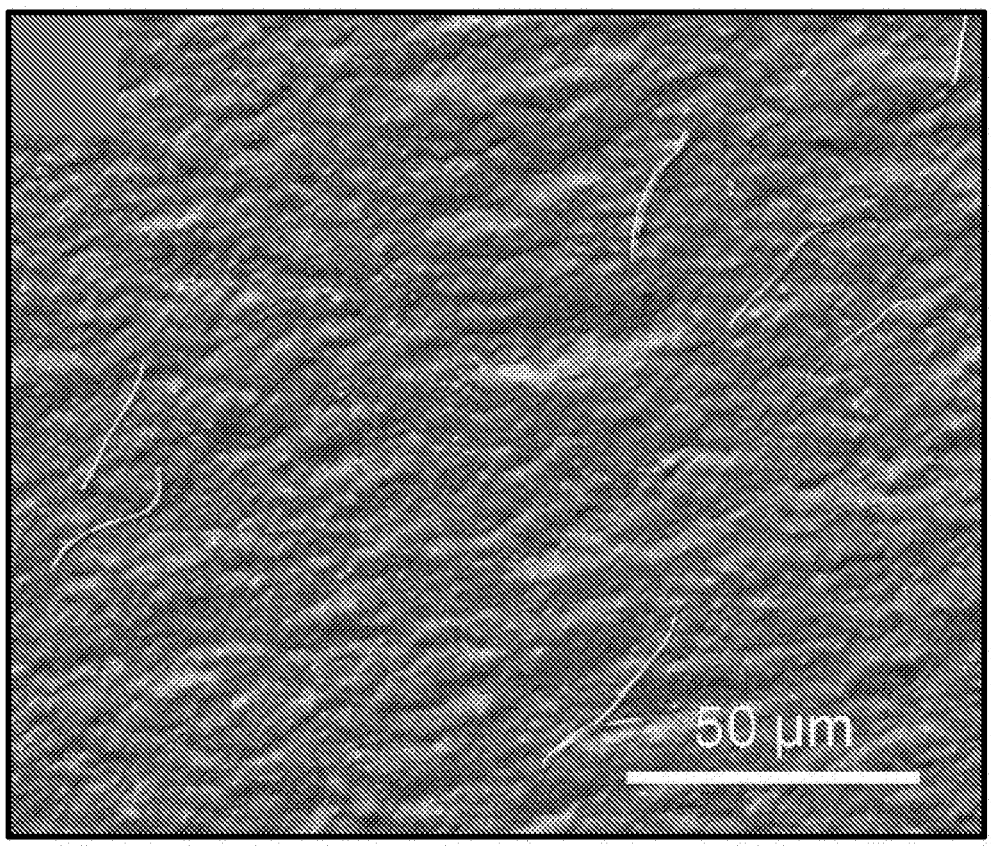

The short electrospun nanofiber segments were prepared by cryocutting and/or homogenizing with a probe sonicator. The segmented nanofiber dispersions were characterized by fluorescence microscopy and SEM. Typically, aligned PCL-gelatin nanofiber mats were cryocut to segments of 30 and 50 μm in length, whereas random fiber mats of PLGA-gelatin and bioactive glass fibers were homogenized using a probe sonicator. FIG. 2A shows fluorescence images corresponding to the homogenized PLGA-gelatin (1:1) short fibers. The length distribution of the nanofiber segments shown in FIG. 2B was obtained by measuring the fiber lengths of >250 fiber segments from 10 images. A median length of ~20 μm was discerned from the analysis of the short fiber segments under the homogenization conditions (20% amplitude, on/off cycles of 10/20 seconds each, and 20 minutes of sonication time) indicated. By manipulating the homogenization parameters such as amplitude, frequency, duration of on and off cycles, and sonication time, it is possible to control the median size of the homogenized short fibers. FIGS. 2C and 2D show the fiber segments of aligned PCL-gelatin (1:1) nanofiber cryocut to 50 and 30 μm, respectively. The minor variations in the lengths of cryocut fiber segments could be due to small misorientation of the supposedly aligned nanofiber mats. The rationale for using two different methods for the two polymer compositions lies in their glass-transition temperatures. The PLGA copolymers are glassy in nature and can be fragmented by homogenization because of their high glass-transition temperature, which is greater than the physiological body temperature of 37° C. (Makadia, et al., Polymers (2011) 3:1377-1397). On the other hand, PCL has been reported to possess a low glass-transition temperature of −50° C. and hence cannot be fragmented by homogenization because of its viscoelastic behavior even under ice-cold conditions (Tiptipakorn, et al., J. Appl. Polym. Sci. (2015) 132:41915). Therefore, the PCL-gelatin fibers were segmented into short fibers by cryocutting, followed by dispersing the cryocut segments by homogenization. FIGS. 2E-2G shows the scanning electron micrographs of homogenized PLGA-gelatin, PCL-gelatin cryocut to 50 μm, and PCL-gelatin cryocut to 30 μm lengths, respectively.

Figure 3A:
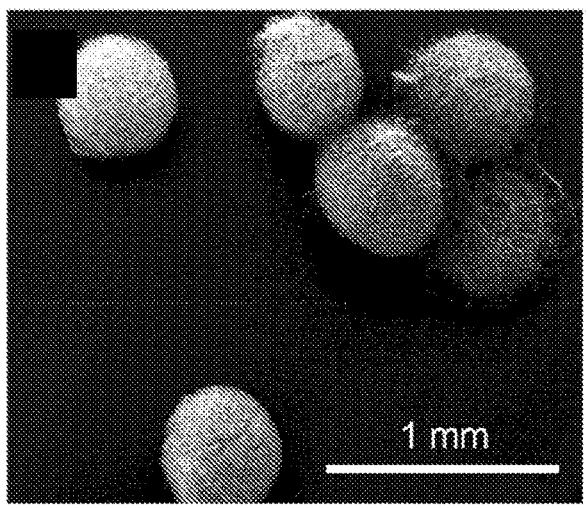
FIGS. 3A-3F provide SEM images of microspheres.
Figure 3B:
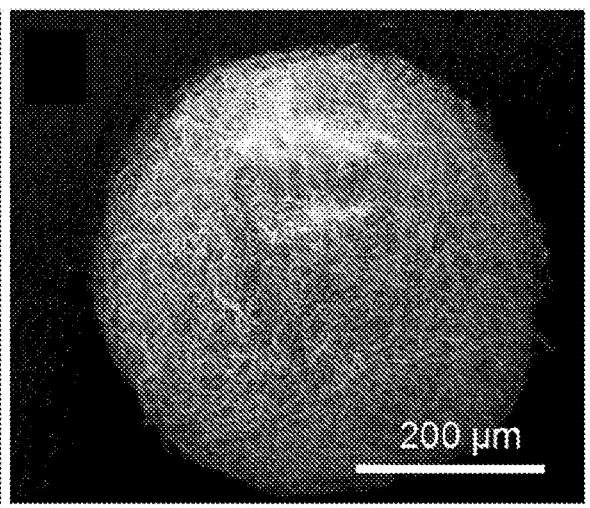
Figure 3C:
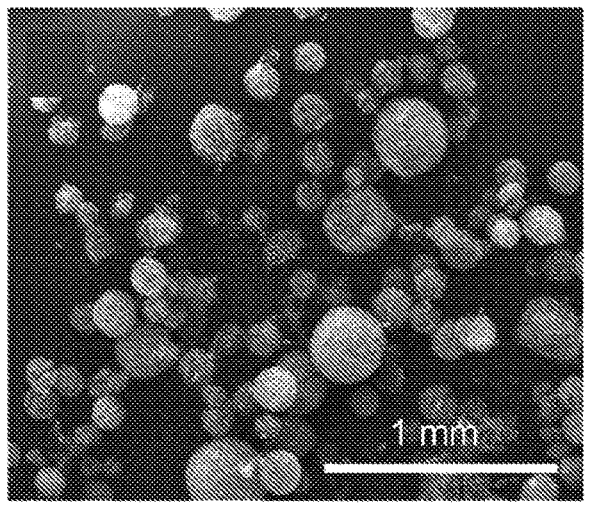
Figure 3D:
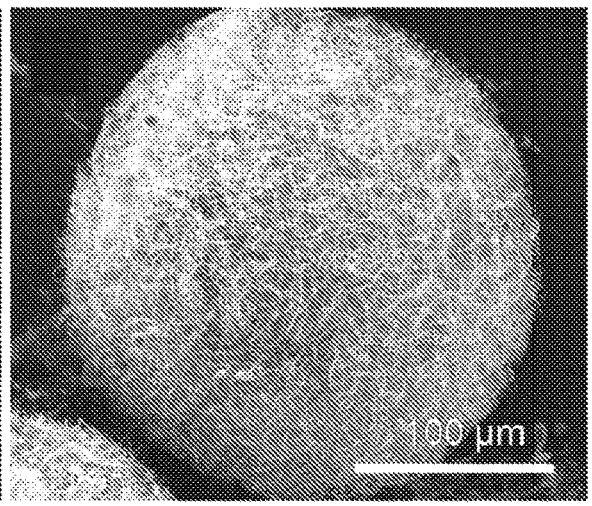
Figure 3E:
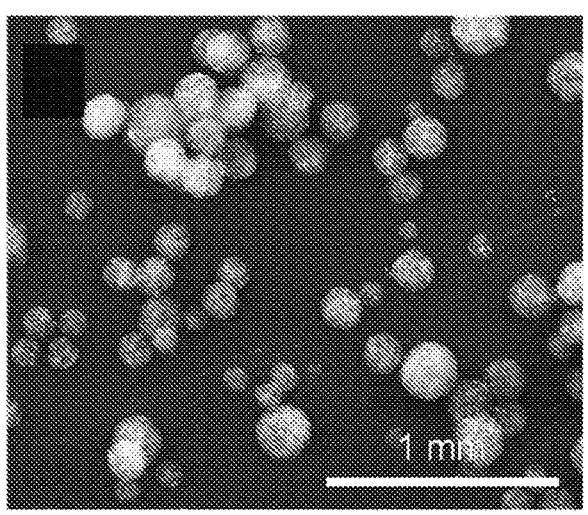
Figure 3F:
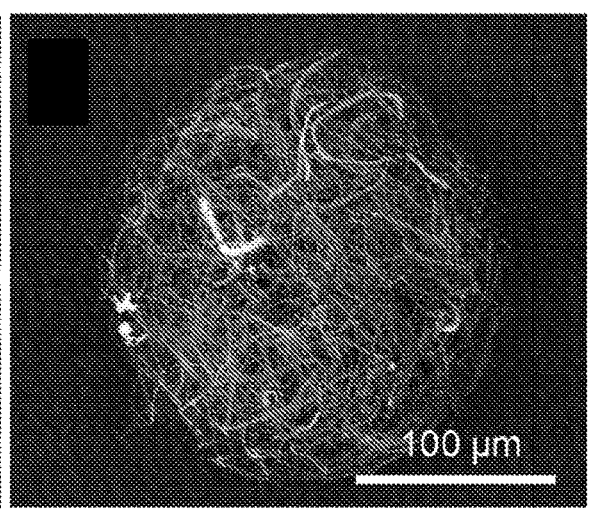
Figure 3G:
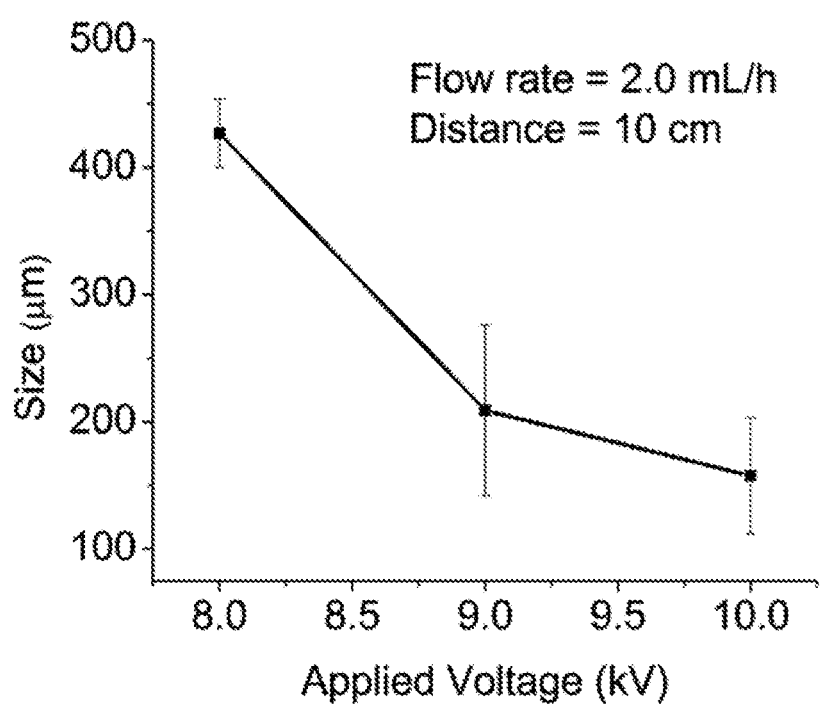
FIG. 3G provides the variation in the particle size of PCL-gelatin (1:1) nanofiber microspheres as a function of applied voltage [8 kV (FIGS. 3A and 3B); 9 kV (FIGS. 3C and 3D); and 10 kV (FIGS. 3E and 3F)] at fixed flow rate and distance between the needle tip and the collector.

The morphologies and size distribution of the different microspheres fabricated by electrospraying were measured by SEM and fluorescence microscopy. On the basis of the established theory and experimental data showing that the particle size can be manipulated by varying the electrospray processing parameters such as applied voltage and flow rate (Xie, et al., J. Colloid Interface Sci. (2006) 302:103-112; Xie, et al., Biomaterials (2006) 27:3321-3332; Boda, et al., J. Aerosol Sci. (2018) 125:164-181), in the current study, the voltage was varied between 8 and 10 kV at a fixed flow rate of 2.0 mL/hour to fabricate nanofiber microspheres of different sizes. FIG. 3 shows the morphology and size distribution of nanofiber PCL-gelatin (1:1) nanofiber microspheres. From the SEM images in FIGS. 3A and 3B, it can be observed that the particle size was more uniform between 400 and 450 μm along with a narrow size distribution of the microspheres at a lower voltage of 8 kV. This can be rationalized in that lower voltages facilitate larger and uniform droplet formation during electrospray in the dripping mode. Upon further increasing the direct current voltage to 9 kV, smaller droplets are formed, leading to smaller size of the microspheres with a rather broad size distribution ranging from 150 to 275 μm (FIGS. 3C and 3D). Further increase in the applied voltage to 10 kV did not significantly reduce the microsphere size, which ranged from 125 to 200 μm. The broader size variation at higher voltage could possibly result from combination of dripping and unstable spraying of the nanofiber dispersions during electrospray. Sometimes, the clogging of the needle tip occurred because of the sedimentation of the nanofiber segments. At such times, the needle was changed and/or the nanofiber dispersion in the syringe was manually mixed. Although lower flow rates can reduce the particle size, it would reduce the yield of the nanofiber microspheres. On the other hand, higher flow rates caused greater aggregation of the microspheres, which distorted upon agitation to disperse them. Perhaps, a better engineering of the electrospray fabrication process can lead to the production of nanofiber microspheres with uniform size. Nevertheless, a biomimetic nanofiber surface topography can be seen for all of the microspheres and this is a more important factor from a tissue engineering perspective (Wang, et al., Mater. Today (2013) 16:229-241).

Figure 4A:
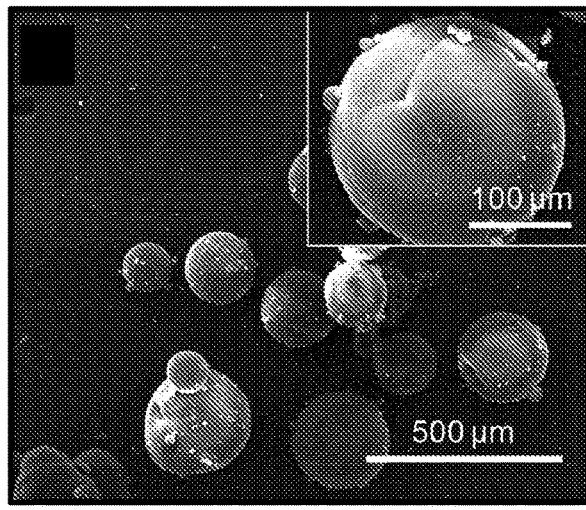
FIGS. 4A-4D provide images of different morphologies of PCL-gelatin (1:1) microspheres fabricated by electrospray microdripping: solid (FIG. 4A), nanofiber (FIG. 4B), porous nanofiber (FIG. 4C), and hollow nanofiber microspheres (FIG. 4D).

Apart from controlling the size distribution of the nanofiber microspheres, several morphologies of the microspheres could be achieved by electrospraying. FIG. 4 highlights the different microsphere morphologies fabricated by electrospraying in the current study. FIG. 4A corresponds to the regular solid PCL-gelatin microspheres. A lower molecular weight of PCL ($M_w$=45,000) was used to obtain microspheres with spherical morphology (Zhou, et al., Aerosol Sci. Technol. (2016) 50:1201-1215). However, it was difficult to obtain solid microspheres with uniform size ≥100 μm as electrospraying in the dripping mode resulted in microsphere aggregation, whereas the cone-jet spraying mode resulted in smaller size and broad size distribution.

Figure 4B:
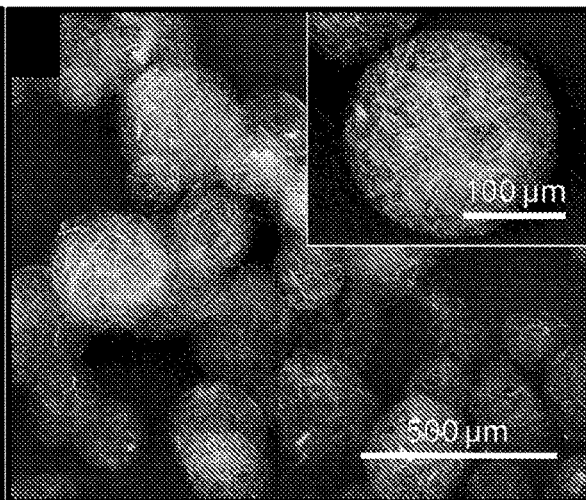
Figure 4C:
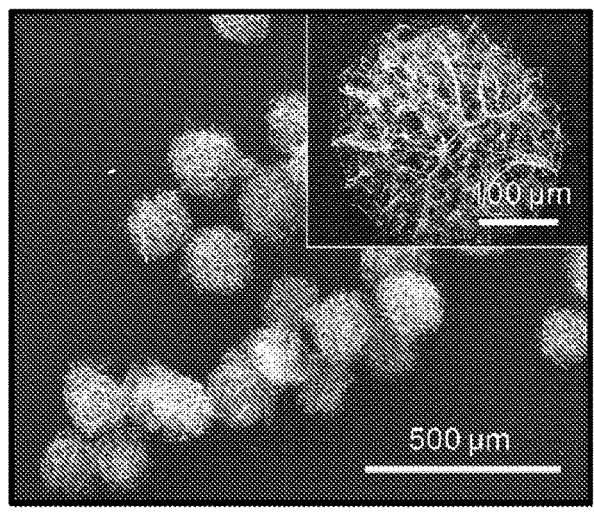
Figure 4D:
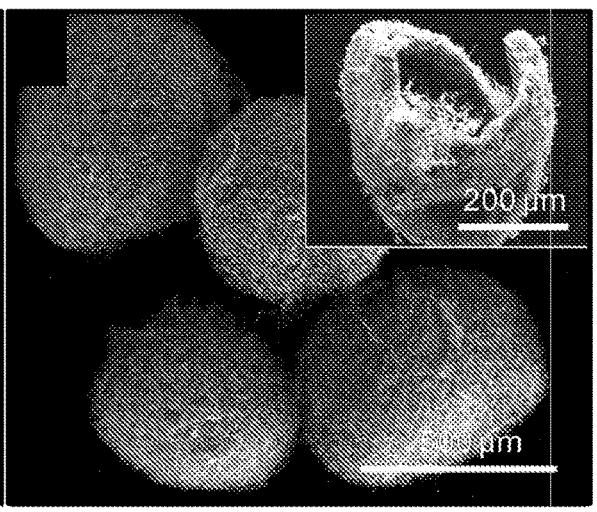

Therefore, the processing conditions chosen were at the border of the two electrospray modes. FIGS. 4B and 4C show the regular dense PCL-gelatin nanofiber microspheres and porous nanofiber microspheres fabricated with high and low fiber densities of 20 and 10 mg/mL, respectively. This is analogous to the PLGA concentration-dependent fabrication of uniform beads of PLGA with controllable pore size from a water-in-oil-in-water emulsion flowing through a microfluidic device (Choi, et al., Small (2010) 6:1492-1498). FIG. 4D denotes core-shell PCL-gelatin microspheres obtained by coaxial electrospray with a segmented PCL-gelatin shell and dodecane solvent as the core. A solvent immiscible with water and a freezing point above the freeze-drying temperature was necessary to prevent the collapse of the microspheres. Dodecane has a freezing/melting point of −10° C. and thus satisfied both requirements. The hollow structure of the core-shell microspheres was observed after cryosectioning the frozen spheres as shown in the inset of FIG. 4D. Depending on the flow rates of the core and sheath fluids, the shell thickness of the hollow microspheres can be controlled. Further, the needle gauges used for the coaxial electrospray were 20G (diameter of 0.902 mm) for the outer needle and 27G (diameter of 0.4 mm) for the inner needle. The large diameter of the outer needle led to larger-sized core-shell microspheres after coaxial electrospray. With regard to cell delivery, hollow nanofiber microspheres may exhibit better cell adhesion and proliferation as both the exterior and interior of the sphere are available for cell adhesion (Liu, et al., Nat. Mater. (2011) 10:398-406). However, the porous nanofiber microspheres may be more competent for cell delivery as they can permit greater cell infiltration, although their mechanical stability may not be sufficient for long-term cell culture.

Figure 5A:
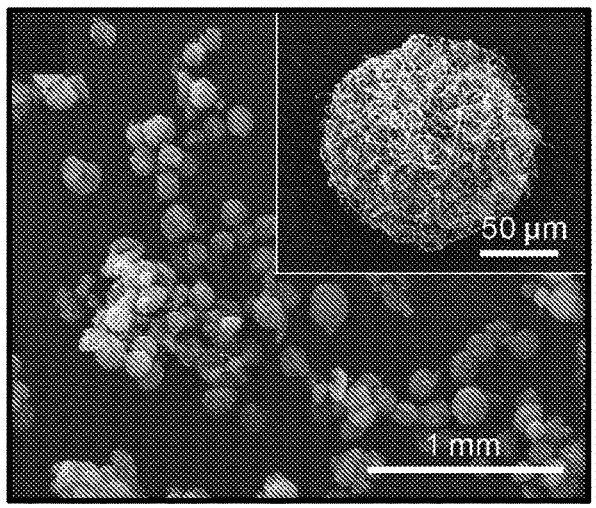
FIGS. 5A-5D provide images of different compositions of nanofiber microspheres fabricated by electrospray of nanofiber segments: PLGA-gelatin@1:1 (FIG. 5A), PLGA-gelatin@3:1 (FIG. 5B), PLGA NF@10 mg/mL in 0.25 wt % gelatin (FIG. 5C), and bioactive glass NF@10 mg/mL in 0.25 wt % alginate (FIG. 5D).
Figure 5B:
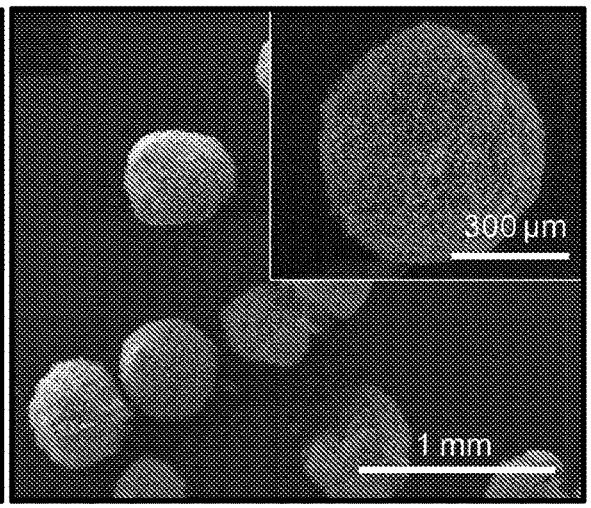
Figure 5C:
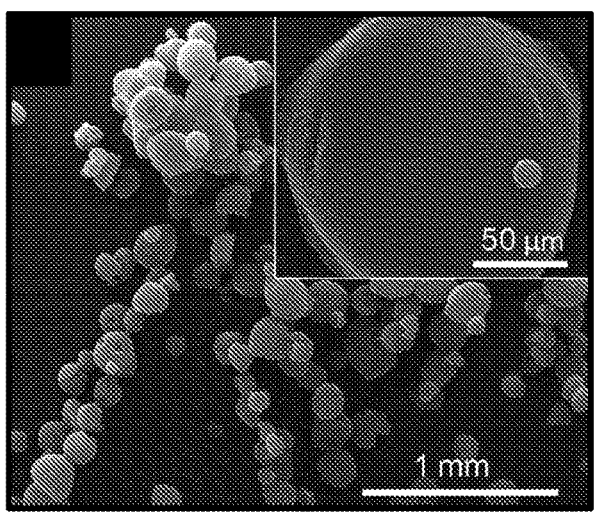
Figure 5D:
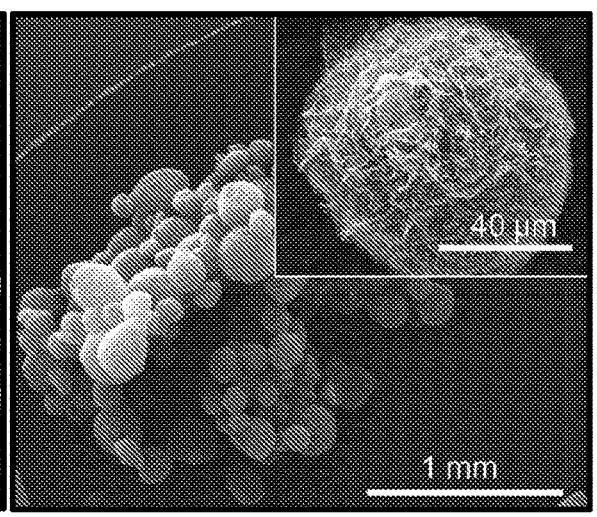

In addition to obtaining multiple particle morphologies, it was also possible to fabricate nanofiber microspheres from various organic polymer composite fibers as well as inorganic bioactive glass fibers. FIGS. 5A and 5B show the SEM images of nanofiber microspheres of PLGA-gelatin in 1:1 and 3:1 weight ratios, respectively. It was determined that it was desirable to have at least some gelatin to glue the nanofibers together during the electrospray of electrospun nanofiber segments. The mechanical stability of the nanofiber microspheres was greatest for the polymer-gelatin ratio of 1:1. To fabricate PLGA nanofiber microspheres, homogenized PLGA NFs at 10 mg/mL fiber concentration was mixed with 0.25 wt % of gelatin and electrosprayed (FIG. 5C). In a similar manner, homogenized bioactive glass at 10 mg/mL was dispersed in 0.25 wt % of alginate to fabricate bioactive glass nanofiber microspheres (FIG. 5D). Thus, it was demonstrated that a broad range of polymer compositions can be successfully used for the fabrication of nanofiber microspheres by electrospray microdripping of homogenized/segmented short fiber dispersions.

The bulk densities of the electrosprayed microspheres were calculated by measuring the volume occupied by a known weight of microspheres. Table 1 lists the bulk densities of the different microsphere morphologies fabricated by electrospraying. From the values listed in Table 1, a marked difference in the density of nanofiber microspheres and solid microspheres may be noted for both PCL-gelatin (1:1) and PLGA-gelatin (1:1) compositions. The nanofiber microspheres were 50 times lighter for the same volume occupied by the solid microspheres. This indicates the highly porous nature of the nanofiber microspheres as compared to the solid spheres. Further, the bulk densities of nanofiber microspheres were on the order of 5-10 mg/mL, which is similar to that recorded for cellulose nanofibril-derived aerogel microspheres fabricated by high-pressure spraying into liquid nitrogen (Cai, et al., Biomacromolecules (2014) 15:2540-2547). Among the nanofiber microspheres, no significant variation in the bulk densities of the hollow and porous nanofiber microspheres was noted. These porosity characteristics led to the selection of the solid and nanofiber microspheres for comparative cell culture study.

TABLE 1

Bulk Densities of Different Morphologies of Microspheres Fabricated by Electrospraying.

| | bulk density (±1.0) in mg/mL | |
|---|---|---|
| | PCL-gelatin (1:1) microspheres | PLGA-gelatin (1:1) microspheres |
| solid | 458.0 (±10.0) | 436.0 (±10.0) |
| NF | 11.2 | 9.2 |
| hollow NF | 8.6 | ND |
| porous NF | 8.0 | 6.4 |

Figure 6A:
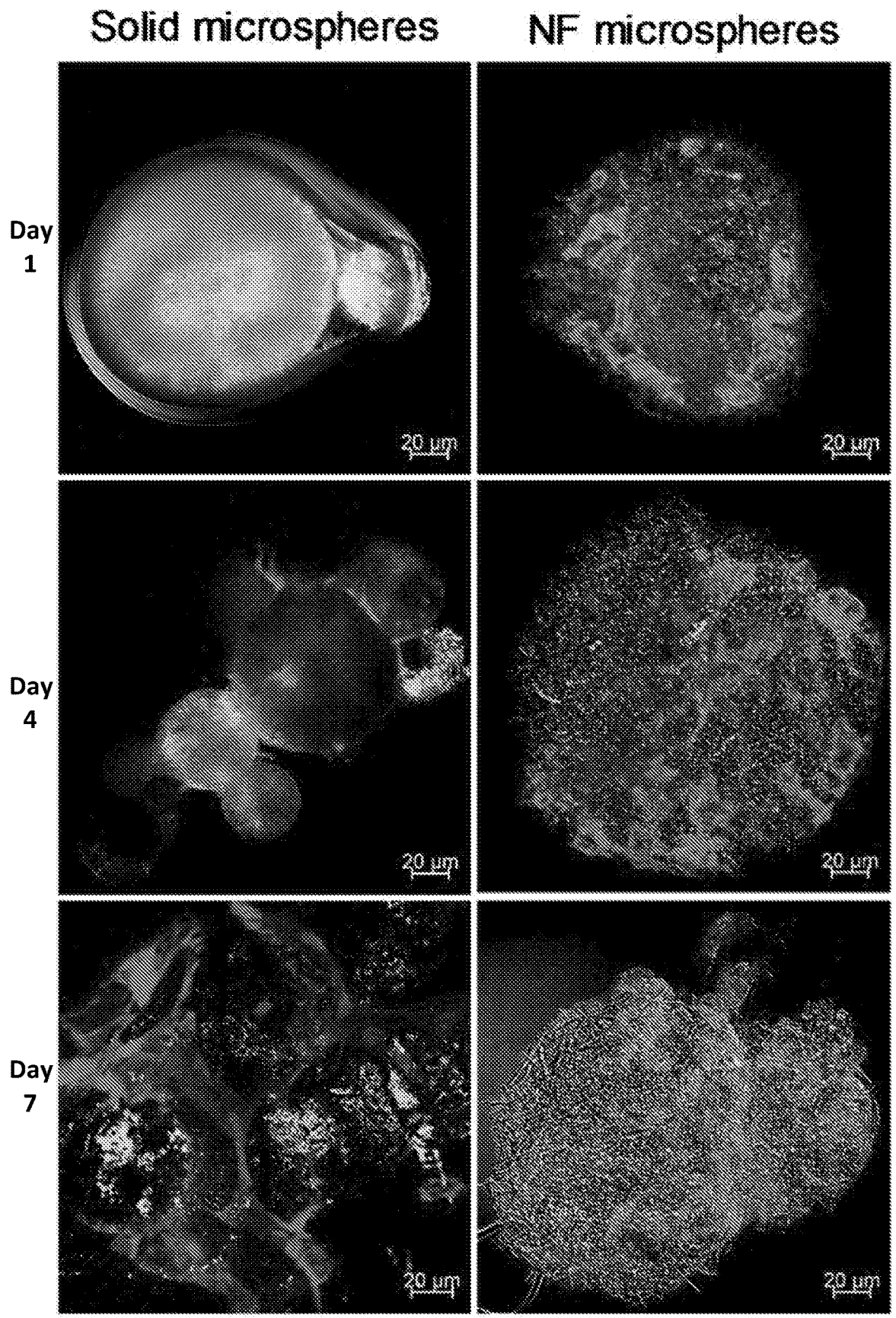
FIG. 6A provides comparative proliferation of rBMMSCs on PCL-gelatin (1:1) solid and nanofiber microspheres at the indicated days. The confocal images show cell cytoskeleton because of the staining of F-actin with Alexa Fluor phalloidin 546, nuclei because of DAPI, and the microspheres in the bright field transmitted light.
Figure 6B:
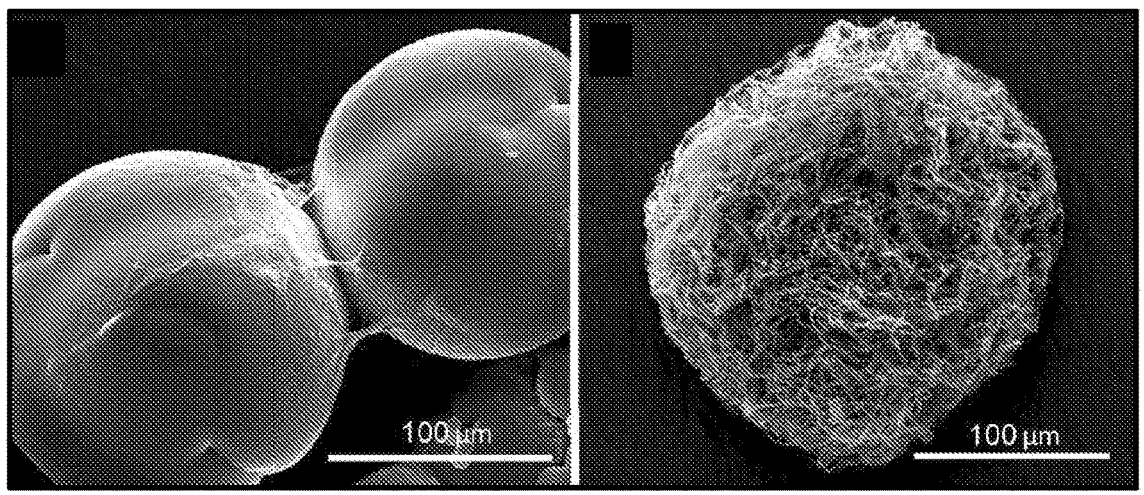
FIG. 6B provides SEM images showing the adhesion of rBMMSCs on solid microspheres (left) and nanofibrous microspheres (right) after 3 days of static culture.

The in vitro adhesion and proliferation of rBMMSCs was examined on nanofiber microspheres and compared with the solid microspheres. As anticipated, the extracellular matrix (ECM)-mimicking nature of the nanofiber microspheres promoted the initial cell adhesion as well as proliferation of rBMMSCs in comparison to the solid microspheres. From the cell morphologies on the nanofiber microspheres, it is evident that the adhered rBMMSCs were well spread on the 3D nanofiber topography as against the smooth surface presented by the solid microspheres. FIG. 6 presents representative confocal images showing the attachment and multiplication of rBMMSCs on solid and nanofiber microspheres at different time intervals under static culture. The statistics presented in FIG. 6A reveals a higher number of cell cargo per microsphere payload for the nanofiber microspheres as compared to the solid microspheres. Interestingly, the rBMMSCs seemed to prefer to occupy the voids or spaces between adjacent microspheres in the case of solid microspheres as shown in FIG. 6B.

Figure 6C:
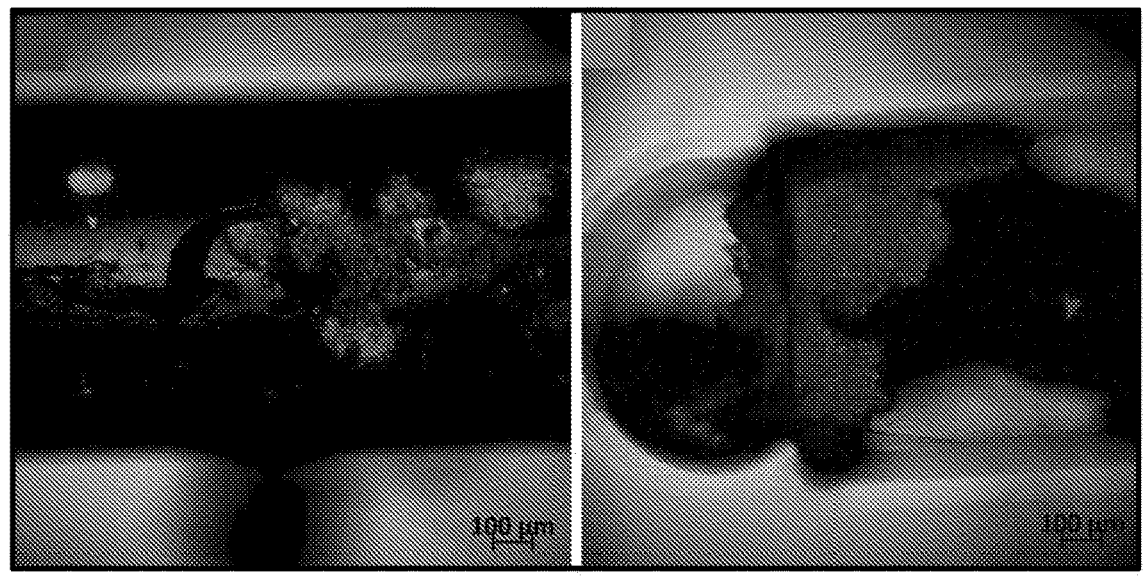
FIG. 6C provides images of rBMMSCs laden nanofibrous microsphere aggregates injected into PDMS channel and cultured for 3 days. Confocal images show actin cytoskeleton (Alexa Fluor Phalloidin 546) and nuclei (DAPI) in the microtissue-like structures in the middle (left) of the channel and at the end of the channel (right).
Figure 6D:
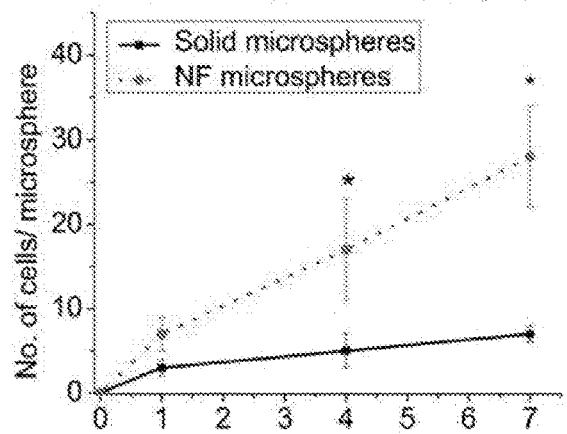
FIG. 6D provides cell proliferation data are mean±SD of cell nuclei counted from ≥15 microspheres per group per time point. * indicates statistically significant difference between the two groups with $p<0.05$, where p denotes that there is no significant difference between the compared means.

The cell (rBMMSCs)-laden nanofiber microspheres were injected into PDMS channels of ~1 mm diameter and cultured for 3 days. Because of the high cell seeding density and proliferation of the rBMMSCs, the injected microsphere aggregates led to the formation of in situ microtissue-like structures as shown in FIG. 6C. This demonstrates the injectability of the cell-laden nanofiber microspheres into irregular-shaped defects for eliciting tissue regeneration in a minimally invasive manner.

Figure 7A:
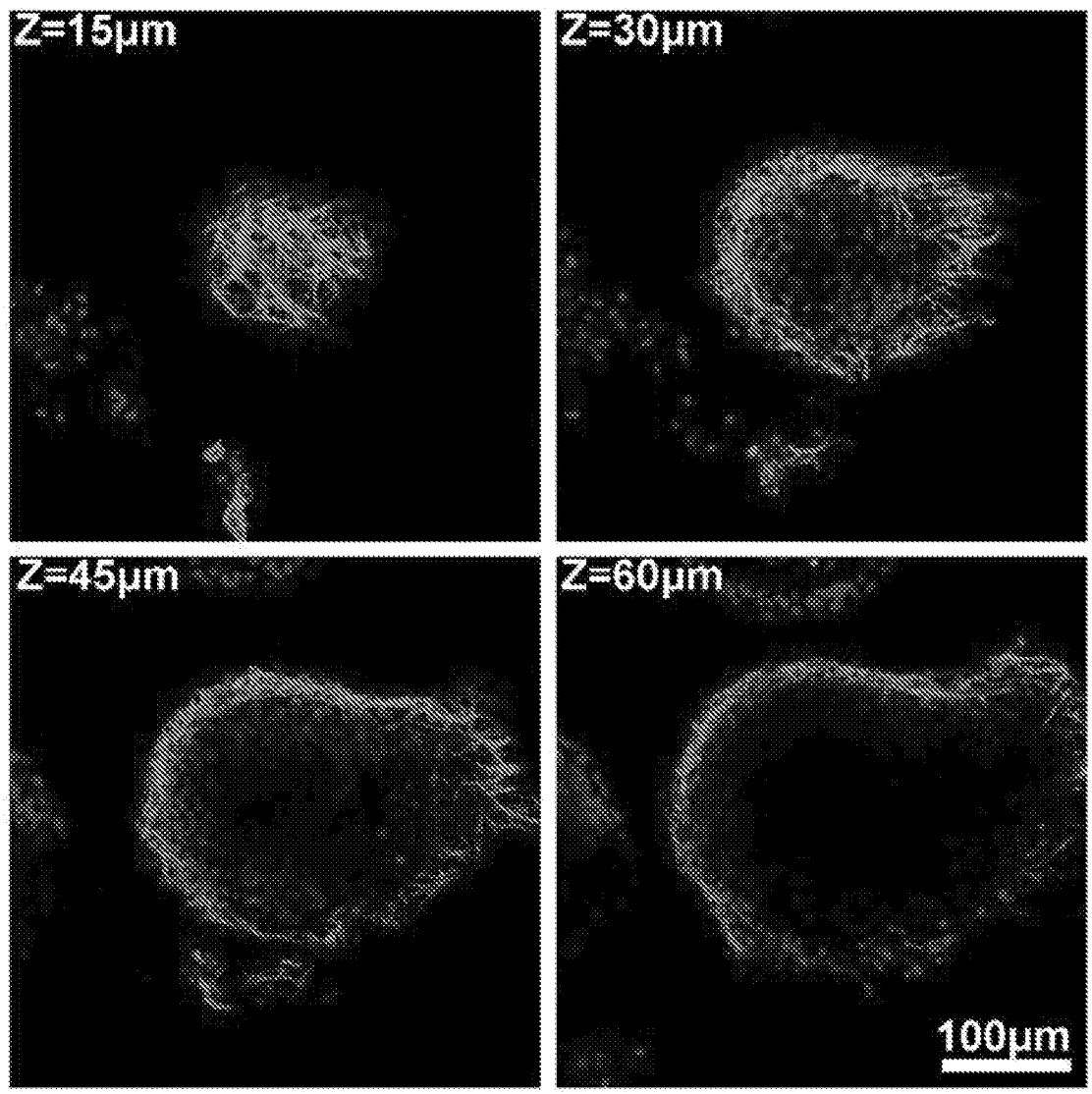
FIGS. 7A and 7B show neural differentiation of CE3 mESC on nanofiber (FIG. 7A) and solid microspheres (FIG. 7B). Confocal images show neural marker β-III-tubulin in deep red with the secondary antibody labeled with Alexa Fluor 647 and the nuclei with DAPI. The images shown in each case correspond to the frames captured at different z-stack focal planes (z=15, 30, 45, and 60 μm).
Figure 7B:
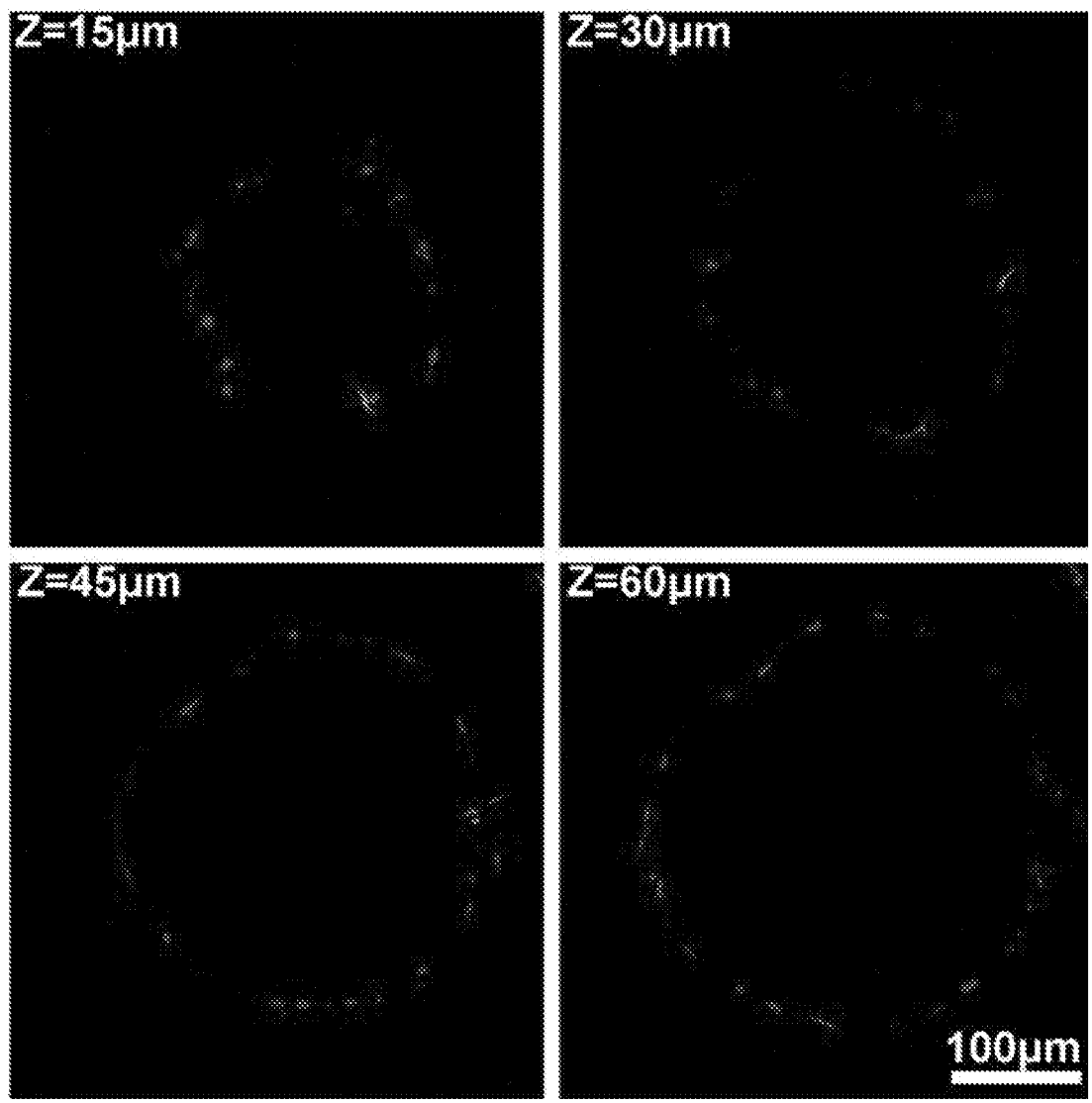

Aligned PCL 2D nanofiber mats facilitated the 4−/4+ retinoid acid protocol-induced neural differentiation of embryoid bodies prepared from similar CE3 mESCs (Xie, et al., Biomaterials (2009) 30:354-362). mESCs can neurally differentiate on nanofiber matrices (Callahan, et al., Biomaterials (2013) 34:9089-9095; Shahbazi, et al., Tissue Eng., Part A (2011) 17:3021-3031; Mahairaki, et al., Tissue Eng., Part A (2011) 17:855-863). The neural differentiation of mESCs on nanofiber matrices was ascertained by positive immunostaining for nestin and β-III-tubulin (Tuj1), reverse transcription polymerase chain reaction analysis of neural specific genes such of nestin, Tuj1, MAP2, SOX1, and PAX6, and electrophysiology experiments. Therefore, it was expected that the expression of neural marker genes would be consistent with positive Tuj1 staining. Hence, neural differentiation of mESCs was evaluated with Tuj1 as a neural marker. With this hindsight, the differentiation of mESCs to neural lineage was compared on both the solid and nanofiber microspheres. FIGS. 7A and 7B show the confocal images of the mESCs on the nanofiber and solid microspheres under neurogenic induction culture, respectively. The individual frames in FIGS. 7A and 7B show the confocal images captured at distances of 15, 30, 45, and 60 µm, in between the first and last frames of a recorded z-stack. Several neurite extensions with positive staining for Tuj1 (fluorescence arising from antibody conjugated to Alexa Fluor 647), a neural differentiation marker, can be seen in the case of nanofiber microspheres (FIG. 7A). On the contrary, the number of cells adhered on the solid microspheres was meagre with only few cells exhibiting neurite protrusions with positive Tuj1 staining (FIG. 7B). The higher cell adhesion of mESCs on nanofiber microspheres is consistent with the higher adhesion and proliferation of rBMMSCs on similar spheres.

Stem cell therapy holds great promise for the regeneration of tissue defects/injuries, autoimmune diseases, and neurodegenerative disorders (Trounson, et al., Cell Stem Cell (2015) 17:11-22). Although adult stem cells do not pose the risk of teratoma, immune rejection, and ethical issues, their isolation and expansion on two-dimensional (2D) polystyrene culture dishes different from their in vivo 3D niche environment weakens their paracrine functions and homing capability to the site of injury (McKee, et al., Colloids Surf., B (2017) 159:62-77). Further, the injection of the stem cells either systemically, intravenously, intraperitonially, or locally into the tissue defect results in poor survival, migration to other tissues/organs than the target site, and consequent disability to form 3D tissues (Liu, et al., Int. J. Mol. Sci. (2016) 17:982). This has necessitated the development of stem cell carriers in the form of injectable hydrogels and microspheres. In this light, the biomimetic nanofiber microspheres are perhaps the best choice as delivery vehicles for stem cells as their 3D nanofiber topography recapitulates the ECM niche of adult stem cells.

For geometric- and regular-shaped defects, it is advantageous to culture stem cells in 3D porous scaffolds with pore interconnectivity and transplant the cell-laden scaffold into the defect (Annabi, et al., Tissue Eng., Part B (2010) 16:371-383). Additionally, the nanofiber topography in 3D porous scaffolds can better mimic the ECM of native tissue. The nanofiber architecture of 3D hybrid porous nanofiber aerogels with bone ECM-like structure is crucial for neovascularization of the regenerated bone tissue in 8 mm rat calvarial defects. The fabrication of nanofiber aerogel microspheres for injectable stem cell therapy into irregular-shaped defects was demonstrated. The minimal invasiveness of the injectable nanofiber microspheres is superior compared to surgical implantation of 3D porous scaffolds for stem cell therapy-based tissue regeneration.

Different types of porous microspheres with surface pores and internal pores fabricated from a broad range of precursor polymers including PLGA, PLLA, chitosan, and PCL utilizing porogens of inorganic salts, gelatin, sugar, and so forth have been synthesized (Cai, et al., Int. J. Nanomed. (2013) 8:1111-1120). A water-in-oil-in-water emulsion generated by the combined flow of phases from three channels in the fluidic device was employed for the fabrication of PLGA microspheres with surface pores and hollow interior (Choi, et al., Adv. Funct. Mater. (2009) 19:2943-2949). Using a similar fluidic flow of the water-in-oil-in-water emulsion, uniform PLGA microspheres with controllable pore sizes were fabricated (Choi, et al., Small (2010) 6:1492-1498). In contrast, the fabrication of nanofiber microspheres has been limited to the self-assembly of ss-PLLA and phase separation of polyhydroxybutyrate and chitosan/chitin derivatives (Ma, et al., Tissue Eng., Part C (2017) 23:50-59; Zhou, et al., Nanoscale (2016) 8:309-317; Zhang, et al., Adv. Mater. (2015) 27:3947-3952). In this light, the current study demonstrates the fabrication of nanofiber microspheres with a broad variety of polymer compositions by electrospraying of homogenized electrospun fiber aqueous dispersions. The nanofiber microspheres fabricated in the current study were conducive for the culture of undifferentiated bone marrow stem cells as well as neuronally differentiated ESCs. Further, the aerogel nanofiber microspheres can form microtissue-like structures in situ, such as when injected into a PDMS microchannel.

The results provided herein indicate that the nanofiber microspheres can be applied as injectable scaffolds for stem cell-based tissue regeneration of irregular-shaped defects. Indeed, PCL-gelatin (1:1) nanofiber microspheres were used for the cell culture experiments and demonstrate the feasibility of using such particles as cell microcarriers. While the gelatin of these PCL-gelatin (1:1) nanofiber microspheres mat erode in the order of weeks (Hwang, et al., J. Biomed. Mater. Res., Part A (2016) 104:1017-1029), PCL degradation was not detected in PCL-gelatin nanofibers even after 90 days of incubation in PBS (Dulnik, et al., Polym. Degrad. Stab. (2016) 130:10-21). Nonetheless, depending on the regeneration of specific tissue types, the composition of the nanofiber microspheres can be tailored to adjust the degradation rate to match the tissue in growth. This study also demonstrated the fabrication of nanofiber microspheres with several compositions [e.g., PLGA-gelatin (1:1), PLGA-gelatin (3:1), and PLGA-collagen-gelatin (2:1:1)]. In addition, 3D nanofiber aerogels composed of PLGA-collagen-gelatin (2:1:1) were successfully applied for cranial bone regeneration in rats. Notably, the PLGA-collagen-gelatin (2:1:1) nanofiber aerogels underwent in vivo degradation within 4 weeks and were completely resorbed within 8 weeks.

Furthermore, the field of tissue engineering is currently undergoing a paradigm shift with regard to the treatment of tissue defects of irregular geometry and shape (Neves, et al., Expert Rev. Precis. Med. Drug Dev. (2016) 1:93-108). Minimally invasive injectable biomaterials coupled with stem cells/progenitor cells are preferred over painful surgeries that necessitate nominal postoperative treatment and care (Guelcher, S. A., Biocompatibility of Injectable Materials. In *Injectable Biomaterials*; Vernon, B., Ed.; Woodhead Publishing, 2011; Chapter 15, pp 354-374). This class of injectable biomaterials is largely composed of hydrogels and microspheres. Indeed, injectable biomaterial scaffolds have several advantages over preformed scaffolds with defined shape and geometry (Chang, et al., Mater. Sci. Eng., R (2017) 111:1-26). In particular, the application of injectable nanofiber microspheres has been demonstrated for promoting chondrocyte function in vitro and cartilage repair in vivo (Liu, et al., Nat. Mater. (2011) 10:398-406; Zhou, et al., Nanoscale (2016) 8:309-317). These studies show that the ECM-like physicochemical properties of the nanofiber microspheres elicit superior cartilaginous activity in chondrocytes, when compared to the solid microspheres. Synergistic BMP-2 release from heparin-conjugated gelatin solid nanospheres encapsulated within hierarchical PLLA nanofiber microspheres can be an effective osteoinductive scaffold for healing 5 mm calvarial defect in vivo (Ma, et al., Adv. Healthcare Mater. (2015) 4:2699-2708). Further, vascular endothelial growth factor release from heparin-conjugated gelatin solid nanospheres within PLLA nanofiber microspheres can promote dental pulp regeneration in human teeth, subcutaneously implanted in immunocompromised nude mice (Li, et al., Acta Biomater. (2016) 35:57-

67). Additionally, a two-stage delivery of DNA polyplexes encapsulated in PLGA nanospheres hierarchically embedded in nanofiber PLLA microspheres can be effective against pathogenic tissue fibrosis and aid in support disc regeneration (Feng, et al., Biomaterials (2017) 131:86-97). Thus, there are synergistic benefits with embedded solid nanospheres for therapeutic delivery within the ECM-mimicking topography of the nanofiber microspheres for tissue regeneration.

Although injectable microspheres have been largely implicated in cartilage and bone tissue engineering, they have other therapeutic applications including in neural and cardiac tissue regeneration. The nanofiber microspheres have been shown to be compatible with mESCs, which differentiated into neurons in the neural induction media. Such cell-laden, injectable nanofiber microspheres can be used to treat brain stroke, neurodegenerative diseases such as Alzheimer's and Parkinson's disease, and cardiac disorders such as scar tissue formation following myocardial infarction. All of the aforementioned diseases are characterized by ischemia-induced cell death. Therefore, the replenishment of ischemia/hypoxia preconditioned stem cells/progenitor cells at the ischemic locations can enhance their survival and lead to tissue regeneration (Yu, et al., Transl. Stroke Res. (2013) 4:76-88). To this end, the nanofiber microspheres in the current study have been demonstrated to be compatible cell carriers for different stem cell/progenitor cell types. Also, the current study is the first demonstration of combination of electrospray and electrospinning for fabrication of NF microspheres. The pore size of the nanofiber microspheres can be increased by controlling the freezing temperature during electrospraying of the nanofiber dispersions into microspheres. This can be achieved by using higher freezing temperatures that can generate larger pores in 3D nanofiber aerogels, which is also consistent with the established mechanism of ice crystal growth during freezing of organic-inorganic dispersions (Deville, et al., Science (2006) 311:515-518). Taken together, the nanofiber microspheres developed in the current study allow for better application of cell therapy in regenerative medicine.

The present study is the first report of fabrication of electrospun nanofiber microspheres using electrospray. As against previous methods of phase separation and self-assembly of polymers with specific surface chemistry, the instant approach of electrospraying of aqueous dispersions of short electrospun nanofiber segments into a cryocoolant can be applied to a broad range of polymer compositions, for different microsphere morphologies, and for the fabrication of particles of different sizes with narrow size distribution. The aerogel nanofiber microspheres elicit enhanced proliferation and differentiation of stem cells in comparison to solid microspheres. Further, the injectable, cell-laden nanofiber microspheres can form in situ microtissue-like structures when cultured in confined spaces within microchannels. Taken together, the injectable nanofiber microspheres are cell delivery vehicles that can aid in tissue regeneration of irregular-shaped defects.

EXAMPLE 2

The issue of bone loss in the oral cavity continues to be a perennial problem, especially in the older populations (Jeffcoat, M. K., J. Bone Miner. Res. (1993) 8:S467-S473). One of the primary causes for bone loss in the oral cavity is periodontitis. A recent survey report on the prevalence of periodontitis gave an estimate of 1 in 2 adults aged ≥30 years suffering chronically from the disease (Eke, et al., J. Periodontol. (2015) 86:611-622.). Bacterial infection and host response inflammation during periodontitis can lead to erosion of the alveolar bone that supports the teeth, periodontal ligaments, and adjacent soft tissue, thus leading the tooth to become nonfunctional (Haze, et al., J. Cell. Mol. Med. (2009) 13:1110-1124). The removal of the infected tooth can further lead to resorption of the alveolar bone (Hansson, et al., J. Dent. Biomech. (2012) 3:1758736012456543). As bone is a mechanosensitive tissue, the lack of masticatory function at the site of tooth loss can lead to bone resorption resulting from disuse atrophy (Cohn, S. A., Arch. Oral Biol. (1965) 10:909-919). Diabetes mellitus is another factor that increases the risk of alveolar bone resorption due to the activation of osteoclasts in the periodontium (Wu, et al., Int. J. Oral Sci. (2015) 7:63-72). In the light of the limited availability and donor site morbidity of autografts, as well as poor bone healing potential of allografts, it is important to develop synthetic biomaterial grafts for the regeneration of maxillary and mandible bone tissues. Further, the flat bones of the jaws and skull directly form the bone tissue by the differentiation of mesenchymal stem cells into osteoblasts, with healing rates twice as slow as the long tibial bone for identical defect sizes (Mackie, et al., J. Endocrinol. (2011) 211:109-121; Lim, et al., Tissue Eng. Regener. Med. (2013) 10:336-340). Therefore, it is imperative that synthetic bone graft materials be designed with suitable degradation rates and osteoinductive properties to accelerate the regeneration of the alveolar bone tissue.

Tissue engineering holds great promise for the healing of alveolar bone defects. The current biomaterial-based strategies for alveolar regeneration include a combination of growth factor delivery, such as enamel matrix derivative (EMD), platelet-derived growth factor (PDGF), bone morphogenetic protein-2 (BMP-2), and fibroblast growth factor-2 (FGF-2), apart from cell therapy by somatic/adult stem cells (Shimauchi, et al., Jpn. Dent. Sci. Rev. (2013) 49:118-130). On the basis of the understanding that tissue regeneration occurs in two phases—proliferation and differentiation—a dual sequential delivery of PDGF and simvastatin from core-shell microspheres was employed for the regeneration of the periodontal bone tissue in vivo (Chang, et al., Biomaterials (2013) 34:9990-9997). The anti-inflammatory drug ibuprofen encapsulated in the electrospun poly(e-caprolactone) (PCL) nanofiber membrane can applied to prevent periodontal inflammation-triggered bone resorption (Batool, et al., Materials (2018) 11:580). As noted earlier, diabetes mellitus is another health condition that generates a pro-inflammatory environment in the periodontal defect sites, thus leading to bone loss. To address such complications in diabetic patients, interleukin 4 (IL4) can be incorporated in heparin-modified gelatin nanofibrous microspheres for switching the pro-inflammatory M1 macrophage into pro-healing/anti-inflammatory M2 macrophage phenotype (Hu, et al., ACS Appl. Mater. Interfaces (2018) 10:2377-2390). Such an osteoimmunomodulatory biomaterial system reduced inflammation and enhanced dentoalveolar bone formation in diabetic rats.

With regard to bone tissue engineering of the maxilla/mandible devoid of autologous stem cells, a combination of bioresorbable polymer and bioactive calcium phosphates (CaPs) loaded with osteoinductive factors are interesting options. A biphasic gelatin-hydroxyapatite-β-tricalcium phosphate (gelatin-HA/β-TCP) porous cryogel composite infused with BMP-2 protein-loaded poly(D,L-lactide-co-glycolide) (PLGA) microspheres facilitated alveolar ridge augmentation in vivo (Chang, et al., J. Formos. Med. Assoc. (2017) 116:973-981). Biphasic scaffolds of PCL-HA 3D constructs fabricated by rapid prototyping reinforced in a chitosan-poly-glycolic acid hydrogel exhibited adequate swelling and osteogenic and antibacterial properties as necessary for alveolar regeneration (Dario, et al., Polym. Int. (2016) 65:631-640). With particular reference to electrospun nanofibers, few studies have demonstrated their use as barrier membranes for guided tissue regeneration (GTR), wherein the barrier membrane separates the epithelium of the gingiva from the connective tissue for promoting the regeneration of the periodontal tissue. Random and aligned electrospun chitosan nanofiber membranes supported matrix deposition by human embryonic stem cell-derived mesenchymal progenitor cells, thus indicating their potential application for GTR by acting as a barrier to the gingival epithelium migration into the periodontal defect site (Qasim, et al., Dent. Mater. (2017) 33:71-83). Fused deposition modeling (FDM)-derived PCL-b-TCP scaffold and PCL electrospun membrane were press-fit into composite biphasic scaffolds and cultured with osteoblasts and periodontal ligament (PDL) cell sheets. The cell-loaded scaffolds were transferred into dentin slices and further subcutaneous implantation led to the deposition of the thin cementum-like tissue on the dentin as necessary for the regeneration of the periodontal tissue (Vaquette, et al., Biomaterials (2012) 33:5560-5573). In contrast to the complex methods adopted in the aforementioned studies, the present study investigates the use of mineralized electrospun nanofiber fragments coupled with calcium-binding osteoinductive peptides for the regeneration of oral alveolus. While the inflammatory response, ectopic bone formation, and cancer risks of the whole-BMP-2 protein may pose complications in bone healing (Zara, et al., Tissue Eng. Part A (2011) 17:1389-1399), the efficacy of E7-conjugated BMP-2-mimicking peptides for alveolar bone defect repair was investigated.

Materials and Methods

Materials

PLGA with lactide-to-glycolide monomer ratio of 50:50 was procured from LACTEL (absorbable polymers, Mw 30,000-60,000); Type I collagen (calf-skin lyophilized) from Elastin Products Co., Inc, Owensville, MO; Gelatin Type A (from porcine skin powder) from Sigma-Aldrich; Hexafluoroisopropanol (HFIP) from Acros; and glutaraldehyde (GA) 25 wt % in ethanol. E7-BMP-2 Peptide (EE-EEEEKIPKASSVPTELSAISTLYL (SEQ ID NO: 2), 3022.28 g mol$^{-1}$) and E7-BMP-2-fluorescein isothiocyanate (FITC) (EEEEEEEKIPKASSVPTELSAISTLYL (SEQ ID NO: 2)-FITC, 3524.82 g mol$^{-1}$) were custom synthesized and characterized by GenScript Co., Inc.

Fabrication of Thin PLGA/Collagen/Gelatin (PCG) Electrospun Nanofiber Membranes

The fabrication of PCG electrospun nanofiber membranes is similar to that in Example 1. The electrospinning solution was prepared by mixing 0.750 g of PLGA (50:50), 0.375 g of type I collagen, and 0.375 g of gelatin Type A in 20 mL of HFIP overnight. The solution was subsequently stored at 4° C. For fabricating thin PCG nanofiber membranes, electrospinning was performed for 1 hour with typical electrospinning parameters of 15 kV applied DC voltage, flow rate of 0.4 mL/hour, and distance of 20 cm between the spinneret and the rotating mandrel. The nanofiber membrane was carefully removed from the collecting mandrel and cross-linked using GA vapors from a 25 wt % ethanolic solution for 24 hours.

Biomineralization of PCG Nanofiber Membranes in Simulated Body Fluid (SBF)

To increase the surface density of polar functional groups, the cross-linked PCG nanofiber membranes were treated with air plasma under vacuum for 1 minute each on either side. Subsequently, the nanofiber membranes were immersed in a modified 10×SBF solution (Weng, et al., J. Biomed. Mater. Res. B Appl. Biomater. (2017) 105:753-763). A supersaturated solution of the 10×SBF solution was prepared by dissolving NaCl (1000 mM), CaCl$_2$ (25 mM), and NaH$_2$PO$_4$.2H$_2$O (10 mM) in deionized water. Approximately 30 mg of the PCG nanofiber membrane was immersed in 100 mL of 10×SBF containing 42 mM of NaHCO$_3$. The mineralization of the PCG nanofiber membrane was performed at 37° C., with slow stirring of the SBF solution for ~16 hours. The mineralized membranes were rinsed thoroughly in D.I. water several times to detach any precipitates and freeze-dried before SEM characterization.

Preparation of Short Nanofiber Fragments and their Loading and Release Studies with the E7-BMP-2-FITC Peptide The mineralized PCG nanofiber membranes were frozen in water at −80° C. and cryocut at −20° C. to segments of 20 mm thickness. The cryocut mineralized PCG segments were freeze-dried to obtain the short nanofiber fragments for peptide loading and further in vivo studies. Both the E7-BMP-2 peptides (without and with FITC labeling) were reconstituted at 1.0 mg/mL in Tris-buffered saline (TBS; pH=7.4). For the quantification of peptide loading and release kinetics, predetermined weights of mineralized PCG nanofiber fragments were incubated in 100 µg/mL of the E7-BMP-2-FITC peptide (Peptide:FITC=1:1) in TBS for 24 hours at room temperature. The difference in the peptide concentration before and after incubation of the mineralized PCG fragments was determined to estimate the peptide loading. The peptide release from the mineralized nanofiber fragments was recorded by measuring the fluorescence intensities of the buffer aliquots at regular intervals using excitation and emission filters of 485 and 528 nm, respectively.

Characterization of the Mineralized PCG Nanofiber Membranes and Cryocut Fragments The surface morphology of the electrospun PCG nanofiber membrane, mineralized PCG membrane, and mineralized cryocut fragments was characterized by scanning electron microscopy (FEI Quanta 200). The samples were mounted on double-side conductive carbon tape and sputter coated with a Au—Pd target at 15 mA for 5 minutes. The SEM images were acquired at accelerating voltages of 20-25 kV. For analysis of the mineral composition on the nanofiber fragments, elemental analysis was performed using energy dispersive X-ray spectroscopy (EDAX). Additionally, the phase composition of the mineral coating on the PCG nanofiber fragments was characterized by X-ray diffraction (XRD). The mineralized PCG fragments were either crushed into fine powders without any heat treatment or calcined at 300° C./500° C. for 5 hours, at a heating rate of 2° C./minute. The fine powder samples were used for the XRD experiments, which were performed using a Rigaku Smart Lab diffractometer in Bragg-Brentano geometry, Cu Ka Xray source (1.5418 Å), with 40 KV, and 44 mA setting. The data were collected in the interval of 0.02-degree steps, in the 2 h range of 10–90° at the scan rate of 3°/minute. A D/tex Ultra 250 Silicon strip detector was used in 1D-scanning mode to collect the scattered X-ray intensity. Further, the E7-BMP-2-FITC peptide-loaded mineralized PCG nanofiber fragments were characterized by fluorescence microscopy (Zeiss).

Cytotoxicity Assessment of Cryocut Nanofiber Fragments

The potential cytotoxicity of the cryocut nanofiber fragments was assessed by the MTT assay. L929 mouse aerolar fibroblasts were procured from the American Type Culture Collection (ATCC) and revived in Eagle's minimum essential medium supplemented with 10% horse serum. The cells were expanded and maintained in the above complete media in a $CO_2$ incubator at 37° C., 95% relative humidity, and 5% $CO_2$. For the cytotoxicity assessment, the following experimental groups were evaluated: (i) PCG nanofiber fragments, (ii) E7-BMP-2 peptide (100 µg/mL)-loaded PCG nanofiber fragments, (iii) Mineralized PCG nanofiber fragments, and (iv) E7-BMP-2 peptide (100 µg/mL)-loaded mineralized PCG nanofiber fragments.

The cytotoxicity assessment was carried out in accordance with the guidelines set by ISO 10993-5: 'Tests for Cytotoxicity—In Vitro Methods' in the direct contact exposure method. For the experiments, 1, 2, and 5 mg of the nanofiber fragments from each of the 4 groups were co-cultured with L-929 mouse fibroblasts in a 0.1 wt % agar-coated 24-well plate at a seeding density of $2.5 \times 10^4$ cells/well. After 3 days of culture, complete media containing 15% (v/v) of (3-(4,5-dimethylthiazol-2-yl)-2,5-diphenyltetrazolium bromide media or MTT (5 mg/mL) was replenished and incubated for 4 hours. Subsequently, the medium was removed and the formazan crystals were solubilized in 200 µL of dimethyl sulfoxide (DMSO). The absorbance of the purple formazan was measured at 490 nm using a multimode microplate reader (BioTek Synergy H1 Hybrid).

Alveolar Bone Defect Study

In the present study, the efficacy of calcium-binding BMP-2 peptide-loaded mineralized PCG nanofiber fragments were tested for alveolar bone regeneration in vivo.

Figure 11E:
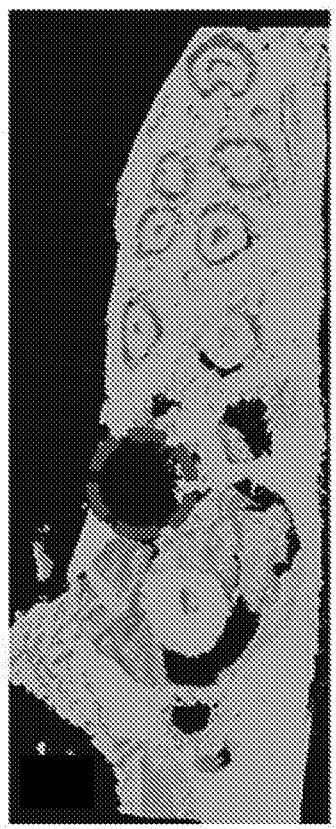
FIGS. 11D-11G provide representative 3D reconstructions of coronal (XZ) view micro-CT images of the defect immediately after tooth extraction and defect creation (FIG. 11D), unfilled defect/control after 4 weeks (FIG. 11E), defect filled with mineralized PCG nanofiber fragments (FIG. 11F), and defects filled with E7-BMP-2 peptide-loaded mineralized PCG nanofiber fragments (FIG. 11G). The dashed circles indicate the region of the defect.
Figure 11G:
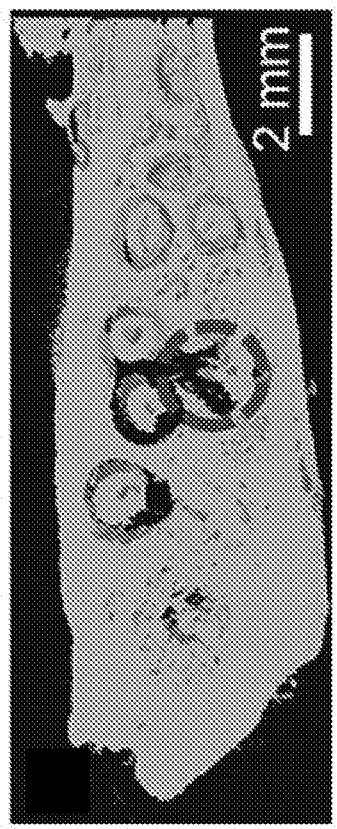
Figure 11D:
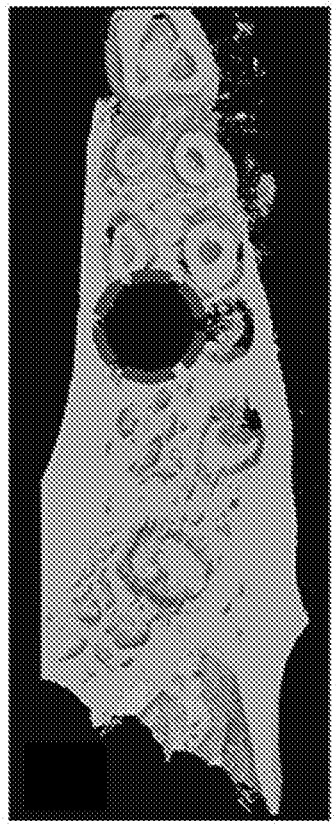
Figure 11F:
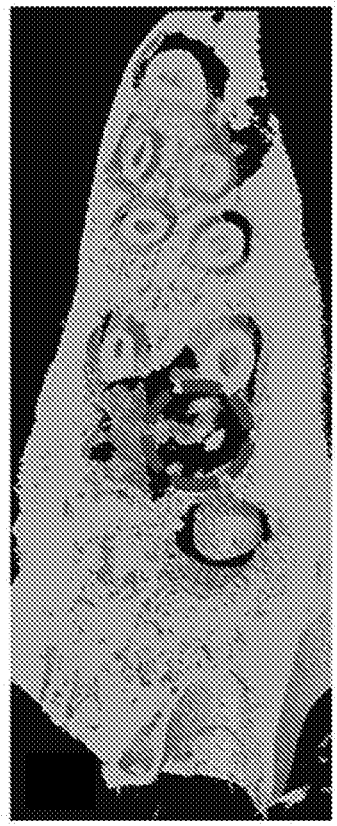

All the animal experiments performed in this study followed the animal experimentation protocols approved by the Institute Animal Care and Use Committee (IACUC) of the University of Nebraska Medical Center. A standardized tooth extraction rodent model was used, and postextraction graft procedures (Willett, et al., J. Periodontol. (2017) 88:799-807). Ten- to twelve-month-old female retired-breeder female Sprague Dawley rats were used as the animal model for the periodontal defect study. Before the surgery, the rats were acclimatized to the animal housing facility cages and fed on standard laboratory diet at ambient humidity and temperature. The surgery was performed in rats under general anesthesia using the nose cone method to deliver ~2% isofluorane/100% $O_2$. Before the extraction of the first molar tooth (M1) from the rat maxillae, local anesthesia of 0.1 mL of 3% carbocaine in 1:20,000 neocobefrin was injected into the maxillary vestibule adjacent to the M1. Following the removal of the M1 tooth on both sides, the socket was enlarged to a critical-sized defect of 2 mm diameter×2 mm depth in the maxillary bone with the help of a dental bur of 2 mm diameter under saline irrigation. The defects were either filled with graft materials for the experimental groups or left unfilled for the control group. The defects were subsequently closed by carefully suturing the adjacent soft tissue using a #6/0 line, followed by the application of a cyanoacrylate bioadhesive/bioglue (PeriAcryl 90, GluStitch, Delta, BC) to hold the graft in place. Post-surgery, 0.01 mg/kg dose of buprenorphine opioid was administered subcutaneously. FIGS. 11A-11C show intraoperative images of the periodontal defect creation in the rat maxillae (upper jawbone), filling of the defect with mineralized nanofiber graft, and surgical suturing of the tissue adjacent to the defect to hold the graft in place. A total of 9 rats divided into 3 groups with two defects per rat were used for the animal experiments. The three experimental groups are as follows: (i) unfilled defect/control, (ii) 2 mg of mineralized PCG nanofiber fragments, and (iii) 2 mg of E7-BMP-2 peptide-loaded mineralized PCG nanofiber fragments. For a critical-sized defect of 2 mm×2 mm (diameter× depth), it was possible to fill only up to 2 mg of mineralized PCG nanofiber fragments as determined in the pilot study. Therefore, 2 mg of the fiber fragments was used for the subsequent in vivo experiments. Postsurgery, after allowing 4 weeks for defect healing, the rats were euthanized by $CO_2$ asphyxiation and the rat maxillae were retrieved and fixed in 10% formalin for 3 days. The tissues were then transferred to 70% ethanol for radiographic and histological examination.

The formalin-fixed maxillae were scanned with a high-resolution X-ray micro-CT scanner (SkyScan 1172, Kontich, Belgium) using a tube voltage of 70 kV, current of 141 mA, and a slice thickness/slice increment of 8.71 µm. The analysis of the micro-CT data was performed using CT analyzer software (Brucker microCT). From the multiple scan slices, a 3D reconstruction was performed for each of the two sides of the rat maxillae. For evaluating new bone formation in the maxilla, the coronal image slices were 3D reconstructed. The region of interest (ROI: 2 mm diameter×2 mm depth) was selected in the area anterior to the roots of the second molar tooth (M2), where the critical-sized 2 mm defect was made for the surgery. The coronal view micro-CT image of the maxilla immediately after defect creation also aided in locating the defect site. In the ROI delineated by dashed circles, 3D reconstruction of the coronal images was performed using CT SkyScan software. For the 3D reconstruction, ~200 coronal (XZ) slices from the cementum-enamel junction (CEJ) below into the alveolar bone were used. From the circular defect regions, the new bone volume percentage, bone mineral density, and trabecular bone parameters (trabecular thickness, number, and separation) were determined.

Subsequent to acquiring the data for radiographic analysis, the rat maxillae were immersed in decalcification buffer, i.e., Rapid Cal Immuno (BBC Biochemical, Mount Vernon, Wash.) for 2 weeks. The decalcification buffer was aspirated and replenished every 2 days for the 2-week period. Following decalcification, the maxilla was bisected as two halves, dehydrated with an increasing gradient of ethanol series (70-100%), and embedded in separate paraffin wax blocks. From the embedded tissue blocks, tissue sections of 4 µm thickness were prepared using a microtome. Several sections were prepared for each sample and stained with hematoxylin and eosin (H&E) or Masson's trichrome, following the instructions provided by the manufacturer. The stained sections were examined using a Ventana's Coreo Au slide scanner 3.1.3. Using Ventana image viewer v. 3.1.3, representative snapshots were taken at 2× and 10× magnification.

Statistical Analysis

IBM SPSS Statistics software 20 was employed for statistical analysis of data presented in the current study. All data are presented as mean±standard deviation of n=6 replicates per group. One-way analysis of variance (ANOVA) with the Tukey test was performed to assess statistical significance at p<0.05, where p denotes the probability that there is no significant difference between the mean values of the compared groups.

Results

Morphology of Mineralized PCG Membrane and Cryocut Nanofiber Fragments

Figure 8:
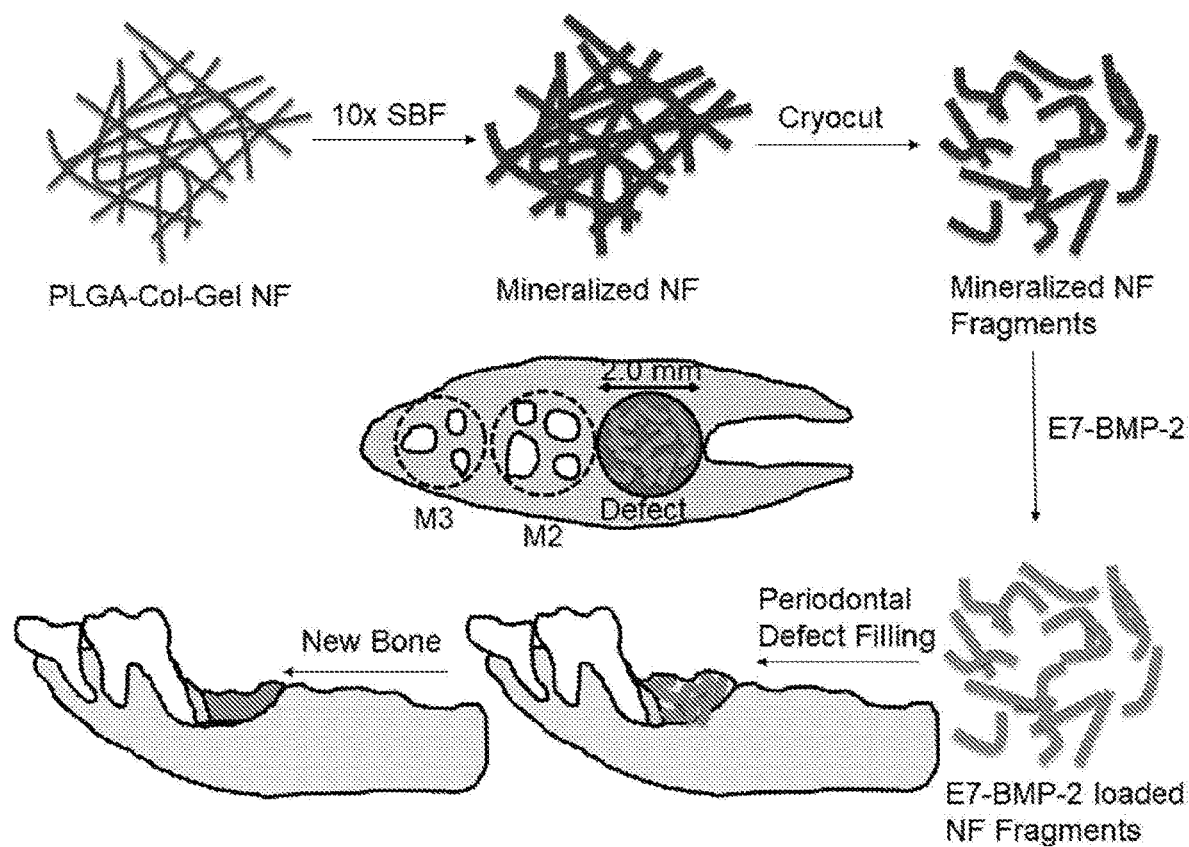
FIG. 8 provides a schematic illustration of the application of mineralized nanofiber segments immobilized with calcium coupling of the E7-BMP-2 peptide for periodontal bone regeneration in maxillary defects (2 mm diameter×2 mm depth) created following the extraction of the first molar tooth (M1).

As mentioned in the introduction, growth factor and anti-inflammatory cytokine-loaded microspheres have been studied for the regeneration of the periodontal/alveolar bone tissue. On similar lines, the current study is the first report on the application of mineralized short nanofiber fragments coupled with osteoinductive peptides for periodontal bone tissue engineering. FIG. 8 is a schematic illustration showing the application of mineralized nanofiber segments loaded with the E7-BMP-2 peptide for the healing of critical-sized (2 mm diameter×2 mm depth) defects in rat maxillae. The morphology of the electrospun PCG nanofiber membrane before and after mineralization in modified 10×SBF was studied by SEM. Using Image J, the diameters of the GA cross-linked electrospun PCG nanofibers were in the range of 249±112 nm (FIG. 9A). Further, it is well known that as the thickness of the nanofiber membrane increases with the duration of electrospinning, the porosity of the membrane is drastically reduced. It was shown that the pore size reduced significantly from ~35 μm to 0.9 μm in PCL-collagen nanofiber membrane for electrospinning duration from 10 to 40 seconds under typical operating parameters of 10-15 kV DC voltage, flow rate of 0.6 mL/hour, and spinneret-to-collector distance of 10 cm (Babak, et al., J. Biomed. Mater. Res. A (2016) 104:1479-1488). Such a decrease in porosity was shown to hinder cellular infiltration into the membrane. Here, the biomineralization of electrospun nanofibers was observed predominantly on the surface of thick nanofiber membranes due to the low membrane porosity. Therefore, thin nanofiber membranes were electrospun for 1 hour to ensure maximal coverage of the membrane with CaP minerals. The diameters of the PCG nanofibers increased from 249±112 nm to 1758±346 nm upon mineralization overnight in 10×SBF for 16 hour. A flaky apatite-like mineral coating morphology was seen on the mineralized fiber membrane (FIG. 9B), which was retained after cryocutting to 20 μm thick fragments (FIGS. 9C and 9D). Because of the large amount of mineral deposition on the membrane, the fiber fragments are aggregates of nanofibers within the 20 μm segments and not dispersed as individual mineralized fibers.

Elemental and Phase Composition of the Mineral Coating on PCG Nanofiber Fragments The composition of the mineral coating on the PCG nanofiber fragments was characterized by EDAX. As expected, X-ray signals were detected for calcium (Ca), phosphorus (P), and oxygen (O) from the flaky mineral coating. A semi-quantitatively analysis shows that the order of elemental abundance (wt %) in the mineral coating was Ca>P>O. A quantitative assessment of the mineral coating was obtained by point scan at different locations on the mineral coating. FIG. 9E shows the point probe (shown in the inset) EDAX spectrum of the mineralized nanofiber fragments. The EDAX spectrum shows all the signals identified in the elemental mapping and line scan along with additional signal from the Al foil on which the sample was mounted. From the peak areas in the EDAX spectra, the molar ratio of Ca/P was ascertained to be 1.65±0.06, which is close to a Ca/P ratio of 1.67 in hydroxyapatite (HA). Further, the XRD data of the mineralized PCG nanofiber fragments without and with heat treatment discerned characteristic peaks for hydroxyapatite. The mineralized fiber fragments without heat treatment exhibited a broad amorphous hump at lower angles ($2\theta=10$-$25°$) because of the polymer backbone. At 300° C. and 500° C., calcination removed the amorphous polymer content leading to more intense crystalline peaks of hydroxyapatite. Further, no phase transformation of the hydroxyapatite mineral coating was detected due to the low calcination temperatures (Boda, et al., J. Phys. Chem. C (2015) 119:6539-6555). Thus, the mineral coating on the PCG nanofiber fragments was ascertained to be flaky HA.

Figure 10A:
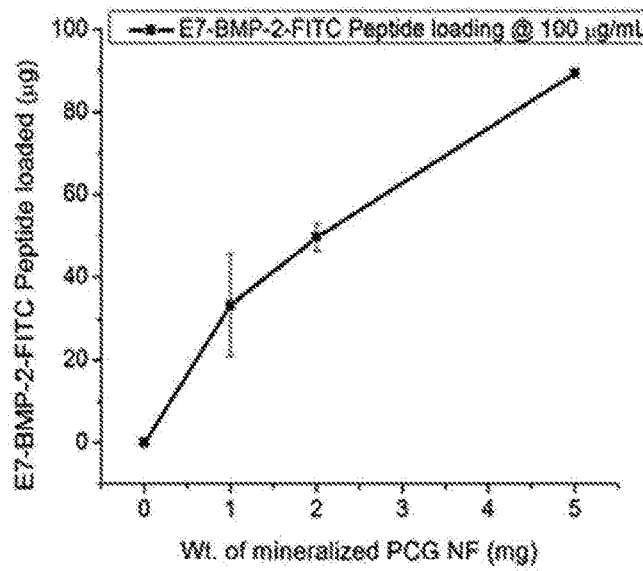
FIG. 10A provides a graph of the loading of the E7-BMP-2-FITC peptide on mineralized PCG NF fragments by immersing in 100 μg/mL of the peptide solution in TBS for 24 hours at room temperature.
Figure 10B:
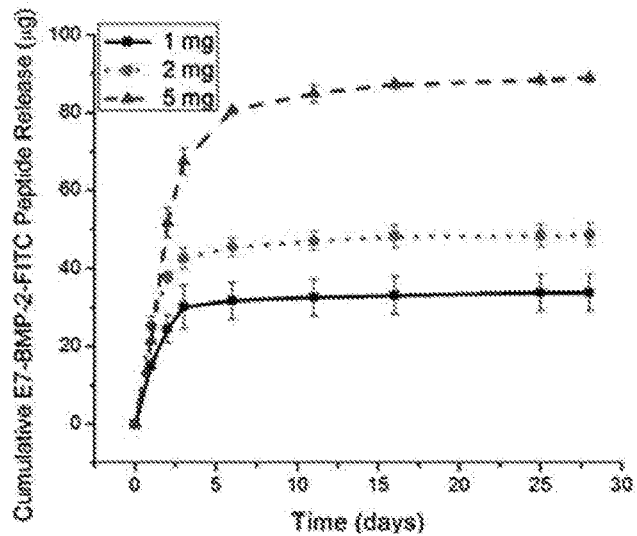
FIG. 10B shows the cumulative release profiles over 4 weeks for the indicated three peptides loadings.
Figure 10C:
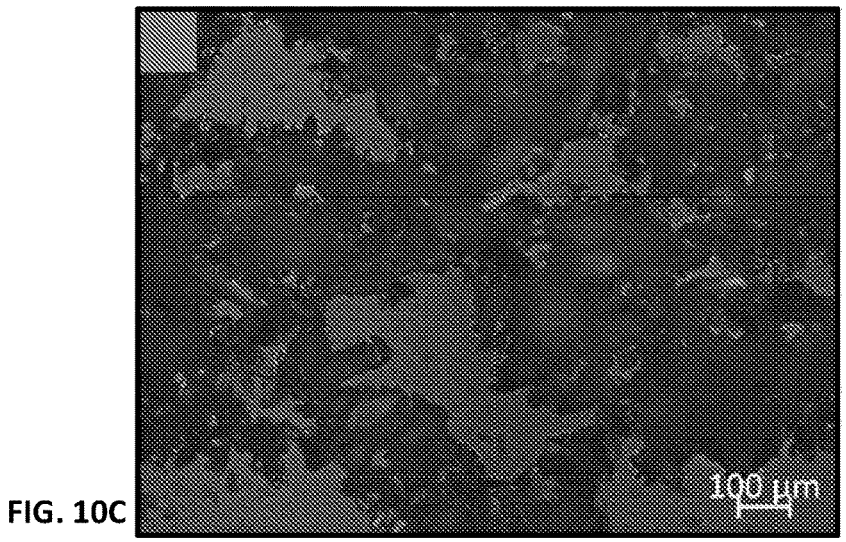
Figure 10D:
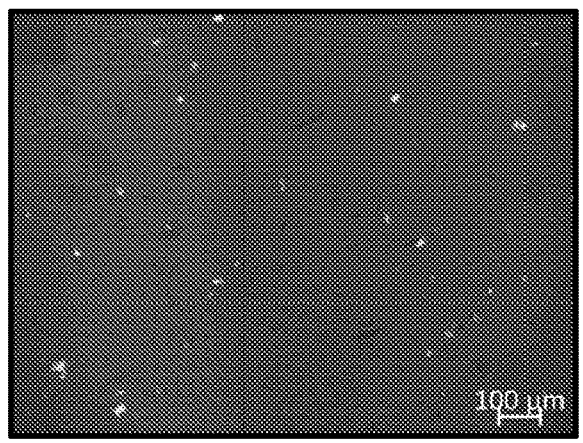
Figure 10E:
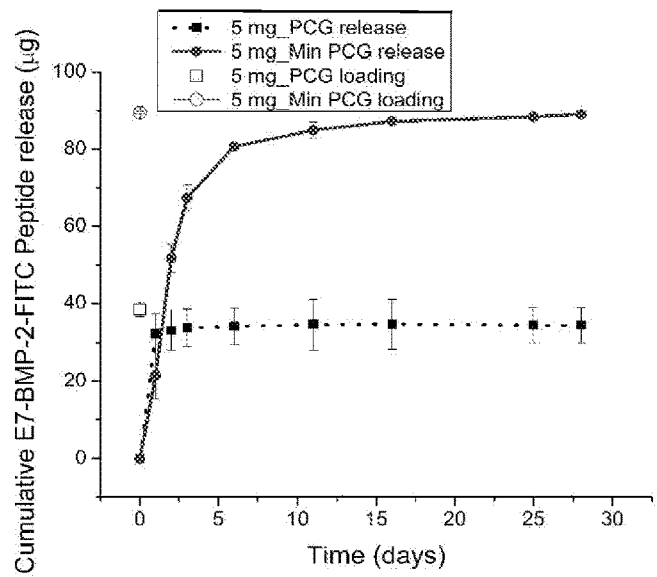
FIG. 10E provides a comparative loading and release profiles of E-BMP-2-FITC peptide for 5 mg each of PCG and mineralized nanofiber fragments.

Loading and Release of the E7-BMP-2-FITC Peptide from Mineralized PCG Nanofiber Fragments The loading and release of the E7-BMP-2 peptide from the mineralized nanofiber fragments was quantified by measuring the fluorescence intensity of the FITC peptide analog in Tris-buffer saline. At a peptide concentration of 100 μg/mL, the loading of the mineralized nanofiber fragments increased proportionately to the weight of the mineralized PCG fragments. For 1, 2, and 5 mg of mineralized PCG nanofiber fragments, ~33, ~50, and ~90 mg of the peptide loading was recorded, respectively (FIG. 10A). Sustained release profiles of the peptide were recorded for all the three peptide loadings (FIG. 10B), with >95% of the peptide released within 4 weeks. FIGS. 10C and 10D are representative fluorescence micrographs of the E7-BMP-2-FITC peptide-loaded nanofiber fragments, immediately after loading and after 4 weeks of release, respectively. The slow dissolution of CaP minerals from the mineralized nanofiber fragments in the Tris-buffer supposedly facilitates the sustained release of the peptide. Additionally, the loading and release profiles of the E7-BMP-2 peptide for 5 mg of each of the mineralized and nonmineralized PCG nanofiber fragments were compared. A much higher amount of the E7-BMP-2 peptide (~3 times) can be loaded onto the mineralized PCG fragments than onto the PCG fragments (FIG. 10E). Additionally, the peptide release for the PCG fragments exhibited a burst release profile, with >95% of the peptide released within 24 hours, whereas a similar percentage was released within 1 week in case of the mineralized PCG fragments. Thus, a controlled release of the E7-BMP-2 peptide from the mineralized PCG nanofiber fragments can be ascertained.

Cytocompatibility of Cryocut Nanofiber Fragments In Vitro

Figure 10F:
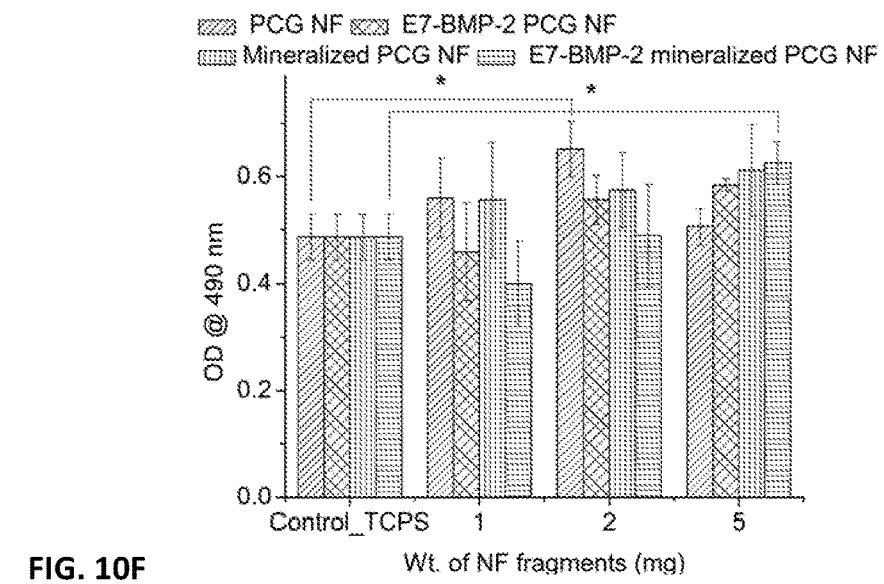
FIG. 10F provides a dose dependent cytotoxicity evaluation of cryocut nanofiber fragments after 3 days of co-culture with L929 mouse fibroblasts in vitro. All data shown are mean±sd of n=3 replicates per experimental group. * indicates statistically significant difference of the corresponding experimental group with respect to the control tissue culture polystyrene (TCPS) at $p<0.05$ where p denotes the probability that there is no significant difference between the compared groups.

A dose-dependent cytotoxicity evaluation of the cryocut nanofiber fragments with L929 mouse fibroblasts revealed favorable cytocompatibility of all the 4 experimental groups with regard to the control tissue culture polystyrene (TCPS) after 3 days of culture. A close observation of the results in FIG. 10F indicates a composition and dose-dependent variation in cell viability. Except for the PCG nanofiber fragments, all the other experimental groups elicited a dose-dependent variation in cell viability (although not statistically significant between the doses). Particularly, at a low dosage (1 mg), the E7-BMP-2-loaded mineralized PCG nanofiber fragments elicited lower cellular activity (although not statistically significant with regard to TCPS control), which was revived at 2 mg and significantly higher than that of control at 5 mg. In fact, the viability and proliferation of the fibroblasts co-cultured with the PCG nanofiber fragments and the E7-BMP-2 peptide-loaded mineralized nanofiber fragments were significantly higher than the TCPS control. As the doubling time of L929 fibroblasts was 21-24 hours and the MTT assessment was performed after 3 days of co-culture, the results also reflected on the proliferation effects of the PCG nanofiber fragments. Further, enhanced cell proliferation on nanofiber matrices over conventional 2D flat substrates/films using the MTT assay has been observed (Wu, et al., J. Bioact. Compat. Pol. (2011) 26:565-577). In FIG. 10F, the cellular activity seems to increase with an increase in the dosage of the nanofiber fragments. This indicates a mitogenic effect of the cryocut nanofiber fragments on the aerolar mouse fibroblasts. Such a cell proliferative effect can aid in wound healing and defect closure in vivo. In contrast to cellulose nanofibrils that induced apoptosis and activated cellular stress genes in bovine fibroblasts at doses>0.2 mg/mL (Pereira, et al., Nanotechnology (2013) 24:075103), the cryocut short nanofiber segments in the present study are cytocompatible even at exposure doses of 2 and 5 mg/mL.

Alveolar Bone Regeneration In Vivo

A PCG nanofiber composition was chosen for apatite mineralization, and the mineralized nanofiber fragments were coupled with the calcium-binding E7-BMP-2 peptide for the alveolar bone regeneration in 2 mm critical-sized defects. Following tooth extraction, drilling of critical-sized defects, surgical placement of the mineralized graft, and defect closure by suturing, a small dip in the body weight of the rats was recorded for the first week post-surgery. This can be ascertained by the inability of the rats to consume even softened "ad libitum" due to the initial inflammation that incurred during the surgery. The initial inflammatory response arose because of the tooth extraction followed by further drilling of the maxillary bone underneath to create critical-sized defects. This initial inflammation lasted for 2-3 days post-surgery and therefore did not correspond to the side effects generated by BMP-2-mimicking peptides. Nevertheless, the rat body weights resumed to a normal increase from the second week up to 4 weeks.

Micro-CT Analysis

Figure 11I:
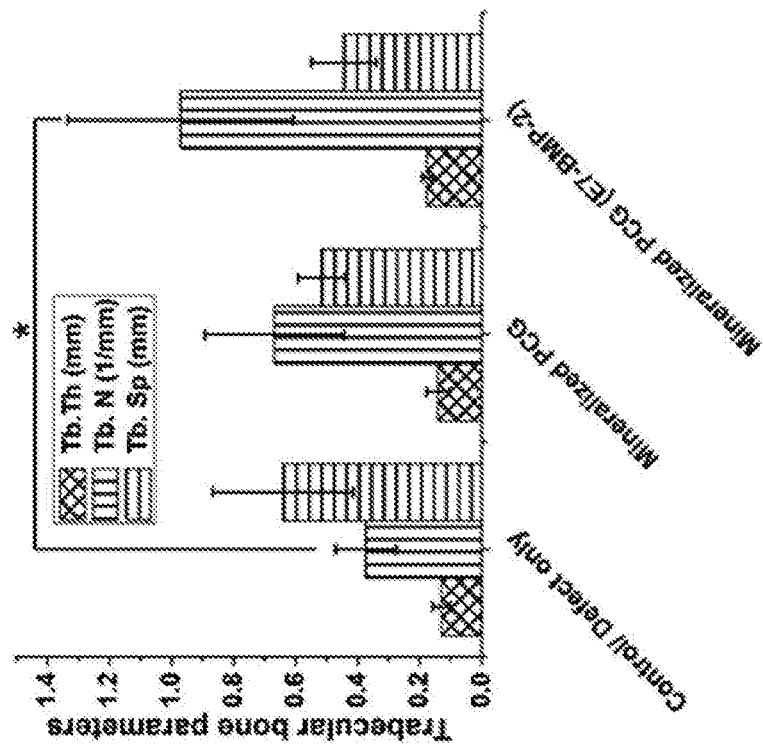
FIG. 11I shows trabecular bone parameters (thickness, number, and separation) measured in the different experimental groups after 4 weeks of suturing the periodontal defects. Data shown are mean±SD of n=6 for each group. *p<0.05.
Figure 11H:
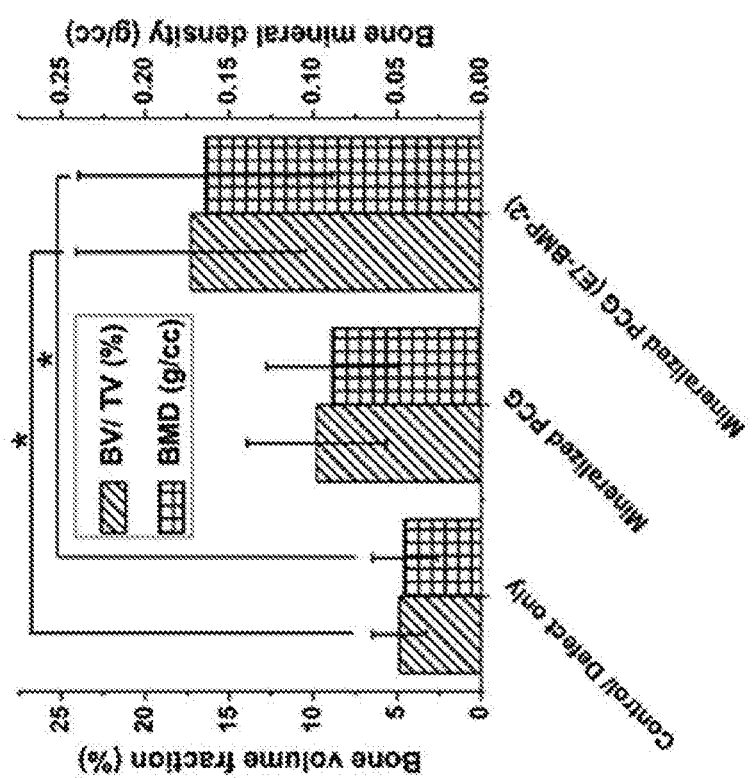
FIG. 11H shows new bone volume fraction (%) and bone mineral density (g/cc).
Figure 11J:
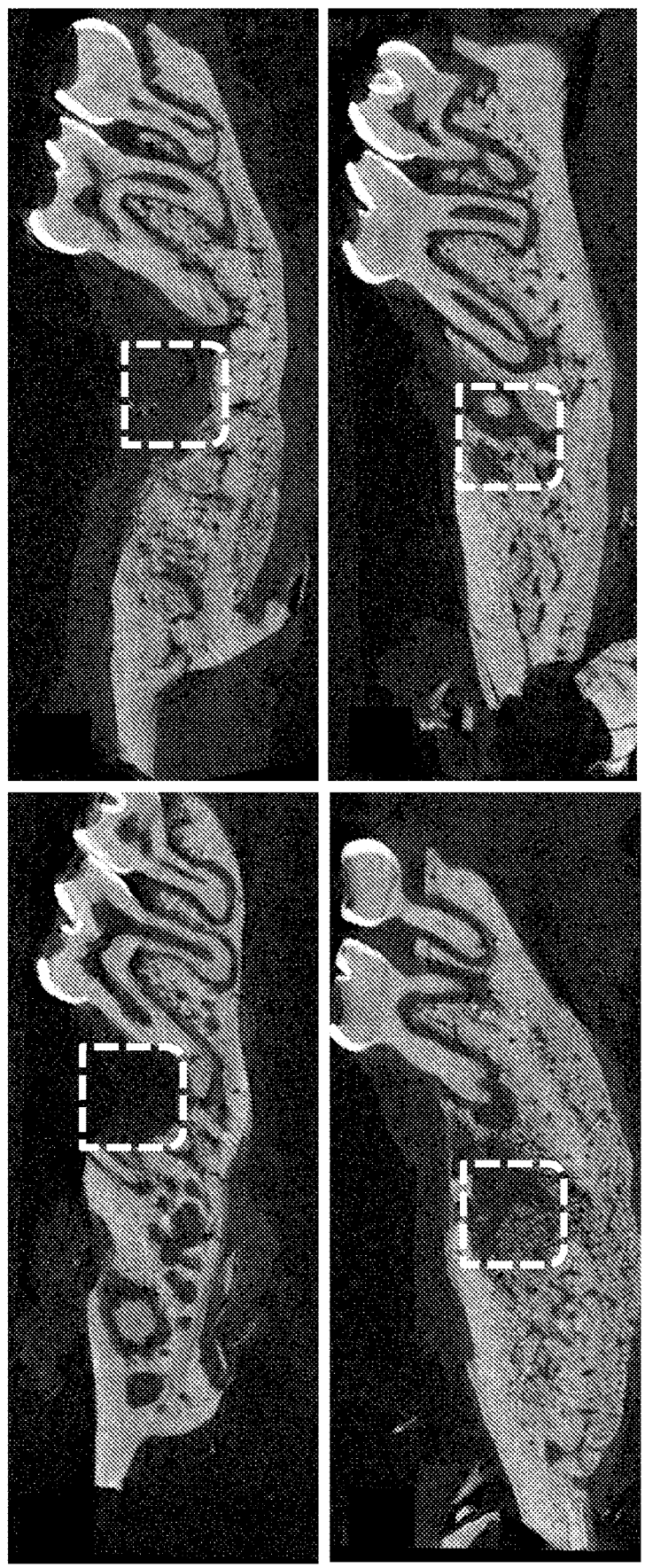
FIG. 11J provides representative sagittal (YZ) view micro-CT images of the defect immediately after tooth extraction and defect creation (top left), unfilled defect/control after 4 weeks (top right), defect filled with mineralized PCG nanofiber fragments (bottom left), and defects filled with E7-BMP-2 peptide loaded mineralized PCG nanofiber fragments (bottom right). The dashed boxes indicate the region of the defect.

Micro-CT was employed to quantify the extent of bone regeneration after 4 weeks of mineralized PCG graft implantation in rat maxillae, following extraction of the first molar tooth (M1). Representative 3D reconstructions of the coronal (XZ)-view micro-CT images for the different implant groups are shown in FIG. 11D-11G, with the regions of interest being demarcated in dashed circles. It may be noted that FIGS. 11D and E correspond to micro-CT images of the control unfilled defect group, immediately after defect creation and 4 weeks after surgery, respectively. FIG. 11H is a statistical analysis of the new bone volume percentage (BV/TV in %) and bone mineral density (BMD in g/cc) measured in the different experimental groups. The E7-BMP-2 peptide-loaded mineralized nanofiber graft alone exhibited significantly greater X-ray radiopacity within the ROI than the unfilled defect. This indicates larger new bone volume fraction (%) and bone mineral density (g/cc) of the E7-BMP-2 peptide-coupled mineralized PCG nanofiber fragments. Further, the trabecular parameters of the spongy alveolar bone tissue formed in the maxillary circular defects were determined (FIG. 11I). While the trabecular thickness (Tb.Th in mm) and the trabecular separation (Tb.Sp in mm) were similar between the experimental groups, the trabecular number (Tb.N in 1/mm) for the E7-BMP-2 peptide-loaded mineralized PCG group was significantly larger than that of the control/unfilled defect group. Although the mineralized PCG grafts without the BMP-2 peptide seemed to elicit better new bone formation than the control, no statistical significant difference was noted at $p<0.05$. Overall, the osteoinductive efficacy of the mineralized short nanofiber grafts coupled with calcium binding BMP-2-mimicking peptides for alveolar bone healing can be ascertained. It is also possible that the nonresorbed mineral coating on the nanofiber fragments can contribute to the contrast in the X-ray micro-CT. To ascertain this, histological analysis of the tissue sections from the three experimental groups was undertaken. To facilitate easy comparison with the sagittal plane histological sections, representative sagittal (YZ) view micro-CT images are shown in FIG. 11J.

Histopathological Analysis

Figure 12:
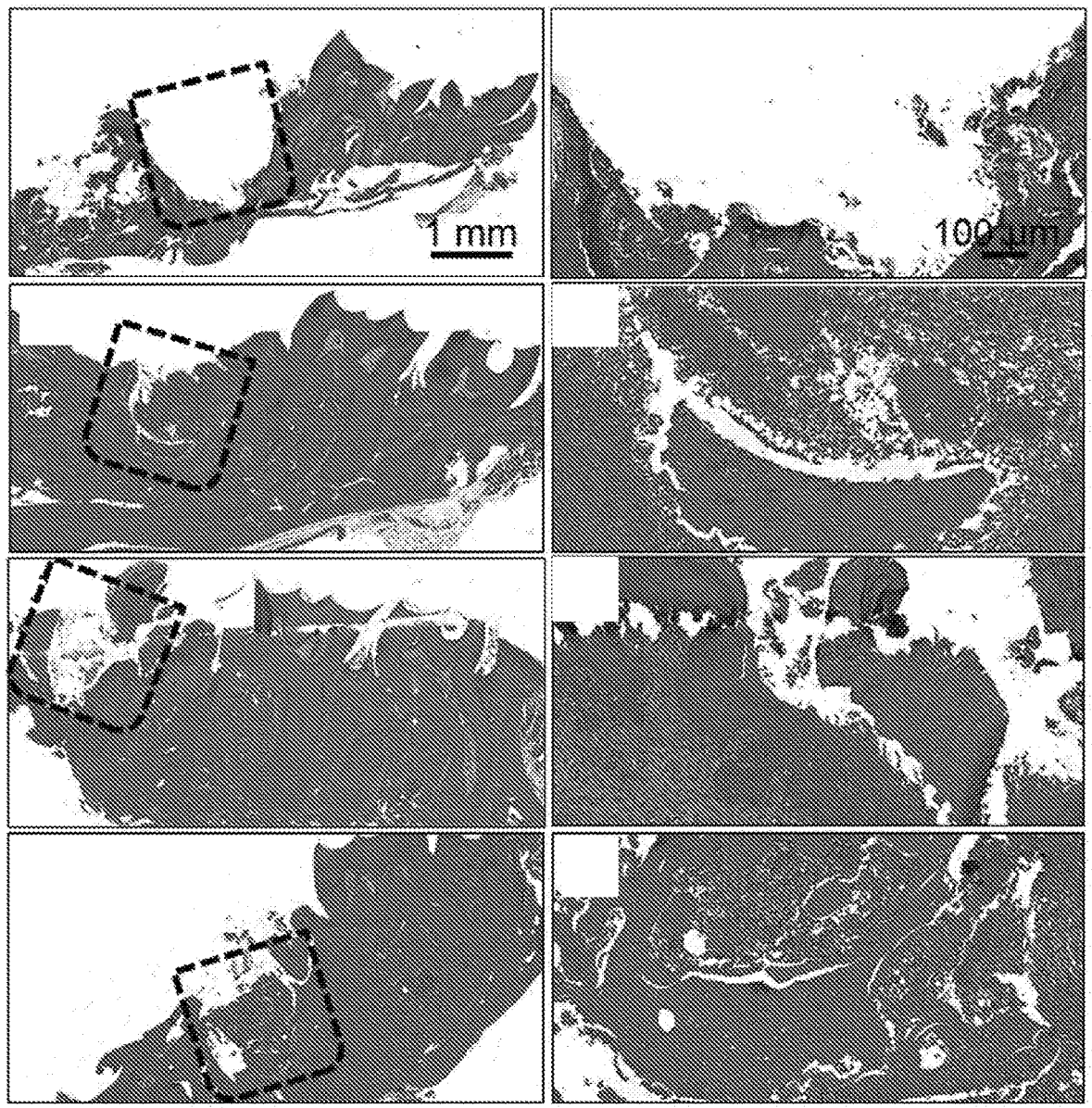
FIG. 12 provides hematoxylin and eosin-stained images of different experimental groups studied for periodontal bone healing. Row 1 (A1/A2): immediately after tooth extraction and defect creation, Row 2 (B1/B2): unfilled defect/control after 4 weeks of surgery, Row 3 (C1/C2): mineralized PCG nanofiber fragments after 4 weeks of graft implantation, and Row 4 (D1/D2): E7-BMP-2-loaded mineralized PCG nanofiber fragments after 4 weeks of graft implantation. The dashed boxes indicate the defect region.
Figure 13:
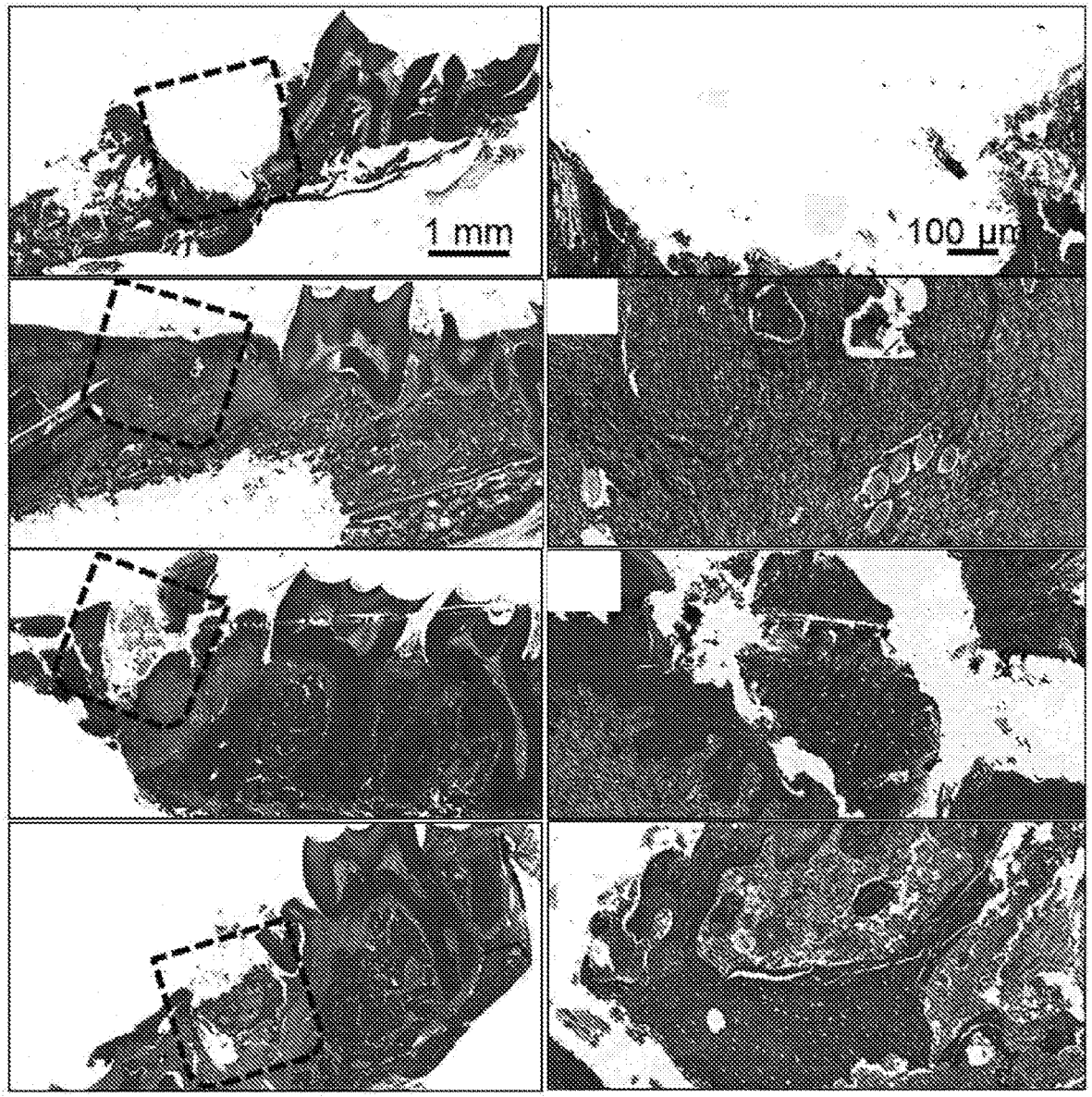
FIG. 13 provides Masson's trichrome-stained images of different experimental groups studied for periodontal bone healing. Row 1 (A1/A2): immediately after tooth extraction and defect creation, Row 2 (B1/B2): unfilled defect/control after 4 weeks of surgery, Row 3 (C1/C2): mineralized PCG nanofiber fragments after 4 weeks of graft implantation, and Row 4 (D1/D2): E7-BMP-2-loaded mineralized PCG nanofiber fragments after 4 weeks of graft implantation. The dashed boxes indicate the defect region.

Postdecalcification of the retrieved rat maxillae, tissue sections of the different experimental groups were analyzed by H&E and Masson's trichrome staining. FIG. 12 and FIG. 13 are representative H&E and Masson's trichrome-stained images for the various experimental groups, respectively. FIG. 12 A1/A2 and FIG. 13 A1/A2 correspond to the tissue section immediately after first molar extraction (M1) and defect creation in the maxillary bone. These images have been shown to demarcate the defect location adjacent to the second molar tooth (M2). The initial inflammation of the oral cavity observed after surgery completely subsided after 4 weeks of graft implantation. Importantly, no apparent inflammatory or foreign body reaction was observed in any of the experimental groups at 4 weeks. Both H&E and trichrome staining indicated retarded new bone formation and greater fibrous connective tissue in the unfilled defect/ control group (FIG. 12 B1/B2 and FIG. 13 B1/B2). On the other hand, the mineralized fragmented nanofiber graft group revealed sparsely formed new bone. The new bone formation was localized to the periphery of the defect region in case of the mineralized nanofiber fragments devoid of the E7-BMP-2 peptide (FIG. 12 C1/C2 and FIG. 13 C1/C2). In the peptide-loaded mineralized fragmented nanofiber group, greater new bone tissue was observed in the center of the defect (FIG. 12 D1/D2 and FIG. 13 D1/D2). However, the maxillary bone defects filled with the mineralized grafts did not elicit significant soft/fibrous connective tissue infiltration unlike the control unfilled defect. The nanofiber fragments may have inhibited soft fibrous and/or epithelial tissue invasion into the defect region while enhancing the osteoblastic cell migration into the defect region. This is consistent with enhanced migration and clustering of osteoblast-like cells on inorganic bone mineral (ABM) particles coated with a P-15 collagen-mimicking peptide suspended within hyaluronic acid hydrogels (Nguyen, et al., Biochem. Biophys. Res. Commun. (2003) 311:179-186). Therefore, the biomimetic mineralized nanofiber fragments create an osseous tissue-like microenvironment for greater infiltration of bone-forming cells into the defect location. Overall, the histology and micro-CT analysis together indicate the maximum osteoinductive potency of the E7-BMP-2 peptide-loaded mineralized nanofiber fragments for alveolar bone regeneration.

There is tremendous potential for tissue engineering applications of short electrospun nanofiber fragments. The injectability of the short nanofiber fragments present several advantages compared to their precursor 2D electrospun nanofiber membranes/mats. Nanofiber fragments can be fabricated by electric spark generation during electrospinning, cryogenic cutting, and probe ultrasonication (Chen et al., Adv. Drug Deliv. Rev. (2018) 132:188-213). Depending on the brittleness/ductility of the polymer, one of the aforementioned methods may be employed for the generation of short electrospun nanofiber fragments. Short nanofiber fragments of poly (glycerol sebacate) (PGS) can be fabricated from coaxial electrospun fibers of PGS core and poly-L-lactic acid (PLLA) shell by dissolving the latter in a DCM: hexane (2:1) solvent system (Ravichandran, et al., Nanotechnology (2012) 23:385102). The PGS short fibers can support the maturation of cardiomyocytes by enhancing the expression of cardiac markers—actinin, troponin, myosin heavy chain, and connexin 43, and therefore present their potential as injectable biomaterials for treating myocardial infarction. Short fibers of poly (styrene-co-maleic acid) can be cryocut into fragments, which can regulate spheroidal culture and function of primary hepatocytes, as evidenced by the responsiveness of the spheroids for the clearance of model drugs (Wei, et al., J. Mater. Chem. B (2016) 4:7155-7167). By injecting cryocut short nanofiber fragments loaded with astragalocide IV, therapeutic angiogenesis was realized by microvessel formation in the hindlimb ischemic nude mice model (Li, et al., Nanoscale (2015) 7:13075-13087).

Herein, the present study demonstrates the application of mineralized nanofiber fragments coupled with calcium-binding BMP-2-mimicking peptides for alveolar bone regeneration. With particular reference to alveolar bone tissue engineering, peptide-, protein-, and/or growth factor-loaded microparticles can being used to fill maxillary bone defects (Chang, et al., Biomaterials (2013) 34:9990-9997; Hu, et al., ACS Appl. Mater. Interfaces (2018) 10:2377-2390). However, in the current study, mineralized short nanofiber fragments are being utilized for oral bone tissue regeneration. Apart from the biomaterial and drug/growth factor delivery characteristics, the extent of periodontal bone regeneration is also dependent on clinical factors such as the alveolar defect location, the surgical procedure, and the animal model used. Sequentially delivery of PDGF and simvastatin can be used to increase new bone volume and bone mineral density (Chang, et al., Biomaterials (2013) 34:9990-9997). Further, periodontal bone healing can be induced by IL-4 delivery (Hu, et al., ACS Appl. Mater. Interfaces (2018) 10:2377-2390).

The use of nanofibers instead of nanoparticles can yield a slower sustained release of therapeutic agent (Shan, et al., Des. Monomers Polym. (2015) 18:678-689). Notably, the drug release and degradation profiles of electrospun poly(D, L-lactide) nanofibers can be modulated by varying the fiber diameter (Cui, et al., Biomacromolecules (2006) 7:1623-1629). Additionally, the extracellular matrix (ECM)-mimicking topography presented by electrospun nanofibers helps elicit a more favorable tissue regeneration response. Thus, the biomimetic mineralized nanofiber fragments are more potent for healing alveolar defects than similar micro/nanoparticles.

In the current work, the BMP-2-mimicking peptide is chemically modified by attaching a calcium-binding heptaglutamate moiety to form the E7-BMP-2 peptide. Notably, the vascular endothelial growth factor (VEGF)-mimicking peptide (QK), which may be acetylated as AcQK, can also be used to elicit angiogenesis by enhancing microvascularization of endothelial cells (Prakash Parthiban, et al., Acta Biomater. (2017) 51:330-340). The modified E7-BMP-2 and E7-QK can be tethered to mineralized nanofiber fragments/scaffolds by calcium coupling for better regeneration of vascularized bone. In addition to the heptaglutamate E7 domain, octaglutamate E8, octaaspartate D8, and bisphosphonate chemical moieties conjugated to the BMP-2-mimicking peptide may be utilized. All the aforementioned peptide modifications have been reported to enhance calcium binding as testified by >90% of the conjugated peptides bound to hydroxyapatite compared to <5% for the unmodified peptides (Murphy, et al., Biomacromolecules (2007) 8:2237-2243). Furthermore, octaaspartate D8-conjugated osteotropic peptide binds to bone resorption sites in ovariectomized rats (Wang, et al., Bioconjuguate Chem. (2007) 18:1375-1378).

Apart from therapeutic peptides, short nanofiber fragments can also be immobilized with chemotactic growth factors for bone tissue engineering applications. For example, a protease-resistant stromal cell-derived factor-1 (SDF-1) can be used for the recruitment of stem cells, thereby improving heart function following myocardial infarction (Segers, et al., Circulation (2007) 116:1683-1692). Platelet-derived growth factor (PDGF) can also be used to elicit the proliferation of vascular smooth muscle cells in vitro (Li, et al., J. Biomater. Sci. Polym. Ed. (2010) 21:803-819), while a combination of VEGF and PDGF can be used to promote skin wound healing in vivo (Xie, et al., Acta Biomater. (2013) 9:9351-9359). In a similar manner, an optimal combination of growth factors released from the nanofiber fragments can accelerate the recruitment and proliferation of stem/progenitor cells at the defect site followed by stem cell differentiation to osteoblasts.

Finally, the short nanofiber fragments can be consolidated into 3D nanofiber aerogel scaffolds for filling large-sized bone defects. As shown herein, injectable nanofiber microspheres fabricated from short nanofiber fragments can be loaded with cells, such as stem cells, for tissue regeneration. Alternatively, magnetic short fibers can be oriented in a hydrogel using an external magnetic field and such anisogel-induced unidirectional growth of functional nerve cells (Omidinia-Anarkoli, et al., Small (2017) 13:1702207), as necessary for neural tissue engineering. Alternately, strontium and copper co-doped bioactive glass nanofiber fragments can be used, which were demonstrated to enhance osteogenesis and angiogenesis, and inhibit osteoclastogenesis in vitro (Weng, et al., ACS Appl. Mater. Interfaces (2017) 9:24484-24496).

In a parallel to growth factor-loaded microspheres, the filling of alveolar bone defects with nanofiber fragments as an alternative for bone tissue regeneration has been demonstrated in the present study. Further, the coupling of calcium-binding osteoinductive peptides to the mineralized nanofiber fragments enabled sustained peptide release for 4 weeks. The E7-domain-conjugated BMP-2 peptide implicated in the faster healing of critical-sized maxillary defects of 2 mm diameter×2 mm depth in rats, which can be further tailored to E8, D8, D7, and bisphosphonate modifications for optimal calcium binding and new bone formation. The mineralized nanofiber fragments with the incorporation of peptides can be used to regenerate craniofacial bone defects.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising nanofiber segments, wherein said nanofiber segments are electrospun nanofibers, wherein said nanofiber segments comprise a polymer, wherein said nanofiber segments have a length less than about 150 μm, and wherein said composition has a temperature less than about −20° C.

2. The composition of claim 1, wherein said composition has a temperature less than about −80° C.

3. A composition comprising nanofiber segments, wherein said nanofiber segments are electrospun nanofibers, wherein said nanofiber segments comprise a polymer, wherein said nanofiber segments have a length less than about 150 μm, wherein said composition has a temperature less than about −20° C., and wherein said polymer comprises poly-lactic-co-glycolic acid.

4. A composition comprising nanofiber segments, wherein said nanofiber segments are electrospun nanofibers, wherein said nanofiber segments comprise a polymer, wherein said nanofiber segments have a length less than about 150 μm, wherein said composition has a temperature less than about −20° C., and wherein said polymer comprises polycaprolactone.

5. The composition of claim 1, wherein said nanofiber segments are mineralized.

6. The composition of claim 1, wherein said nanofiber segments are crosslinked or thermally treated.

7. The composition of claim 1, wherein said nanofiber segments comprise cells and/or a bioactive agent.

8. The composition of claim 7, wherein said bioactive agent is selected from the group consisting of a therapeutic agent, a growth factor, a signaling molecule, a cytokine, a hemostatic agent, an antimicrobial, and an antibiotic.

9. The composition of claim 1, further comprising a pharmaceutically acceptable carrier.

10. The composition of claim 1, wherein said nanofiber segments are mineralized and comprise a bone morphogenic protein or fragment of analog thereof.

11. The composition of claim 1 consisting of said nanofiber segments and a pharmaceutically acceptable carrier.

12. The composition of claim 3, wherein said nanofiber segments are mineralized.

13. The composition of claim 3, wherein said nanofiber segments are crosslinked or thermally treated.

14. The composition of claim 3, wherein said nanofiber segments comprise cells and/or a bioactive agent.

15. The composition of claim 14, wherein said bioactive agent is selected from the group consisting of a therapeutic agent, a growth factor, a signaling molecule, a cytokine, a hemostatic agent, an antimicrobial, and an antibiotic.

16. The composition of claim 3, further comprising a pharmaceutically acceptable carrier.

17. The composition of claim 3, wherein said nanofiber segments are mineralized and comprise a bone morphogenic protein or fragment of analog thereof.

18. The composition of claim 3 consisting of said nanofiber segments and a pharmaceutically acceptable carrier.

19. The composition of claim 4, wherein said nanofiber segments are mineralized.

20. The composition of claim 4, wherein said nanofiber segments are crosslinked or thermally treated.

21. The composition of claim 4, wherein said nanofiber segments comprise cells and/or a bioactive agent.

22. The composition of claim 21, wherein said bioactive agent is selected from the group consisting of a therapeutic agent, a growth factor, a signaling molecule, a cytokine, a hemostatic agent, an antimicrobial, and an antibiotic.

23. The composition of claim 4, further comprising a pharmaceutically acceptable carrier.

24. The composition of claim 4, wherein said nanofiber segments are mineralized and comprise a bone morphogenic protein or fragment of analog thereof.

25. The composition of claim 4 consisting of said nanofiber segments and a pharmaceutically acceptable carrier.

26. A method for synthesizing a nanofiber microsphere, said method comprising electrospray microdripping the composition of claim 1 into freezing conditions and isolating the synthesized nanofiber microspheres.

27. A method for synthesizing a nanofiber microsphere, said method comprising electrospray microdripping the composition of claim 3 into freezing conditions and isolating the synthesized nanofiber microspheres.

28. A method for synthesizing a nanofiber microsphere, said method comprising electrospray microdripping the composition of claim 4 into freezing conditions and isolating the synthesized nanofiber microspheres.

29. The composition of claim 1, wherein said nanofiber segments have a length from 20 μm to 50 μm.

30. The composition of claim 3, wherein said nanofiber segments have a length from 20 μm to 50 μm.

31. The composition of claim 4, wherein said nanofiber segments have a length from 20 μm to 50 μm.

* * * * *

SEQUENCE LISTING

<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: BMP-2 knuckle epitope

```
<400> SEQUENCE: 1

Lys Ile Pro Lys Ala Ser Ser Val Pro Thr Glu Leu Ser Ala Ile Ser
1               5                   10                  15

Thr Leu Tyr Leu
            20

<210> SEQ ID NO 2
<211> LENGTH: 27
<212> TYPE: PRT
<213> ORGANISM: Artificial Sequence
<220> FEATURE:
<223> OTHER INFORMATION: E7 BMP-2 knuckle epitope

<400> SEQUENCE: 2

Glu Glu Glu Glu Glu Glu Glu Lys Ile Pro Lys Ala Ser Ser Val Pro
1               5                   10                  15

Thr Glu Leu Ser Ala Ile Ser Thr Leu Tyr Leu
            20                  25
```